United States Patent
Deciu et al.

(10) Patent No.: US 10,892,035 B2
(45) Date of Patent: Jan. 12, 2021

(54) METHODS AND PROCESSES FOR NON-INVASIVE ASSESSMENT OF GENETIC VARIATIONS

(71) Applicant: Sequenom, Inc., San Diego, CA (US)

(72) Inventors: Cosmin Deciu, San Diego, CA (US); Chen Zhao, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 867 days.

(21) Appl. No.: 15/517,107

(22) PCT Filed: Oct. 9, 2015

(86) PCT No.: PCT/US2015/054903
§ 371 (c)(1),
(2) Date: Apr. 5, 2017

(87) PCT Pub. No.: WO2016/057901
PCT Pub. Date: Apr. 14, 2016

(65) Prior Publication Data
US 2017/0316150 A1    Nov. 2, 2017

Related U.S. Application Data

(60) Provisional application No. 62/062,748, filed on Oct. 10, 2014.

(51) Int. Cl.
  *G16B 30/00* (2019.01)
  *C12Q 1/6869* (2018.01)

(52) U.S. Cl.
  CPC ........... *G16B 30/00* (2019.02); *C12Q 1/6869* (2013.01); *C12Q 2535/122* (2013.01)

(58) Field of Classification Search
  None
  See application file for complete search history.

(56) References Cited

PUBLICATIONS

Flicek et al. Sewnse from sequence reads: methods for alignment and assembly Nature Methods Supplement vil. 6, pp. S6-S12 (Year: 2009).*

* cited by examiner

*Primary Examiner* — John S Brusca
(74) *Attorney, Agent, or Firm* — Kilpatrick Townsend & Stockton LLP

(57) ABSTRACT

Provided herein are methods, processes and apparatuses for non-invasive assessment of genetic variations that make use of nucleic acid fragments from circulating cell free nucleic acid. Also provided herein are methods for partitioning one or more genomic regions of a reference genome into a plurality of portions according to one or more features.

20 Claims, 12 Drawing Sheets

FIG. 4

| | TRUTH | | |
|---|---|---|---|
| LDTv4 | | T21 | EUPLOID |
| | T21 | 21 | 0 |
| | EUPLOID | 0 | 313 |
| | TOTAL | 21 | 313 |

| | TRUTH | | |
|---|---|---|---|
| LDTv4 | | T18 | EUPLOID |
| | T18 | 6 | 0 |
| | EUPLOID | 1 | 328 |
| | TOTAL | 7 | 328 |

| | TRUTH | | |
|---|---|---|---|
| LDTv4 | | T13 | EUPLOID |
| | T13 | 7 | 0 |
| | EUPLOID | 0 | 328 |
| | TOTAL | 7 | 328 |

FIG. 8

| | Syndrome | Description | Position | Chr | Size(Mb) | Effective Size(Mb) |
|---|---|---|---|---|---|---|
| 1 | Cat-Eye syndrome (Type II) | Chr22 partial duplication | 1-16,971,860 | 22 | 16.97 | 0.00 |
| 2 | 1p36 microdeletion syndrome | Chr1 microdeletion | 10,001-12,840,259 | 1 | 12.83 | 10.50 |
| 3 | SOTOS syndrome | Microdeletion 5q35 probe metaphase and interphase study | 168,500,001-180,915,260 | 5 | 12.70 | 11.15 |
| 4 | Cri du Chat syndrome (5p deletion) | Chr5 microdeletion | 10,001-12,533,304 | 5 | 12.52 | 11.60 |
| 5 | Angelman syndrome (Prader-Willi) | Microdeletion 15q11-13 probe metaphase and interphase study | 20,700,001-33,600,000 | 15 | 10.00 | 7.20 |
| 6 | Kallman Deletion syndrome (STS) | Microdeletion Xp22.3 probe metaphase and interphase study | 103,700,001-108,700,000 | X | 8.70 | 0.00 |
| 7 | 16p11.2-p12.2 microdeletion syndrome | Chr16 microdeletion | 21,512,062-30,199,854 | 16 | 8.69 | 7.10 |
| 8 | 2q33.1 deletion syndrome | Chr2 microdeletion | 196,925,121-205,206,939 | 2 | 8.28 | 8.20 |
| 9 | DiGeorge/VCFS syndrome | Microdeletion 22q11.2 probe metaphase and interphase study | 17,900,001-25,900,000 | 22 | 8.00 | 5.00 |
| 10 | AZFb+AZFc | ChrY microdeletion | 19,964,826-27,793,830 | Y | 7.83 | 0.00 |
| 11 | Smith-Magenis syndrome | Microdeletion 17p11.2 probe metaphase and interphase study | 16,000,001-22,200,000 | 17 | 6.30 | 3.75 |
| 12 | AZFb | ChrY microdeletion | 20,118,045-26,065,197 | Y | 5.95 | 0.00 |
| 13 | Prader-Willi syndrome (Type II) (Angelman Type I) | Chr15 microdeletion | 22,749,354-28,438,266 | 15 | 5.69 | 4.15 |
| 14 | Williams ELN syndrome | Microdeletion 7q11.23 probe metaphase and interphase study | 72,200,001-77,500,000 | 7 | 5.30 | 2.85 |
| 15 | DiGeorge II | Microdeletion 10p14 probe metaphase and interphase study | 6,600,001-12,200,000 | 10 | 5.60 | 5.55 |

FIG. 11

Example workflows

A → B → C → D → E

A → B → C → D → E → F → G → H → I

A → B → C → D → E → J → K → L

A → B → C → D → E → F → J → M → N → I

A → B → C → J → K → L → I

METHODS AND PROCESSES FOR NON-INVASIVE ASSESSMENT OF GENETIC VARIATIONS

RELATED PATENT APPLICATIONS

This patent application is a 35 U.S.C. 371 national phase patent application of PCT/US2015/054903, filed on Oct. 9, 2015, entitled METHODS AND PROCESSES FOR NON-INVASIVE ASSESSMENT OF GENETIC VARIATIONS, naming Cosmin DECIU and Chen ZHAO as inventors, which claims the benefit of U.S. provisional patent application No. 62/062,748 filed on Oct. 10, 2014, entitled METHODS AND PROCESSES FOR NON-INVASIVE ASSESSMENT OF GENETIC VARIATIONS, naming Cosmin Deciu and Chen Zhao as inventors. The entire content of the foregoing applications is incorporated herein by reference, including all text, tables and drawings, for all purposes.

FIELD

Technology provided herein relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Trisomy 16, Trisomy 22, Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. In certain embodiments, identification of one or more genetic variations or variances involves the analysis of cell-free DNA. Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

Provided herein, in certain aspects, are methods for partitioning one or more genomic regions of a reference genome into a plurality of portions comprising a) determining sequencing coverage variability across a reference genome; b) selecting an initial portion length; c) partitioning at least two genomic regions according to the initial portion length in (b); d) comparing the sequencing coverage variability determined in (a) for each of the at least two genomic regions, thereby generating a comparison; e) recalculating the number of portions for at least one of the genomic regions according to the comparison in (d), thereby determining an optimized portion length; and f) re-partitioning at least one of the genomic regions into a plurality of portions according to the optimized portion length in (e).

Also provided herein, in certain aspects, are methods for partitioning one or more genomic regions of a reference genome into a plurality of portions comprising a) determining sequencing coverage variability across a reference genome; b) selecting an initial portion length; c) partitioning at least two genomic regions according to the initial portion length in (b); d) comparing the sequencing coverage variability determined in (a) for each of the at least two genomic regions, thereby generating a comparison; e) recalculating the number of portions for at least one of the genomic regions according to the comparison in (d), thereby determining an optimized portion length; f) re-partitioning at least one of the genomic regions into a plurality of portions according to the optimized portion length in (e), thereby generating a re-partitioned genomic region; g) estimating fetal fraction for a test sample from a pregnant female bearing a fetus; h) determining a minimum genomic region size; and i) adjusting the number of portions for each genomic region to comprise at least two portions, thereby generating a refined re-partitioned genomic region.

Also provided herein, in certain aspects, are methods for partitioning one or more genomic regions of a reference genome into a plurality of portions comprising: a) determining sequencing coverage variability across a reference genome; b) selecting an initial portion length; c) partitioning at least two genomic regions according to the initial portion length in (b); d) comparing the sequencing coverage variability determined in (a) for each of the at least two genomic regions, thereby generating a comparison; e) recalculating the number of portions for at least one of the genomic regions according to the comparison in (d), thereby determining an optimized portion length; f) re-partitioning at least one of the genomic regions into a plurality of portions according to the optimized portion length in (e), thereby generating a re-partitioned genomic region; g) determining a region-specific fetal fraction for each genomic region according to a correlation between nucleotide sequence read counts per portion and a weighting factor; h) determining a local minimum genomic region size; and i) adjusting the number of portions for each genomic region to comprise at least two portions, thereby generating a refined re-partitioned genomic region.

Also provided herein, in certain aspects, are methods for partitioning one or more genomic regions of a reference genome into a plurality of portions comprising: a) determining sequencing coverage variability across a reference genome; b) selecting an initial portion length; c) partitioning at least two genomic regions according to the initial portion length in (b); d) comparing the sequencing coverage variability determined in (a) for each of the at least two genomic regions, thereby generating a comparison; e) recalculating the number of portions for at least one of the genomic regions according to the comparison in (d), thereby determining an optimized portion length; f) re-partitioning at least one of the genomic regions into a plurality of portions according to the optimized portion length in (e), thereby generating a re-partitioned genomic region; g) estimating fetal fraction for a test sample from a pregnant female bearing a fetus; h) determining a region-specific fetal fraction for each genomic region according to a correlation between nucleotide sequence read counts per portion and a weighting factor; i) determining a local minimum genomic region size; and j) adjusting the number of portions for each genomic region to comprise at least two portions, thereby generating a refined re-partitioned genomic region.

Also provided herein, in certain aspects, are methods for partitioning one or more genomic regions of a reference genome into a plurality of portions comprising: a) determining sequencing coverage variability across a reference genome; b) selecting an initial portion length; c) partitioning at least two genomic regions according to the initial portion length in (b); d) determining a region-specific fetal fraction for each genomic region according to a correlation between nucleotide sequence read counts per portion and a weighting factor; e) determining a local minimum genomic region size; and f) adjusting the number of portions for each genomic region to comprise at least two portions, thereby generating a re-partitioned genomic region.

Also provided herein, in certain aspects, are methods for partitioning a reference genome, or part thereof, into a plurality of portions comprising: a) generating a guanine and cytosine (GC) profile for a reference genome, or part thereof; b) applying a segmenting process to the GC profile generated in (a), thereby providing discrete segments; and c) partitioning the reference genome, or part thereof, into a plurality of portions according to the discrete segments provided in (b), thereby generating a GC partitioned reference genome, or part thereof.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 4 shows truth tables for chromosomes 21, 18 and 13 for the LDTv4CE2 study.

FIG. 8 presents a list of certain examples of microdeletions and microduplications.

FIG. 11 shows example workflows for an optimal discretization method using certain steps presented in FIG. 10.

DETAILED DESCRIPTION

Figure 1:
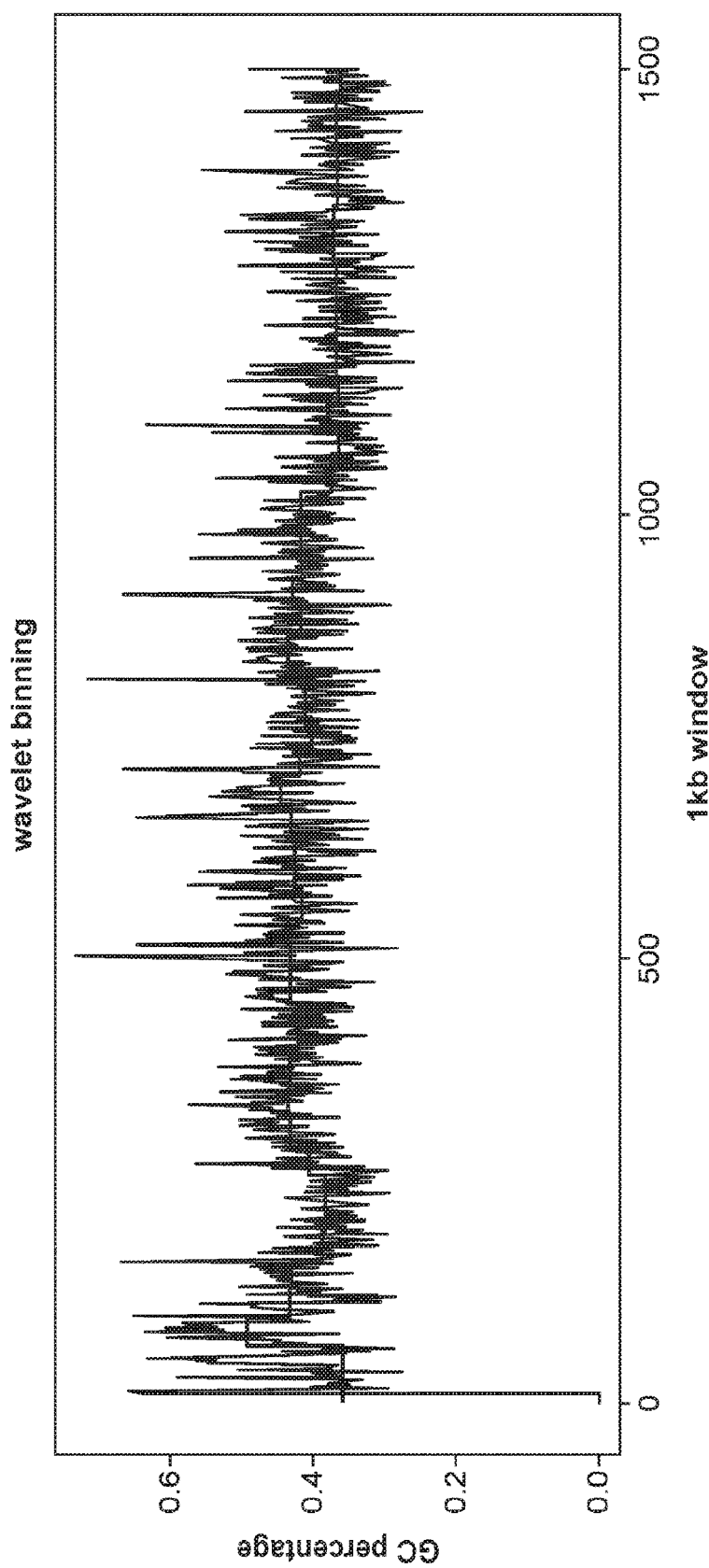
FIG. 1 shows a genomic region partitioned into segments of similar GC content using a wavelet binning method.

Provided herein are methods for determining the presence or absence of a genetic variation (e.g., a chromosome aneuploidy, microduplication or microdeletion) where a determination is made, in part and/or in full, according to nucleic acid sequences. Also provided herein are methods for partitioning one or more genomic regions of a reference genome into a plurality of portions according to sequencing coverage variability and/or sequence content (e.g., guanine and cytosine (GC) content). In some embodiments nucleic acid sequences are obtained from a sample obtained from a pregnant female (e.g., from the blood of a pregnant female). Also provided herein are improved data manipulation methods as well as systems, apparatuses and modules that, in some embodiments, carry out the methods described herein. In some embodiments, identifying a genetic variation by a method described herein can lead to a diagnosis of, or determine a predisposition to, a particular medical condition. Identifying a genetic variance can result in facilitating a medical decision and/or employing a helpful medical procedure.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, infant, child, adult).

Nucleic acid may be isolated from any type of suitable biological specimen or sample (e.g., a test sample). A sample or test sample can be any specimen that is isolated or obtained from a subject or part thereof (e.g., a human subject, a pregnant female, a fetus). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, cells (blood cells, placental cells, embryo or fetal cells, fetal nucleated cells or fetal cellular remnants) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. In some embodiments, a biological sample may be blood and sometimes plasma or serum. The term "blood" as used herein refers to a blood sample or preparation from a pregnant woman or a woman being tested for possible pregnancy. The term encompasses whole blood, blood product or any fraction of blood, such as serum, plasma, buffy coat, or the like as conventionally defined. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In certain embodiments a fluid or tissue sample is collected from a pregnant female during or just after (e.g., 0 to 72 hours after) giving birth (e.g., vaginal or non-vaginal birth (e.g., surgical delivery)).

Acquisition of Blood Samples and Extraction of DNA

Methods herein often include separating, enriching and analyzing fetal DNA found in maternal blood as a non-invasive means to detect the presence or absence of a maternal and/or fetal genetic variation and/or to monitor the health of a fetus and/or a pregnant female during and sometimes after pregnancy. Thus, the first steps of practicing certain methods herein often include obtaining a blood sample from a pregnant woman and extracting DNA from a sample.

Acquisition of Blood Samples

A blood sample can be obtained from a pregnant woman at a gestational age suitable for testing using a method of the present technology. A suitable gestational age may vary depending on the disorder tested, as discussed below. Collection of blood from a woman often is performed in accordance with the standard protocol hospitals or clinics generally follow. An appropriate amount of peripheral blood, e.g., typically between 5-50 ml, often is collected and may be stored according to standard procedure prior to further preparation. Blood samples may be collected, stored or transported in a manner that minimizes degradation or the quality of nucleic acid present in the sample.

Preparation of Blood Samples

An analysis of fetal DNA found in maternal blood may be performed using, e.g., whole blood, serum, or plasma. Methods for preparing serum or plasma from maternal blood are known. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons). Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

Nucleic Acid Isolation and Processing

Nucleic acid may be derived from one or more sources (e.g., cells, serum, plasma, buffy coat, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Ws.), and GFX™ Genomic Blood DNA Purification Kit (Amersham, Piscataway, N.J.), the like or combinations thereof.

Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 μg/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less, about 250 base pairs or less, about 200 base pairs or less, about 150 base pairs or less, about 100 base pairs or less, about 50 base pairs or less or about 25 base pairs or less. In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less).

In some embodiments, nucleic acid fragments of a certain length, range of lengths, or lengths under or over a particular threshold or cutoff are analyzed. In some embodiments, fragments having a length under a particular threshold or cutoff (e.g., 500 bp, 400 bp, 300 bp, 200 bp, 150 bp, 100 bp) are referred to as "short" fragments and fragments having a length over a particular threshold or cutoff (e.g., 500 bp, 400 bp, 300 bp, 200 bp, 150 bp, 100 bp) are referred to as "long" fragments. For example, fragments having a length under 200 bp are referred to as "short" fragments and fragments having a length equal to or over 200 bp are referred to as "long" fragments. In some embodiments, fragments of a certain length, range of lengths, or lengths under or over a particular threshold or cutoff are analyzed while fragments of a different length or range of lengths, or lengths over or under the threshold or cutoff are not analyzed. In some embodiments, fragments of a certain length, range of lengths, or lengths under a particular threshold or cutoff are analyzed separately from fragments of a different length or range of lengths, or lengths over the threshold or cutoff.

In some embodiments, fragments that are less than about 500 bp are analyzed. In some embodiments, fragments that are less than about 400 bp are analyzed. In some embodiments, fragments that are less than about 300 bp are analyzed. In some embodiments, fragments that are less than about 200 bp are analyzed. In some embodiments, fragments that are less than about 150 bp are analyzed. For example, fragments that are less than about 200 bp, 190 bp, 180 bp, 170 bp, 160 bp, 150 bp, 140 bp, 130 bp, 120 bp, 110 bp or 100 bp are analyzed. In some embodiments, fragments that are about 100 bp to about 200 bp are analyzed. For example, fragments that are about 190 bp, 180 bp, 170 bp, 160 bp, 150 bp, 140 bp, 130 bp, 120 bp or 110 bp are analyzed. In some embodiments, fragments that are in the range of about 100 bp to about 200 bp are analyzed. For example, fragments that are in the range of about 110 bp to about 190 bp, 130 bp to about 180 bp, 140 bp to about 170 bp, 140 bp to about 150 bp, 150 bp to about 160 bp, 145 bp to about 155 bp, or 130 bp to 140 bp are analyzed. In some embodiments, fragments that are about 135 bp are analyzed. In some embodiments, fragments that are about 200 bp or greater are analyzed. In some embodiments, fragments that are about 200 bp are analyzed. In some embodiments, fragments that are about 10 bp to about 30 bp shorter than other fragments of a certain length or range of lengths are analyzed. In some embodiments, fragments that are about 10 bp to about 20 bp shorter than other fragments of a certain length or range of lengths are analyzed. In some embodiments, fragments that are about 10 bp to about 15 bp shorter than other fragments of a certain length or range of lengths are analyzed.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

In some embodiments nucleic acids are fragmented or cleaved prior to, during or after a method described herein. Fragmented or cleaved nucleic acid may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

In some embodiments nucleic acid is fragmented or cleaved by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 20050112590, the like or combinations thereof.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. The term "amplified" as used herein refers to subjecting a target nucleic acid in a sample to a process that linearly or exponentially generates amplicon nucleic acids having the same or substantially the same nucleotide sequence as the target nucleic acid, or segment thereof. In certain embodiments the term "amplified" refers to a method that comprises a polymerase chain reaction (PCR). For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from segments or parts of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel). The term "specific cleavage agent" as used herein refers to an agent, sometimes a chemical or an enzyme that can cleave a nucleic acid at one or more specific sites.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a suitable sequence analysis.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Determining Fetal Nucleic Acid Content

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction". In some embodiments "fetal fraction" refers to the fraction of fetal nucleic acid in circulating cell-free nucleic acid in a sample (e.g., a blood sample, a serum sample, a plasma sample) obtained from a pregnant female. In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In certain embodiments, the amount of fetal nucleic acid from a maternal sample can be determined relative to the total amount of nucleic acid present, thereby providing the percentage of fetal nucleic acid in the sample. In certain embodiments, the copy number of fetal nucleic acid can be determined in a maternal sample. In certain embodiments, the amount of fetal nucleic acid can be determined in a sequence-specific (or portion-specific) manner and sometimes with sufficient sensitivity to allow for accurate chromosomal dosage analysis (for example, to detect the presence or absence of a fetal aneuploidy, micro-duplication or microdeletion).

A fetal quantifier assay (FQA) can be performed in conjunction with any of the methods described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In certain embodiments, the restriction efficiency can be determined and the efficiency rate is used to further determine the amount of fetal DNA.

In certain embodiments, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In certain embodiments, the absolute copy number of fetal nucleic acid in a maternal sample can be determined, for example, using mass spectrometry and/or a system that uses a competitive PCR approach for absolute copy number measurements. See for example, Ding and Cantor (2003) Proc. Natl. Acad. Sci. USA 100:3059-3064, and U.S. Patent Application Publication No. 2004/0081993, both of which are hereby incorporated by reference.

In certain embodiments, fetal fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In certain embodiments, fetal alleles are identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

Fetal fraction can be determined, in some embodiments, using methods that incorporate information derived from maternal chromosomal aberrations as described, for example, in International Application Publication No. WO2014/055774, which is incorporated by reference herein. Fetal fraction can be determined, in some embodiments, using methods that incorporate information derived from sex chromosomes.

Fetal fraction can be determined, in some embodiments, using methods that incorporate fragment length information (e.g., fragment length ratio (FLR) analysis, fetal ratio statistic (FRS) analysis as described in International Application Publication No. WO2013/177086, which is incorporated by reference herein). Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts, for example, to counts from fragments over a particular length threshold and/or to the amount of total nucleic acid in the sample. Methods for counting nucleic acid fragments of a particular length are described in further detail in International Application Publication No. WO2013/177086.

Fetal fraction can be determined, in some embodiments, according to portion-specific fetal fraction estimates. Portion-specific fetal fraction also may be referred to as binwise fetal fraction (BFF), enet, and sequence-based fetal fraction (SeqFF). Without being limited to theory, the amount of reads from fetal CCF fragments (e.g., fragments of a particular length, or range of lengths) often map with ranging frequencies to portions (e.g., within the same sample, e.g., within the same sequencing run). Also, without being limited to theory, certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus).

In some embodiments portion-specific fetal fraction estimates are determined based in part on portion-specific parameters and their relation to fetal fraction. Portion-specific parameters can be any suitable parameter that is reflective of (e.g., correlates with) the amount or proportion of reads from CCF fragment lengths of a particular size (e.g., size range) in a portion. A portion-specific parameter can be an average, mean or median of portion-specific parameters determined for multiple samples. Any suitable portion-specific parameter can be used. Non-limiting examples of portion-specific parameters include FLR (e.g., FRS), an amount of reads having a length less than a selected fragment length, genomic coverage (i.e., coverage), mappability, counts (e.g., counts of sequence reads mapped to the portion, e.g., normalized counts, ChAI normalized counts), DNaseI-sensitivity, methylation state, acetylation, histone distribution, guanine-cytosine (GC) content, chromatin structure, the like or combinations thereof. A portion-specific parameter can be any suitable parameter that correlates with FLR and/or FRS in a portion-specific manner. In some embodiments, some or all portion-specific parameters are a direct or indirect representation of an FLR for a portion. In some embodiments a portion-specific parameter is not guanine-cytosine (GC) content.

In some embodiments a portion-specific parameter is any suitable value representing, correlated with or proportional to an amount of reads from CCF fragments where the reads mapped to a portion have a length less than a selected fragment length. In certain embodiments, a portion-specific parameter is a representation of the amount of reads derived from relatively short CCF fragments (e.g., about 200 base pairs or less) that map to a portion. CCF fragments having a length less than a selected fragment length often are relatively short CCF fragments, and sometimes a selected fragment length is about 200 base pairs or less (e.g., CCF fragments that are about 190, 180, 170, 160, 150, 140, 130, 120, 110, 100, 90, or 80 bases in length). The length of a CCF fragment or a read derived from a CCF fragment can be determined (e.g., deduced or inferred) by any suitable method (e.g., a sequencing method, a hybridization approach). In some embodiments the length of a CCF fragment is determined (e.g., deduced or inferred) by a read obtained from a paired-end sequencing method. In certain embodiments the length of a CCF fragment template is determined directly from the length of a read derived from the CCF fragment (e.g., single-end read).

Portion-specific parameters can be weighted or adjusted by one or more weighting factors. In some embodiments weighted or adjusted portion-specific parameters can provide portion-specific fetal fraction estimates for a sample (e.g., a test sample). In some embodiments weighting or adjusting generally converts the counts of a portion (e.g., reads mapped to a portion) or another portion-specific parameter into a portion-specific fetal fraction estimate, and such a conversion sometimes is considered a transformation.

In some embodiments a weighting factor is a coefficient or constant that, in part, describes and/or defines a relation between a fetal fraction (e.g., a fetal fraction determined from multiple samples) and a portion-specific parameter for multiple samples (e.g., a training set). In some embodiments a weighting factor is determined according to a relation for multiple fetal fraction determinations and multiple portion-specific parameters. A relation may be defined by one or more weighting factors and one or more weighting factors may be determined from a relation. In some embodiments a weighting factor (e.g., one or more weighting factors) is determined from a fitted relation for a portion according to (i) a fraction of fetal nucleic acid determined for each of multiple samples, and (ii) a portion-specific parameter for multiple samples.

A weighting factor can be any suitable coefficient, estimated coefficient or constant derived from a suitable relation (e.g., a suitable mathematical relation, an algebraic relation, a fitted relation, a regression, a regression analysis, a regression model). A weighting factor can be determined according to, derived from, or estimated from a suitable relation. In some embodiments weighting factors are estimated coefficients from a fitted relation. Fitting a relation for multiple samples is sometimes referred to as training a model. Any suitable model and/or method of fitting a relationship (e.g., training a model to a training set) can be used. Non-limiting examples of a suitable model that can be used include a regression model, linear regression model, simple regression model, ordinary least squares regression model, multiple regression model, general multiple regression model, polynomial regression model, general linear model, generalized linear model, discrete choice regression model, logistic regression model, multinomial logit model, mixed logit model, probit model, multinomial probit model, ordered logit model, ordered probit model, Poisson model, multivariate response regression model, multilevel model, fixed effects model, random effects model, mixed model, nonlinear regression model, nonparametric model, semiparametric model, robust model, quantile model, isotonic model, principal components model, least angle model, local model, segmented model, and errors-in-variables model. In some embodiments a fitted relation is not a regression model. In some embodiments a fitted relations is chosen from a decision tree model, support-vector machine model and neural network model. The result of training a model (e.g., a regression model, a relation) is often a relation that can be described mathematically where the relation comprises one or more coefficients (e.g., weighting factors). More complex multivariate models may determine one, two, three or more weighting factors. In some embodiments a model is trained according to fetal fraction and two or more portion-specific parameters (e.g., coefficients) obtained from multiple samples (e.g., fitted relationships fitted to multiple samples, e.g., by a matrix).

A weighting factor can be derived from a suitable relation (e.g., a suitable mathematical relation, an algebraic relation, a fitted relation, a regression, a regression analysis, a regression model) by a suitable method. In some embodiments fitted relations are fitted by an estimation, non-limiting examples of which include least squares, ordinary least squares, linear, partial, total, generalized, weighted, non-linear, iteratively reweighted, ridge regression, least absolute deviations, Bayesian, Bayesian multivariate, reduced-rank, LASSO, Weighted Rank Selection Criteria (WRSC), Rank Selection Criteria (RSC), an elastic net estimator (e.g., an elastic net regression) and combinations thereof.

A weighting factor can be determined for or associated with any suitable portion of a genome. A weighting factor can be determined for or associated with any suitable portion of any suitable chromosome. In some embodiments a weighting factor is determined for or associated with some or all portions in a genome. In some embodiments a weighting factor is determined for or associated with portions of some or all chromosomes in a genome. A weighting factor is sometimes determined for or associated with portions of selected chromosomes. A weighting factor can be determined for or associated with portions of one or more autosomes. A weighting factor can be determined for or associated with portions in a plurality of portions that include portions in autosomes or a subset thereof. In some embodiments a weighting factor is determined for or associated with portions of a sex chromosome (e.g. ChrX and/or ChrY). A weighting factor can be determined for or associated with portions of one or more autosomes and one or more sex chromosomes. In certain embodiments a weighting factor is determined for or associated with portions in a plurality of portions in all autosomes and chromosomes X and Y. A weighting factor can be determined for or associated with portions in a plurality of portions that does not include portions in an X and/or Y chromosome. In certain embodiments a weighting factor is determined for or associated with portions of a chromosome where the chromosome comprises an aneuploidy (e.g., a whole chromosome aneuploidy). In certain embodiments a weighting factor is determined for or associated only with portions of a chromosome where the chromosome is not aneuploid (e.g., a euploid chromosome). A weighting factor can be determined for or associated with portions in a plurality of portions that does not include portions in chromosomes 13, 18 and/or 21.

In some embodiments a weighting factor is determined for a portion according to one or more samples (e.g., a training set of samples). Weighting factors are often specific to a portion. In some embodiments one or more weighting factors are independently assigned to a portion. In some embodiments a weighting factor is determined according to a relation for a fetal fraction determination (e.g., a sample specific fetal fraction determination) for multiple samples and a portion-specific parameter determined according to multiple samples. Weighting factors are often determined from multiple samples, for example, from about 20 to about 100,000 or more, from about 100 to about 100,000 or more, from about 500 to about 100,000 or more, from about 1000 to about 100,000 or more, or from about 10,000 to about 100,000 or more samples. Weighting factors can be determined from samples that are euploid (e.g., samples from subjects comprising a euploid fetus, e.g., samples where no aneuploid chromosome is present). In some embodiments weighting factors are obtained from samples comprising an aneuploid chromosome (e.g., samples from subjects comprising a euploid fetus). In some embodiments weighting factors are determined from multiple samples from subjects having a euploid fetus and from subjects having a trisomy fetus. Weighting factors can be derived from multiple samples where the samples are from subjects having a male fetus and/or a female fetus.

A fetal fraction is often determined for one or more samples of a training set from which a weighting factor is derived. A fetal fraction from which a weighting factor is determined is sometimes a sample specific fetal fraction determination. A fetal fraction from which a weighting factor is determined can be determined by any suitable method described herein or known in the art. In some embodiments a determination of fetal nucleic acid content (e.g., fetal fraction) is performed using a suitable fetal quantifier assay (FQA) described herein or known in the art, non-limiting examples of which include fetal fraction determinations according to markers specific to a male fetus, based on allelic ratios of polymorphic sequences, according to one or more markers specific to fetal nucleic acid and not maternal nucleic acid, by use of methylation-based DNA discrimination (e.g., A. Nygren, et al., (2010) Clinical Chemistry 56(10):1627-1635), by a mass spectrometry method and/or a system that uses a competitive PCR approach, by a method described in U.S. Patent Application Publication No. 2010/0105049, which is hereby incorporated by reference, the like or combinations thereof. Often a fetal fraction is determined, in part, according to a level (e.g., one or more genomic section levels, a level of a profile) of a Y chromosome. In some embodiments a fetal fraction is determined according to a suitable assay of a Y chromosome (e.g., by comparing the amount of fetal-specific locus (such as the SRY locus on chromosome Y in male pregnancies) to that of a locus on any autosome that is common to both the mother and the fetus by using quantitative real-time PCR (e.g., Lo Y M, et al. (1998) Am J Hum Genet 62:768-775.)).

Portion-specific parameters (e.g., for a test sample) can be weighted or adjusted by one or more weighting factors (e.g., weighting factors derived from a training set). For example, a weighting factor can be derived for a portion according to a relation of a portion-specific parameter and a fetal fraction determination for a training set of multiple samples. A portion-specific parameter of a test sample can then be adjusted and/or weighted according to the weighting factor derived from the training set. In some embodiments a portion-specific parameter from which a weighting factor is derived, is the same as the portion-specific parameter (e.g., of a test sample) that is adjusted or weighted (e.g., both parameters are an FLR). In certain embodiment, a portion-specific parameter, from which a weighting factor is derived, is different than the portion-specific parameter (e.g., of a test sample) that is adjusted or weighted. For example, a weighting factor may be determined from a relation between coverage (i.e., a portion-specific parameter) and fetal fraction for a training set of samples, and an FLR (i.e., another portion-specific parameter) for a portion of a test sample can be adjusted according to the weighting factor derived from coverage. Without being limited by theory, a portion-specific parameter (e.g., for a test sample) can sometimes be adjusted and/or weighted by a weighting factor derived from a different portion-specific parameter (e.g., of a training set) due to a relation and/or correlation between each portion-specific parameter and a common portion-specific FLR.

A portion-specific fetal fraction estimate can be determined for a sample (e.g., a test sample) by weighting a portion-specific parameter by a weighting factor determined for that portion. Weighting can comprise adjusting, converting and/or transforming a portion-specific parameter according to a weighting factor by applying any suitable mathematical manipulation, non-limiting examples of which include multiplication, division, addition, subtraction, integration, symbolic computation, algebraic computation, algorithm, trigonometric or geometric function, transformation (e.g., a Fourier transform), the like or combinations thereof. Weighting can comprise adjusting, converting and/or transforming a portion-specific parameter according to a weighting factor a suitable mathematical model.

In some embodiments a fetal fraction is determined for a sample according to one or more portion-specific fetal fraction estimates. In some embodiments a fetal fraction is determined (e.g., estimated) for a sample (e.g., a test sample) according to weighting or adjusting a portion-specific parameter for one or more portions. In certain embodiments a fraction of fetal nucleic acid for a test sample is estimated based on adjusted counts or an adjusted subset of counts. In certain embodiments a fraction of fetal nucleic acid for a test sample is estimated based on an adjusted FLR, an adjusted FRS, adjusted coverage, and/or adjusted mappability for a portion. In some embodiments about 1 to about 500,000, about 100 to about 300,000, about 500 to about 200,000, about 1000 to about 200,000, about 1500 to about 200,000, or about 1500 to about 50,000 portion-specific parameters are weighted or adjusted.

A fetal fraction (e.g., for a test sample) can be determined according to multiple portion-specific fetal fraction estimates (e.g., for the same test sample) by any suitable method. In some embodiments a method for increasing the accuracy of the estimation of a fraction of fetal nucleic acid in a test sample from a pregnant female comprises determining one or more portion-specific fetal fraction estimates where the estimate of fetal fraction for the sample is determined according to the one or more portion-specific fetal fraction estimates. In some embodiments estimating or determining a fraction of fetal nucleic acid for a sample (e.g., a test sample) comprises summing one or more portion-specific fetal fraction estimates. Summing can comprise determining an average, mean, median, AUC, or integral value according to multiple portion-specific fetal fraction estimates.

In some embodiments a method for increasing the accuracy of the estimation of a fraction of fetal nucleic acid in a test sample from a pregnant female, comprises obtaining counts of sequence reads mapped to portions of a reference genome, which sequence reads are reads of circulating cell-free nucleic acid from a test sample from a pregnant female, where at least a subset of the counts obtained are derived from a region of the genome that contributes a greater number of counts derived from fetal nucleic acid relative to total counts from the region than counts of fetal nucleic acid relative to total counts of another region of the genome. In some embodiments an estimate of the fraction of fetal nucleic acid is determined according to a subset of the portions, where the subset of the portions is selected according to portions to which are mapped a greater number of counts derived from fetal nucleic acid than counts of fetal nucleic acid of another portion. In some embodiments the subset of the portions is selected according to portions to which are mapped a greater number of counts derived from fetal nucleic acid, relative to non-fetal nucleic acid, than counts of fetal nucleic acid, relative to non-fetal nucleic acid, of another portion. The counts mapped to all or a subset of the portions can be weighted, thereby providing weighted counts. The weighted counts can be utilized for estimating the fraction of fetal nucleic acid, and the counts can be weighted according to portions to which are mapped a greater number of counts derived from fetal nucleic acid than counts of fetal nucleic acid of another portion. In some embodiments the counts are weighted according to portions to which are mapped a greater number of counts derived from fetal nucleic acid, relative to non-fetal nucleic acid, than counts of fetal nucleic acid, relative to non-fetal nucleic acid, of another portion.

A fetal fraction can be determined for a sample (e.g., a test sample) according to multiple portion-specific fetal fraction estimates for the sample where the portions-specific estimates are from portions of any suitable region or segment of a genome. Portion-specific fetal fraction estimates can be determined for one or more portions of a suitable chromosome (e.g., one or more selected chromosomes, one or more autosomes, a sex chromosome (e.g. ChrX and/or ChrY), an aneuploid chromosome, a euploid chromosome, the like or combinations thereof).

In some embodiments, determining fetal fraction comprises (a) obtaining counts of sequence reads mapped to portions of a reference genome, which sequence reads are reads of circulating cell-free nucleic acid from a test sample from a pregnant female; (b) weighting, e.g., using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples; and (c) estimating a fraction of fetal nucleic acid for the test sample based on the portion-specific fetal fraction estimates.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection, microduplication or microdeletion detection, fetal gender determination) methods described herein. For example, to achieve a fetal gender or aneuploidy, microduplication or microdeletion determination method with a given sensitivity or specificity, a fetal nucleic acid quantification method may be implemented prior to, during or after fetal gender or aneuploidy, microduplication or microdeletion determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or aneuploidy, microduplication or microdeletion determination, or the presence or absence of aneuploidy or genetic variation, for example. In certain embodiments, determinations of, for example, fetal gender or the presence or absence of aneuploidy, microduplication or microdeletion are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy, microduplication or microdeletion. In some embodiments, identifying the presence or absence of a chromosome aneuploidy, microduplication or microdeletion does not require the sequence differentiation of fetal versus maternal DNA. In certain embodiments this is because the summed contribution of both maternal and fetal sequences in a particular chromosome, chromosome portion or segment thereof is analyzed. In some embodiments, identifying the presence or absence of a chromosome aneuploidy, microduplication or microdeletion does not rely on a priori sequence information that would distinguish fetal DNA from maternal DNA.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In certain embodiments, a method for determining fetal fraction described above also can be used to enrich for fetal nucleic acid. In certain embodiments, maternal nucleic acid is selectively removed (partially, substantially, almost completely or completely) from the sample. In certain embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In certain embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e. non-target) nucleic acid. In certain embodiments, the method can be repeated for at least one additional cycle. In certain embodiments, the same target-specific primer pair is used to prime each of the first and second cycles of extension, and In certain embodiments, different target-specific primer pairs are used for the first and second cycles.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (i.e. tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In certain embodiments, certain enrichment methods (e.g., certain MPS and/or MPSS-based enrichment methods) can include amplification (e.g., PCR)-based approaches. In certain embodiments, loci-specific amplification methods can be used (e.g., using loci-specific amplification primers). In certain embodiments, a multiplex SNP allele PCR approach can be used. In certain embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In certain embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In certain embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In certain embodiments, a microfluidics approach can be used. In certain embodiments, an array-based microfluidics approach can be used. For example, such an approach can involve the use of a microfluidics array (e.g., Fluidigm) for amplification at low plex and incorporation of index and capture probes, followed by sequencing. In certain embodiments, an emulsion microfluidics approach can be used, such as, for example, digital droplet PCR.

In certain embodiments, universal amplification methods can be used (e.g., using universal or non-loci-specific amplification primers). In certain embodiments, universal amplification methods can be used in combination with pull-down approaches. In certain embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In certain embodiments, pull-down approaches can be used in combination with ligation-based methods. In certain embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In certain embodiments, pull-down approaches can be used in combination with extension and ligation-based methods. In certain embodiments, a method can include molecular inversion probe (MIP) extension and ligation. For example, such an approach can involve the use of molecular inversion probes in combination with sequence adapters followed by universal amplification and sequencing. In certain embodiments, complementary DNA can be synthesized and sequenced without amplification.

In certain embodiments, extension and ligation approaches can be performed without a pull-down component. In certain embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in certain embodiments.

In certain embodiments, pull-down approaches can be used with an optional amplification component or with no amplification component. In certain embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In certain embodiments, a method can include a biotinylated pull-down assay with extension and ligation of adaptor sequence in combination with circular single stranded ligation. For example, such an approach can involve the use of selector probes to capture regions of interest (i.e. target sequences), extension of the probes, adaptor ligation, single stranded circular ligation, optional amplification, and sequencing. In certain embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest) or segments of interest thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain embodiments, length-based separation approaches can include fragment circularization, chemical treatment (e.g., formaldehyde, polyethylene glycol (PEG)), mass spectrometry and/or size-specific nucleic acid amplification, for example.

In some embodiments, nucleic acid fragments of a certain length, range of lengths, or lengths under or over a particular threshold or cutoff are separated from the sample. In some embodiments, fragments having a length under a particular threshold or cutoff (e.g., 500 bp, 400 bp, 300 bp, 200 bp, 150 bp, 100 bp) are referred to as "short" fragments and fragments having a length over a particular threshold or cutoff (e.g., 500 bp, 400 bp, 300 bp, 200 bp, 150 bp, 100 bp) are referred to as "long" fragments. In some embodiments, fragments of a certain length, range of lengths, or lengths under or over a particular threshold or cutoff are retained for analysis while fragments of a different length or range of lengths, or lengths over or under the threshold or cutoff are not retained for analysis. In some embodiments, fragments that are less than about 500 bp are retained. In some embodiments, fragments that are less than about 400 bp are retained. In some embodiments, fragments that are less than about 300 bp are retained. In some embodiments, fragments that are less than about 200 bp are retained. In some embodiments, fragments that are less than about 150 bp are retained. For example, fragments that are less than about 190 bp, 180 bp, 170 bp, 160 bp, 150 bp, 140 bp, 130 bp, 120 bp, 110 bp or 100 bp are retained. In some embodiments, fragments that are about 100 bp to about 200 bp are retained. For example, fragments that are about 190 bp, 180 bp, 170 bp, 160 bp, 150 bp, 140 bp, 130 bp, 120 bp or 110 bp are retained. In some embodiments, fragments that are in the range of about 100 bp to about 200 bp are retained. For example, fragments that are in the range of about 110 bp to about 190 bp, 130 bp to about 180 bp, 140 bp to about 170 bp, 140 bp to about 150 bp, 150 bp to about 160 bp, or 145 bp to about 155 bp are retained. In some embodiments, fragments that are about 10 bp to about 30 bp shorter than other fragments of a certain length or range of lengths are retained. In some embodiments, fragments that are about 10 bp to about 20 bp shorter than other fragments of a certain length or range of lengths are retained. In some embodiments, fragments that are about 10 bp to about 15 bp shorter than other fragments of a certain length or range of lengths are retained.

In some embodiments, nucleic acid is enriched for a particular nucleic acid fragment length, range of lengths, or lengths under or over a particular threshold or cutoff using one or more bioinformatics-based (e.g., in silico) methods. For example, nucleotide sequence reads can be obtained for nucleic acid fragments using a suitable nucleotide sequencing process. In some instances, such as when a paired-end sequencing method is used, the length of a particular fragment can be determined based on the positions of mapped sequence reads obtained from each terminus of the fragment. Sequence reads used for a particular analysis (e.g., determining the presence or absence of a genetic variation) can be enriched or filtered according to one or more selected fragment lengths or fragment length threshold values of corresponding fragments, as described herein.

Certain length-based separation methods that can be used with methods described herein employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In certain embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Nucleic Acid Library

In some embodiments a nucleic acid library is a plurality of polynucleotide molecules (e.g., a sample of nucleic acids) that are prepared, assemble and/or modified for a specific process, non-limiting examples of which include immobilization on a solid phase (e.g., a solid support, e.g., a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adaptors. In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments a polynucleotide of known sequence comprises a universal sequence. A universal sequence is a specific nucleotide acid sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using ccfDNA).

In certain embodiments, a ligation-based library preparation method is used (e.g., ILLUMINA TRUSEQ, Illumina, San Diego Calif.). Ligation-based library preparation methods often make use of an adaptor (e.g., a methylated adaptor) design which can incorporate an index sequence at the initial ligation step and often can be used to prepare samples for single-read sequencing, paired-end sequencing and multiplexed sequencing. For example, sometimes nucleic acids (e.g., fragmented nucleic acids or ccfDNA) are end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method or apparatus, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Sequencing

In some embodiments, nucleic acids (e.g., nucleic acid fragments, sample nucleic acid, cell-free nucleic acid) are sequenced. In certain embodiments, a full or substantially full sequence is obtained and sometimes a partial sequence is obtained.

In some embodiments, fragment length is determined using a sequencing method. In some embodiments, fragment length is determined using a paired-end sequencing platform. Such platforms involve sequencing of both ends of a nucleic acid fragment. Generally, the sequences corresponding to both ends of the fragment can be mapped to a reference genome (e.g., a reference human genome). In certain embodiments, both ends are sequenced at a read length that is sufficient to map, individually for each fragment end, to a reference genome. Examples of paired-end sequence read lengths are described below. In certain embodiments, all or a portion of the sequence reads can be mapped to a reference genome without mismatch. In some embodiments, each read is mapped independently. In some embodiments, information from both sequence reads (i.e., from each end) is factored in the mapping process. The length of a fragment can be determined, for example, by calculating the difference between genomic coordinates assigned to each mapped paired-end read.

In some embodiments, fragment length can be determined using a sequencing process whereby a complete, or substantially complete, nucleotide sequence is obtained for the fragment. Such sequencing processes include platforms that generate relatively long read lengths (e.g., Roche 454, Ion Torrent, single molecule (Pacific Biosciences), real-time SMRT technology, and the like).

In some embodiments some or all nucleic acids in a sample are enriched and/or amplified (e.g., non-specifically, e.g., by a PCR based method) prior to or during sequencing. In certain embodiments specific nucleic acid portions or subsets in a sample are enriched and/or amplified prior to or during sequencing. In some embodiments, a portion or subset of a pre-selected pool of nucleic acids is sequenced randomly. In some embodiments, nucleic acids in a sample are not enriched and/or amplified prior to or during sequencing.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length about 1000 bp or more.

In some embodiments the nominal, average, mean or absolute length of single-end reads sometimes is about 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length.

In certain embodiments, the nominal, average, mean or absolute length of paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides, about 18 contiguous nucleotides, about 20 contiguous nucleotides, about 25 contiguous nucleotides, about 36 contiguous nucleotides or about 45 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, microduplication or microdeletion, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, a representative fraction of a genome is sequenced and is sometimes referred to as "coverage" or "fold coverage". For example, a 1-fold coverage indicates that roughly 100% of the nucleotide sequences of the genome are represented by reads. In some embodiments "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage).

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane are dependent on the number of unique identifiers utilized during library preparation and/or probe design. single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments MPS sequencing methods utilize a targeted approach, where specific chromosomes, genes or regions of interest are sequences. In certain embodiments a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEM-FET sensor), the like or combinations thereof. Other sequencing methods that may be used to conduct methods herein include digital PCR and sequencing by hybridization.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore.

A suitable MPS method, system or technology platform for conducting methods described herein can be used to obtain nucleic acid sequencing reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

Mapping Reads

Sequence reads can be mapped and the number of reads mapping to a specified nucleic acid region (e.g., a chromosome, portion or segment thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped", "a mapped sequence read" or "a mapped read". In certain embodiments, a mapped sequence read is referred to as a "hit" or "count". In some embodiments, mapped sequence reads are grouped together according to various parameters and assigned to particular portions, which are discussed in further detail below.

As used herein, the terms "aligned", "alignment", or "aligning" refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate portions (described hereafter), for example.

In some embodiments mapped sequence reads and/or information associated with a mapped sequence read are stored on and/or accessed from a non-transitory computer-readable storage medium in a suitable computer-readable format. A "computer-readable format" is sometimes referred to generally herein as a format. In some embodiments mapped sequence reads are stored and/or accessed in a suitable binary format, a text format, the like or a combination thereof. A binary format is sometimes a BAM format. A text format is sometimes a sequence alignment/map (SAM) format. Non-limiting examples of binary and/or text formats include BAM, SAM, SRF, FASTQ, Gzip, the like, or combinations thereof. In some embodiments mapped sequence reads are stored in and/or are converted to a format that requires less storage space (e.g., less bytes) than a traditional format (e.g., a SAM format or a BAM format). In some embodiments mapped sequence reads in a first format are compressed into a second format requiring less storage space than the first format. The term "compressed" as used herein refers to a process of data compression, source coding, and/or bit-rate reduction where a computer readable data file is reduced in size. In some embodiments mapped sequence reads are compressed from a SAM format in a binary format. Some data sometimes is lost after a file is compressed. Sometimes no data is lost in a compression process. In some file compression embodiments, some data is replaced with an index and/or a reference to another data file comprising information regarding a mapped sequence read. In some embodiments a mapped sequence read is stored in a binary format comprising or consisting of a read count, a chromosome identifier (e.g., that identifies a chromosome to which a read is mapped) and a chromosome position identifier (e.g., that identifies a position on a chromosome to which a read is mapped). In some embodiments a binary format comprises a 20 byte array, a 16 byte array, an 8 byte array, a 4 byte array or a 2 byte array. In some embodiments mapped read information is stored in an array in a 10 byte format, 9 byte format, 8 byte format, 7 byte format, 6 byte format, 5 byte format, 4 byte format, 3 byte format or 2 byte format. Sometimes mapped read data is stored in a 4 byte array comprising a 5 byte format. In some embodiments a binary format comprises a 5-byte format comprising a 1-byte chromosome ordinal and a 4-byte chromosome position. In some embodiments mapped reads are stored in a compressed binary format that is about 100 times, about 90 times, about 80 times, about 70 times, about 60 times, about 55 times, about 50 times, about 45 times, about 40 times or about 30 times smaller than a sequence alignment/map (SAM) format. In some embodiments mapped reads are stored in a compress binary format that is about 2 times smaller to about 50 times smaller than (e.g., about 30, 25, 20, 19, 18, 17, 16, 15, 14, 13, 12, 11, 10, 9, 8, 7, 6, or about 5 times smaller than) a GZip format.

In some embodiments a system comprises a compression module. In some embodiments mapped sequence read information stored on a non-transitory computer-readable storage medium in a computer-readable format is compressed by a compression module. A compression module sometimes converts mapped sequence reads to and from a suitable format. A compression module can accept mapped sequence reads in a first format, convert them into a compressed format (e.g., a binary format, 5) and transfer the compressed reads to another module (e.g., a bias density module 6) in some embodiments. A compression module often provides sequence reads in a binary format 5 (e.g., a BReads format). Non-limiting examples of a compression module include GZIP, BGZF, and BAM, the like or modifications thereof).

The following provides an example of converting an integer into a 4-byte array using java:

```
public static final byte[ ]
convertToByteArray(int value)
{
return new byte[ ] {
(byte)(value >>> 24),
(byte)(value >>> 16),
(byte)(value >>> 8),
(byte)value};
}
```

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In certain embodiments, mappability is assessed for a genomic region (e.g., portion, genomic portion, portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

Portions

In some embodiments, mapped sequence reads (i.e. sequence tags) are grouped together according to various parameters and assigned to particular portions (e.g., portions of a reference genome). Often, individual mapped sequence reads can be used to identify a portion (e.g., the presence, absence or amount of a portion) present in a sample. In some embodiments, the amount of a portion is indicative of the amount of a larger sequence (e.g. a chromosome) in the sample. The term "portion" can also be referred to herein as a "genomic section", "bin", "region", "partition", "portion of a reference genome", "portion of a chromosome" or "genomic portion." In some embodiments a portion is an entire chromosome, a segment of a chromosome, a segment of a reference genome, a segment spanning multiple chromosome, multiple chromosome segments, and/or combinations thereof. In some embodiments, a portion is predefined based on specific parameters. In some embodiments, a portion is arbitrarily defined based on partitioning of a genome (e.g., partitioned by size, GC content, sequencing coverage variability, contiguous regions, contiguous regions of an arbitrarily defined size, and the like). Methods for partitioning a genome (e.g., a reference genome, or part thereof) are provided herein and described in further detail below.

In some embodiments, a portion is delineated based on one or more parameters which include, for example, length or a particular feature or features of the sequence. Portions can be selected, filtered and/or removed from consideration using any suitable criteria know in the art or described herein. In some embodiments, a portion is based on a particular length of genomic sequence. In some embodiments, a method can include analysis of multiple mapped sequence reads to a plurality of portions. Portions can be approximately the same length or portions can be different lengths. In some embodiments, portions are of about equal length. In some embodiments, portions are not of equal length. In some embodiments, portions are of a first equal length within a certain genomic region of interest, and are of a second equal length within a different genomic region of interest. For example, portions may be 30 kb in length within genomic region A and may be 70 kb in genomic region B. Methods for optimizing portion length within a genomic region of interest are provided herein and described in further detail below. In some embodiments portions of different lengths are adjusted or weighted. In some embodiments, a genome is partitioned according to an initial portion length and then re-partitioned according to one or more optimal portion lengths. In some embodiments, a portion is about 1 kilobase (kb) to about 1000 kb, about 1 kb to about 500 kb, about 10 kb to about 300 kb, about 10 kb to about 100 kb, about 20 kb to about 80 kb, about 30 kb to about 70 kb, about 40 kb to about 60 kb, and sometimes about 50 kb. In some embodiments, a portion is not 50 kb. In some embodiments, a portion is about 10 kb to about 20 kb. In some embodiments, a portion is about 30 kb. In some embodiments, a portion is about 10 kb. In some embodiments, a portion is about 20 kb. In some embodiments, a portion is about 30 kb. In some embodiments, a portion is about 40 kb. In some embodiments, a portion is about 50 kb. In some embodiments, a portion is about 60 kb. In some embodiments, a portion is about 70 kb. In some embodiments, a portion is about 80 kb. In some embodiments, a portion is about 90 kb. In some embodiments, a portion is about 100 kb. In some embodiments, a portion is about 30 kb to about 300 kb. In some embodiments, a portion is about 32 kb. In some embodiments, a portion is about 64 kb. In some embodiments, a portion is about 128 kb. In some embodiments, a portion is about 256 kb. A portion is not limited to contiguous runs of sequence. Thus, portions can be made up of contiguous and/or non-contiguous sequences. A portion is not limited to a single chromosome. In some embodiments, a portion includes all or part of one chromosome or all or part of two or more chromosomes. In some embodiments, portions may span one, two, or more entire chromosomes. In addition, portions may span jointed or disjointed regions of multiple chromosomes.

In some embodiments, portions can be particular chromosome segments in a chromosome of interest, such as, for example, a chromosome where a genetic variation is assessed (e.g. an aneuploidy of chromosomes 13, 18 and/or 21 or a sex chromosome). A portion can also be a pathogenic genome (e.g. bacterial, fungal or viral) or fragment thereof. Portions can be genes, gene fragments, regulatory sequences, introns, exons, and the like.

A "segment" of a chromosome generally is part of a chromosome, and typically is a different part of a chromosome than a portion. A segment of a chromosome sometimes is in a different region of a chromosome than a portion, sometimes does not share a polynucleotide with a portion, and sometimes includes a polynucleotide that is in a portion. A segment of a chromosome often contains a larger number of nucleotides than a portion (e.g., a segment sometimes includes a portion), and sometimes a segment of a chromosome contains a smaller number of nucleotides than a portion (e.g., a segment sometimes is within a portion). A "genomic region," as used herein, often contains a larger number of nucleotides than a portion (e.g., a genomic region sometimes includes a portion or a plurality of portions).

Genome Partitioning

In some embodiments, a genome (e.g. human genome, reference genome, part of a reference genome, genomic region, one or more chromosomes, segment of a chromosome) is partitioned into portions based on information content of particular regions and/or other parameters. Genome partitioning sometimes is referred to as discretization, binning, segmenting, segmentation, portioning, dividing, grouping, aggregating, and aggregation. In some embodiments, a genome is partitioned according to guanine and cytosine (GC) content. In some embodiments, a genome is partitioned according to sequencing coverage variability. In some embodiments, partitioning a genome may eliminate or reduce biases associated with information content of particular regions and/or other parameters. In some embodiments, partitioning a genome may establish a fine grid (i.e., small portions) for certain regions and a coarse grid (i.e., large portions) for other regions. In some embodiments, partitioning a genome may eliminate similar regions (e.g., identical or homologous regions or sequences) across the genome and only keep unique regions. Regions removed during partitioning may be within a single chromosome or may span multiple chromosomes. In some embodiments a partitioned genome is trimmed down and optimized for faster alignment, often allowing for focus on uniquely identifiable sequences.

In some embodiments, partitioning of a genome into regions transcending chromosomes may be based on information gain produced in the context of classification. For example, information content may be quantified using a p-value profile measuring the significance of particular genomic locations for distinguishing between groups of confirmed normal and abnormal subjects (e.g. euploid and trisomy subjects, respectively). In some embodiments, partitioning of a genome into regions transcending chromosomes may be based on any other criterion, such as, for example, speed/convenience while aligning tags, GC content (e.g., high or low GC content), uniformity of GC content, other measures of sequence content (e.g. fraction of individual nucleotides, fraction of pyrimidines or purines, fraction of natural vs. non-natural nucleic acids, fraction of methylated nucleotides, and CpG content), sequencing coverage variability, methylation state, duplex melting temperature, amenability to sequencing or PCR, uncertainty value assigned to individual portions of a reference genome, and/or a targeted search for particular features. Provided herein, for example, are methods for partitioning a genome according to GC content. Also provided herein, for example, are methods for partitioning a genome according to sequencing coverage variability.

GC Partitioning

In some embodiments, a genome is partitioned according to guanine and cytosine (GC) content. GC partitioning sometimes is referred to herein as "wavelet binning." Often, each chromosome, or a portion of each chromosome, is partitioned separately from other chromosomes (i.e., one at a time) in the reference genome. While the method described below is generally applied to a single chromosome, one or more or all chromosomes in a reference genome may be partitioned according to the following method.

In some embodiments, partitioning a genome according to GC content comprises generating a GC profile for a chromosome, or a segment of a chromosome. GC profiles can be generated by quantifying the GC content (i.e., number of guanine and cytosine bases) for a given length of genomic sequence (i.e. window) throughout a chromosome, or part thereof, in a reference genome. Windows generally are relatively short lengths of genomic sequence (e.g., 100 bases to 10 kilobases (kb)). GC content generally is determined for contiguous windows throughout a chromosome or segment thereof. In certain instances, windows are 1 kb. Thus, for example, a GC profile may be generated by quantifying the GC content per 1 kb contiguous window throughout a chromosome in a reference genome.

In some embodiments, partitioning a genome according to GC content comprises segmenting. In some embodiments segmenting modifies and/or transforms a profile (e.g., a GC profile) thereby providing one or more decomposition renderings of a profile. A profile subjected to a segmenting process often is a profile of GC content in a reference genome or part thereof (e.g., autosomes and sex chromosomes). A decomposition rendering of a profile is often a transformation of a profile. A decomposition rendering of a profile is sometimes a transformation of a profile into a representation of a genome, chromosome or segment thereof.

In certain embodiments a segmenting process utilized for the segmenting locates and identifies one or more GC content levels within a profile that are different (e.g., substantially or significantly different) than one or more other GC content levels within a profile. A GC content level identified in a profile according to a segmenting process that is different than another GC content level in the profile, and has edges that are different than another GC content level in the profile, is referred to herein as a wavelet, and more generally as a GC content level for a discrete segment. A segmenting process can generate, from a profile of GC content or GC content levels, a decomposition rendering in which one or more discrete segments or wavelets can be identified. A discrete segment generally is shorter than what is segmented (e.g., chromosome, chromosomes, autosomes).

In some embodiments segmenting locates and identifies edges of discrete segments and wavelets within a profile. In certain embodiments one or both edges of one or more discrete segments and wavelets are identified. For example, a segmentation process can identify the location (e.g., genomic coordinates, e.g., portion location) of the right and/or the left edges of a discrete segment or wavelet in a profile. A discrete segment or wavelet often comprises two edges. For example, a discrete segment or wavelet can include a left edge and a right edge. In some embodiments, depending upon the representation or view, a left edge can be a 5'-edge and a right edge can be a 3'-edge of a nucleic acid segment in a profile. In some embodiments a left edge can be a 3'-edge and a right edge can be a 5'-edge of a nucleic acid segment in a profile. Often the edges of a profile are known prior to segmentation and therefore, in some embodiments, the edges of a profile determine which edge of a level is a 5'-edge and which edge is 3'-edge. In some embodiments one or both edges of a profile and/or discrete segment (e.g., wavelet) is an edge of a chromosome.

In some embodiments the edges of a discrete segment or wavelet are determined according to a decomposition rendering generated for a reference sample (e.g., a reference profile). In some embodiments a null edge height distribution is determined according to a decomposition rendering of a reference profile (e.g., a profile of a chromosome or segment thereof). In certain embodiments, the edges of a discrete segment or wavelet in a profile are identified when the level of the discrete segment or wavelet is outside a null edge height distribution. In some embodiments the edges of a discrete segment or wavelet in a profile are identified according a Z-score calculated according to a decomposition rendering for a reference profile.

Sometimes segmenting generates two or more discrete segments or wavelets (e.g., two or more fragmented levels, two or more fragmented segments) in a profile. In some embodiments a decomposition rendering derived from a segmenting process is over-segmented or fragmented and comprises multiple discrete segments or wavelets. Sometimes discrete segments or wavelets generated by segmenting are substantially different and sometimes discrete segments or wavelets generated by segmenting are substantially similar. Substantially similar discrete segments or wavelets (e.g., substantially similar levels) often refers to two or more adjacent discrete segments or wavelets in a segmented profile each having a GC content level that differs by less than a predetermined level of uncertainty. In some embodiments substantially similar discrete segments or wavelets are adjacent to each other and are not separated by an intervening segment or wavelet. In some embodiments substantially similar discrete segments or wavelets are separated by one or more smaller segments or wavelets. Substantially different discrete segments or wavelets, in some embodiments are not adjacent. Substantially different discrete segments or wavelets generally have substantially different GC content levels.

In some embodiments a segmentation process comprises determining (e.g., calculating) a GC content level (e.g., a quantitative value, e.g., a mean or median level), a level of uncertainty (e.g., an uncertainty value), Z-score, Z-value, p-value, the like or combinations thereof for one or more discrete segments or wavelets (e.g., GC content levels) in a profile or segment thereof. In some embodiments a GC content level (e.g., a quantitative value, e.g., a mean or median level), a level of uncertainty (e.g., an uncertainty value), Z-score, Z-value, p-value, the like or combinations thereof are determined (e.g., calculated) for a discrete segment or wavelet.

In some embodiments, segmenting is accomplished by a process that comprises one process or multiple sub-processes, non-limiting examples of which include a decomposition generating process (e.g., a wavelet decomposition generating process), thresholding, leveling, smoothing, the like or combination thereof. Thresholding, leveling, smoothing and the like can be performed in conjunction with a decomposition generating process, and are described hereafter with reference to a wavelet decomposition rendering process.

In some embodiments, segmenting is performed according to a wavelet decomposition generating process. In some embodiments segmenting is performed according to two or more wavelet decomposition generating processes. In some embodiments a wavelet decomposition generating process identifies one or more wavelets in a profile and provides a decomposition rendering of a profile.

Segmenting can be performed, in full or in part, by any suitable wavelet decomposition generating process described herein or known in the art. Non-limiting examples of a wavelet decomposition generating process include a Haar wavelet segmentation (Haar, Alfred (1910) "Zur Theorie der orthogonalen Funktionensysteme", Mathematische Annalen 69 (3): 331-371; Nason, G. P. (2008) "Wavelet methods in Statistics", R. Springer, New York) (e.g., WaveThresh), Wavethresh, a suitable recursive binary segmentation process, circular binary segmentation (CBS) (Olshen, A B, Venkatraman, E S, Lucito, R, Wgler, M (2004) "Circular binary segmentation for the analysis of array-based DNA copy number data", Biostatistics, 5, 4:557-72; Venkatraman, E S, Olshen, A B (2007) "A faster circular binary segmentation algorithm for the analysis of array CGH data", Bioinformatics, 23, 6:657-63), Maximal Overlap Discrete Wavelet Transform (MODWT) (L. Hsu, S. Self, D. Grove, T. Randolph, K. Wang, J. Delrow, L. Loo, and P. Porter, "Denoising array-based comparative genomic hybridization data using wavelets", Biostatistics (Oxford, England), vol. 6, no. 2, pp. 211-226, 2005), stationary wavelet (SWT) (Y. Wang and S. Wang, "A novel stationary wavelet denoising algorithm for array-based DNA copy number data", International Journal of Bioinformatics Research and Applications, vol. 3, no. 2, pp. 206-222, 2007), dual-tree complex wavelet transform (DTCWT) (Nha, N., H. Heng, S. Oraintara and W. Yuhang (2007) "Denoising of Array-Based DNA Copy Number Data Using The Dual-tree Complex Wavelet Transform." 137-144), convolution with edge detection kernel, Jensen Shannon Divergence, Kullback-Leibler divergence, Binary Recursive Segmentation, a Fourier transform, the like or combinations thereof.

A wavelet decomposition generating process can be represented or performed by a suitable software, module and/or code written in a suitable language (e.g., a computer programming language known in the art) and/or operating system, non-limiting examples of which include UNIX, Linux, oracle, windows, Ubuntu, ActionScript, C, C++, C#, Haskell, Java, JavaScript, Objective-C, Perl, Python, Ruby, Smalltalk, SQL, Visual Basic, COBOL, Fortran, UML, HTML (e.g., with PHP), PGP, G, R, S, the like or combinations thereof. In some embodiments a suitable wavelet decomposition generating process is represented in S or R code or by a package (e.g., an R package). R, R source code, R programs, R packages and R documentation for wavelet decomposition generating processes are available for download from a CRAN or CRAN mirror site (e.g., The Comprehensive R Archive Network (CRAN); World Wide Web URL cran.us.r-project.org). CRAN is a network of ftp and web servers around the world that store identical, up-to-date, versions of code and documentation for R. For example, WaveThresh (WaveThresh: Wavelets statistics and transforms; World Wide Web URL cran.r-project.org/web/packages/wavethresh/index.html) and a detailed description of WaveThresh (Package 'wavethresh'; World Wide Web URL cran.r-project.org/web/packages/wavethresh/wavethresh.pdf) can be available for download. An example of R code for a CBS method can be downloaded (e.g., DNAcopy; World Wide Web URL bioconductor.org/packages/2.12/bioc/html/DNAcopy.html or Package 'DNAcopy'; World Wide Web URL bioconductor.org/packages/release/bioc/manuals/DNAcopy/man/DNAcopy.pdf).

In some embodiments a wavelet decomposition generating process (e.g., a Haar wavelet segmentation, e.g., WaveThresh) comprises thresholding. In some embodiments thresholding distinguishes signals from noise. In certain embodiments thresholding determines which wavelet coefficients (e.g., nodes) are indicative of signals and should be retained and which wavelet coefficients are indicative of a reflection of noise and should be removed. In some embodiments thresholding comprises one or more variable parameters where a user sets the value of the parameter. In some embodiments thresholding parameters (e.g., a thresholding parameter, a policy parameter) can describe or define the amount of segmentation utilized in a wavelet decomposition generating process. Any suitable parameter values can be used. In some embodiments a thresholding parameter is used. In some embodiments a thresholding parameter value is a soft thresholding. In certain embodiments a soft thresholding is utilized to remove small and non-significant coefficients. In certain embodiments a hard thresholding is utilized. In certain embodiments a thresholding comprises a policy parameter. Any suitable policy value can be used. In some embodiments a policy used is "universal" and in some embodiments a policy used is "sure".

In some embodiments, a wavelet decomposition generating process (e.g., a Haar wavelet segmentation, e.g., WaveThresh) comprises leveling. In some embodiments, after thresholding, some high level coefficients remain. These coefficients represent steep changes or large spikes in the original signal and, in certain embodiments, are removed by leveling. In some embodiments leveling includes assignment of a value to a parameter known as a decomposition level c. In certain embodiments an optimal decomposition level is determined according to one or more determined values, such as the length of the chromosome (e.g., length of profile), the desired wavelet length to detect, fetal fraction, sequence coverage (e.g., plex level) and the noise level of a normalized profile. For a given length of a segment of a genome, chromosome or profile ($L_{chr}$), the wavelet decomposition level c is sometimes related to the minimum wavelet length or minimum portion length $L_{min}$ according to the equation $L_{min}=L_{chr}/2^{c+1}$. In some embodiments, a decomposition level c is determined according to one of the following equations: $c=\log_2(L_{chr}/L_{min})$; $c=\log_2(L_{chr}/L_{min})+1$; $c=\log_2(L_{chr}/L_{min})-1$. In some embodiments, a decomposition level c is about 1, 2, 3, 4, 5, 6, 7, 8, 9 or 10. In some embodiments $L_{min}$ is predetermined. In some embodiments $L_{min}$ is predetermined according to a limit of detection (LoD) analysis, as described in Example 1. In some embodiments the amount of sequence coverage (e.g., plex level) and fetal fraction are inversely proportional to $L_{min}$. For example, the minimum desired wavelet length (e.g., minimum portion length) decreases (i.e. resolution increases) as the amount of fetal fraction in a sample increases. In some embodiments the minimum desired wavelet length (e.g., minimum portion length) decreases (i.e. resolution increases) as the sequencing coverage increases. In some embodiments thresholding is performed prior to leveling and sometimes thresholding is performed after leveling.

In some embodiments, a decomposition rendering is polished thereby providing a polished decomposition rendering. In some embodiments a decomposition rendering is polished two or more times. In some embodiments a decomposition rendering is polished before and/or after one or more steps of a segmenting process. In some embodiments genome partitioning comprises two or more segmenting processes and each segmenting process comprises one or more polishing processes. A decomposition rendering can refer to a polished decomposition rendering or a decomposition rendering that is not polished.

Thus, in some embodiments a segmenting process comprises polishing. In some embodiments a polishing process identifies two or more substantially similar discrete segments or wavelets (e.g., in a decomposition rendering) and merges them into a single discrete segment or wavelet. In some embodiments a polishing process identifies two or more adjacent segments or wavelets that are substantially similar and merges them into a single level, segment or wavelet. Thus, in some embodiments a polishing process comprises a merging process. In certain embodiments adjacent fragmented discrete segments or wavelets are merged according to their GC content levels. In some embodiments merging two or more adjacent discrete segments or wavelets comprises calculating a median level for the two or more adjacent discrete segments or wavelets that are eventually merged. In some embodiments, two or more adjacent discrete segments or wavelets that are substantially similar are merged and thereby polished resulting in a single segment, wavelet or GC content level. In certain embodiments, two or more adjacent discrete segments or wavelets are merged by a process described by Willenbrock and Fridly (Willenbrock H, Fridlyand J. A comparison study: applying segmentation to array CGH data for downstream analyses. *Bioinformatics*

2005 Nov. 15; 21(22):4084-91). In some embodiments two or more adjacent discrete segments or wavelets are merged by a process known as GLAD and described in Hupe, P. et al. (2004) "Analysis of array CGH data: from signal ratio to gain and loss of DNA regions", Bioinformatics, 20, 3413-3422.

In some embodiments, a segmenting process comprises a "sliding edges" or "sliding window" process. A suitable "sliding edges" process can be used directly or can be adapted for validating a discrete segment in a decomposition rendering. In some embodiments, a "sliding edges" process comprises segmenting a discrete segment into multiple subsets of portions. In some embodiments, the discrete segment is a set of portions for a whole chromosome or a segment of a chromosome.

In certain embodiments a "sliding edges" process comprises segmenting an identified discrete segment into multiple subsets of portions where each of the subsets of portions represents a discrete segment with similar, but different edges. In some embodiments the originally identified discrete segment is included in the analysis. For example, the originally identified discrete segment is included as one of the multiple subsets of portions. The subsets of portions can be determined by varying one or both edges of the originally identified discrete segment by any suitable method. In some embodiments the left edge can be changed thereby generating discrete segments with different left edges. In some embodiments the right edge can be changed thereby generating discrete segments with different right edges. In some embodiments both the right and left edges can be changed. In some embodiments the edges are changed by moving the edge by one or more adjacent portions of a reference genome to the left or to the right of the original edges.

In some embodiments either one or both edges are changed by 5 to 30 portions of a reference genome. In some embodiments an edge is moved by 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 portions of a reference genome in either direction. In some embodiments, regardless of the portion size, an edge is changed to generate an edge range of about 100,000 to about 2,000,000 base pairs, 250,000 to about 1,500,000 base pairs, or about 500,000 to about 1,000,000 base pairs for either or both edges. In some embodiments, regardless of the portion size, an edge is changed to generate an edge range of about 500,000, 600,000, 700,000, 750,000, 800,000, 900,000, or about 1,000,000 bases pairs for either or both edges.

In some embodiments an identified discrete segment comprises a first end and a second end and the segmenting comprises (i) removing one or more portions from the first end of the set of portions by recursive removal thereby providing a subset of portions with each recursive removal, (ii) terminating the recursive removal in (i) after n repeats thereby providing n+1 subsets of portions, where the set of portions is a subset, and where each subset comprises a different number of portions, a first subset end and a second subset end, (iii) removing one or more portions from the second subset end of each of the n+1 subsets of portions provided in (ii) by recursive removal; and (iv) terminating the recursive removal in (iii) after n repeats, thereby providing multiple subsets of portions. In some embodiments the multiple subsets equals (n+1)2 subsets. In some embodiments n is equal to an integer between 5 and 30. In some embodiments n is equal to 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In certain embodiments of a sliding edges approach, a level of significance (e.g., a Z-score, a p-value) is determined for each of the subsets of portions of a reference genome and an average, mean or median level of significance is determined according to the level of significance determined for all of the subsets.

In some embodiments the level of significance is a Z-score or a p-value. In some embodiments a Z-score is calculated according to the following formula:

$$Z_i = (E_i - \text{Med.E}_{(n)}) / \text{MAD}$$

where $E_i$ is a quantitative determination of the level of the discrete segment i, $\text{Med.E}_{(n)}$ is the median level for all discrete segments generated by a sliding edges process and MAD is the median absolute deviation for $\text{Med.E}_{(n)}$, and $Z_i$ is the resulting Z-score for discrete segment i. In some embodiments MAD can be replaced by any suitable measure of uncertainty. In some embodiments $E_i$ is any suitable measure of a level, non-limiting examples of which include a median level, average level, mean level, sum of the counts for the portions, or the like.

In some embodiments, a segmenting process as described above is applied to a GC profile to provide discrete segments. A segmenting process can be performed on the GC content levels, as described herein. In certain instances, windows having similar GC content levels are merged into the discrete segments during the segmenting process. In certain embodiments, a segmenting process generates a decomposition rendering comprising the discrete segments. In certain embodiments, a chromosome is partitioned into a plurality of portions according to the discrete segments. Thus, in certain embodiments, the location and length of the discrete segments are the same or are similar to the location and length of the portions in a GC partitioned chromosome.

Sequencing Coverage Variability Partitioning

In some embodiments, a genome is partitioned according to sequencing coverage variability. In certain instances, sequencing of nucleic acid comprising a mixture of maternal and fetal genetic material (e.g., ccfDNA) can be characterized by variations in sequencing coverage as a function of genomic location. Without being limited by theory, certain genomic regions may provide a wealth of sequencing data while other regions may provide sparse sequencing data. Optimizing the portion length for certain regions in view of sequencing coverage variability may allow for use of a fine grid (i.e., small portions) for certain regions and a coarse grid (i.e., large portions) for other regions. A fine grid may be useful, for example, for detection of small genetic variations (e.g., small microdeletions or microduplications). A coarse grid may be useful, for example, for capturing sequence read data that otherwise may be filtered out using a smaller or standard grid.

In some embodiments, genome partitioning comprises determining sequencing coverage variability across a reference genome. In some embodiments, a training set of nucleotide sequence reads mapped to portions of a reference genome is used for determining sequencing coverage variability. A training set may include, for example, nucleotide sequence reads from a plurality of samples comprising a mixture of maternal and fetal ccf nucleic acid (e.g., ccfDNA). Sequencing coverage variability across a reference genome can be determined by the quantification of sequence reads for the training set. Quantification of sequence reads may include quantification of raw sequence reads and/or quantification of normalized sequence reads for one or more portions or regions as described herein. In certain instances, an average sequence read count is determined. In certain instances, an average normalized sequence read count is determined.

In some embodiments, genome partitioning comprises selecting an initial portion length. Initial portion length can be selected, for example, according to certain features of the training set. For example, initial portion length can be selected according to sequencing depth for the training set. In certain instances, initial portion length can be selected according to an average fetal fraction for the training set. In some embodiments, the initial portion length is selected according to sequencing depth and average fetal fraction for the training set. Average fetal fraction for the training set can be determined using any suitable method for determining fetal fraction known in the art or described herein (e.g., portion-specific fetal fraction determination). In some embodiments, average fetal fraction for the training set is known or can be calculated based on sample records. Initial portion length can be between about 1 kb to about 1000 kb. In some embodiments, initial portion length is about 10 kb. In some embodiments, initial portion length is about 20 kb. In some embodiments, initial portion length is about 30 kb. In some embodiments, initial portion length is about 40 kb. In some embodiments, initial portion length is about 50 kb. In some embodiments, initial portion length is about 60 kb. In some embodiments, initial portion length is about 70 kb. In some embodiments, initial portion length is about 80 kb. In some embodiments, initial portion length is about 90 kb. In some embodiments, initial portion length is about 100 kb. In some embodiments, initial portion length is not 50 kb. Generally, a larger initial portion length (e.g., larger than 50 kb) may be selected for a training set with a low average fetal fraction (e.g., less than 10%) and/or low sequencing depth, and a smaller initial portion length (e.g., shorter than 50 kb) may be selected for a training set with a high average fetal fraction (e.g., 10% to 20%) and/or high sequencing depth. In some embodiments, a total number of portions for a reference genome can be determined according to the initial portion length and total genome size.

In some embodiments, genome partitioning comprises partitioning at least two genomic regions according to initial portion size. A genomic region may be selected according to one or more known genetic variations (e.g., any form of copy number variation) that may exist within the region (e.g., microdeletions, microduplications, aneuploidies), or may be selected at random. A genomic region may be a chromosome or a segment of a chromosome. Generally, pairs of genomic regions are selected for a comparison of sequencing coverage variability, as described below. Additional pairings of genomic regions can be selected as needed. A first pair of genomic regions may comprise a first genomic region and a second genomic region. Often, the first genomic region and the second genomic are substantially similar or equal in size (i.e. length). For example, a first genomic region and a second genomic may differ in length by about 1 kb or less.

In some embodiments, genome partitioning comprises comparing sequencing coverage variability for each pair of genomic regions. Comparing sequencing coverage variability may comprise calculating a proportionality factor (P) according to the following equation:

$$P = (var_1/var_2)^{1/3} \quad\quad\quad \text{equation A}$$

where $var_1$ is the sequencing coverage variability of the first genomic region and $var_2$ is the sequencing coverage variability of the second genomic region. In some embodiments, sequencing coverage variability of a first genomic region is determined from a nucleotide sequence read count, or a derivative thereof, for the first genomic region, and sequencing coverage variability of a second genomic region is determined from a nucleotide sequence read count, or a derivative thereof, for the second genomic region. As used herein, a derivative of a sequence read count may be a processed sequence read count (e.g., filtered, adjusted, and/or normalized sequence read count, as described herein). In some embodiments, sequencing coverage variability of a first genomic region is determined from an average nucleotide sequence read count, or a derivative thereof, for the first genomic region, and sequencing coverage variability of a second genomic region is determined from an average nucleotide sequence read count, or a derivative thereof, for the second genomic region. In some embodiments, average nucleotide sequencing read counts for each genomic region are determined using the training set. In some embodiments, nucleotide sequence read count is a normalized nucleotide sequence read count. In some embodiments, average nucleotide sequence read count is an average normalized nucleotide sequence read count.

In some embodiments, genome partitioning comprises recalculating the number of portions for a genomic region. Recalculating the number of portions for a genomic region typically is according to the comparison of sequence coverage variability described above. In certain instances, recalculating the number of portions for a genomic region is according to a proportionality factor (e.g., the proportionality factor described above). In some embodiments, recalculating the number of portions for a genomic region is performed according to a proportionality factor and a total number of portions (e.g., for a reference genome) determined from the initial portion size, as described above. For example, let N1 be the number of portions for a genomic region 1, let N2 be the number of portions for a genomic region 2, and let N3 be the number of portions for a genomic region 3. Let N be the total number of regions and the ratios between these numbers (derived from equation A above) as follows:

$$N1/N2 = P1$$

$$N1/N3 = P2$$

Then, $$N1+N2+N3 = N$$

And given how $N2=N1/P1$ and $N3=N1/P2$ it follows that $$N1 = N*P1*P2/(P1*P2+P1+P2),$$

$$N2 = N*P2/(P1*P2+P1+P2), \text{ and}$$

$$N3 = N*P1/(P1*P2+P1+P2).$$

In some embodiments, genome partitioning comprises determining an optimized portion length for a genomic region according to the recalculated number of portions. An optimized portion length can be between about 1 kilobase (kb) to about 1000 kb. In some embodiments, an optimized portion length is between about 1 kb to about 500 kb, between about 10 kb to about 300 kb, between about 10 kb to about 100 kb, between about 20 kb to about 80 kb, between about 30 kb to about 70 kb, or between about 40 kb to about 60 kb. In some embodiments, an optimized portion length is not 50 kb. In some embodiments, an optimized portion length is about 10 kb to about 20 kb. In some embodiments, an optimized portion length is about 30 kb. In some embodiments, an optimized portion length is about 10 kb. In some embodiments, an optimized portion length is about 20 kb. In some embodiments, an optimized portion length is about 30 kb. In some embodiments, an optimized portion length is about 40 kb. In some embodiments, an optimized portion length is about 50 kb. In some embodiments, an optimized portion length is about 60 kb. In some embodiments, an optimized portion length is about 70 kb. In some embodiments, an optimized portion length is about 80 kb. In some embodiments, an optimized portion length is about 90 kb. In some embodiments, an optimized portion length is about 100 kb.

In some embodiments, genome partitioning comprises re-partitioning a genomic region into a plurality of portions according to an optimized portion size. In some embodiments, a plurality of portions comprises portions of constant (i.e., equal or substantially equal) length. In some embodiments, a plurality of portions comprises portions of varying size. In certain instances, a genome partitioning method may comprise additional methods of genome partitioning (e.g., GC partitioning described herein) in conjunction, which may provide portions of varying size. In some embodiments, genome partitioning comprises re-partitioning one or more additional genomic regions of a reference genome using a method described herein. In some embodiments, genome partitioning comprises re-partitioning all or substantially all of the genomic regions of a reference genome using a method described herein.

In some embodiments, genome partitioning comprises estimating fetal fraction for a test sample. Fetal fraction can be estimated using any suitable method for estimating fetal fraction known in the art or described herein (e.g., portion-specific fetal fraction estimation, fetal quantifier assay, SNP-based fetal fraction estimation, Y chromosome fetal fraction estimation). Estimating fetal fraction sometimes comprises determining an error value. An error value may be expressed as (or represent), for example, an uncertainty value, a calculated variance, standard deviation, Z-score, p-value, mean absolute deviation, average absolute deviation, median absolute deviation, and the like. In some embodiments an error value defines a range above and below an estimated fetal fraction. In some embodiment, error is expressed as a range of values (e.g., confidence interval). In some embodiments, a region-specific fetal fraction is determined for a genomic region according to a correlation between nucleotide sequence read counts (e.g., raw sequence read counts, normalized sequence read counts) per portion and a weighting factor (e.g., portion-specific fetal fraction determination, as described herein).

In some embodiments, genome partitioning comprises determining a minimum genomic region size (i.e., length). In some embodiments, genome partitioning comprises determining a minimum genomic region size that is detectable for a sample having a given fetal fraction (e.g., as estimated according to a method described above). In certain instances, a minimum genomic region size is determined according to a limit of detection (LoD) analysis, as described in Example 1, and as provided in FIG. 7 for certain genetic abnormalities. In certain instances, a minimum genomic region size is determined according to a particular confidence interval of fetal fraction. For example, a minimum genomic region size can be determined according to an upper 80% confidence interval of fetal fraction. In certain embodiments, a minimum genomic region size can be determined according to an upper 90% confidence interval of fetal fraction. In certain embodiments, a minimum genomic region size can be determined according to an upper 95% confidence interval of fetal fraction. In certain embodiments, a minimum genomic region size can be determined according to an upper 99% confidence interval of fetal fraction.

In some embodiments, genome partitioning comprises determining a local minimum genomic region size (i.e., length). "Local" refers to within a particular genomic region being repartitioned. In some embodiments, genome partitioning comprises determining a local genomic region size that is detectable for a sample having an average fetal fraction. An average fetal fraction may be between about 5% to about 20%. For example, an average fetal fraction may be about 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, or 19.5%. In certain instances, a local minimum genomic region size is determined according to a limit of detection (LoD) analysis, as described in Example 1, and as provided in FIG. 7 for certain genetic abnormalities.

In some embodiments, genome partitioning comprises determining a local minimum genomic region size (i.e., length). In some embodiments, genome partitioning comprises determining a local minimum genomic region size that is detectable for a sample having a given fetal fraction (e.g., as estimated according to a method described above). In certain instances, a local minimum genomic region size is determined according to a limit of detection (LoD) analysis, as described in Example 1, and as provided in FIG. 7 for certain genetic abnormalities. In certain instances, a local minimum genomic region size is determined according to a particular confidence interval of fetal fraction. For example, a local minimum genomic region size can be determined according to an upper 80% confidence interval of fetal fraction. In certain embodiments, a local minimum genomic region size can be determined according to an upper 90% confidence interval of fetal fraction. In certain embodiments, a local minimum genomic region size can be determined according to an upper 95% confidence interval of fetal fraction. In certain embodiments, a local minimum genomic region size can be determined according to an upper 99% confidence interval of fetal fraction.

In certain instances, a minimum genomic region size or a local minimum genomic region size may span a single portion. To address this possibility, genome partitioning may further comprise adjusting the number of portions for each genomic region such that each region comprises at least two portions. Adjusting the number of portions for each genomic region can generate a refined grid (i.e., refined repartitioned genome).

In some embodiments, genome partitioning comprises re-estimating fetal fraction from the refined re-partitioned genomic region. In some embodiments, a re-estimated fetal fraction is compared to an initial fetal fraction estimate for a sample. In some embodiments, a re-estimated fetal fraction is compared to a region-specific fetal fraction estimate. In some embodiments, certain method components are repeated when an initial estimated fetal fraction or region-specific fetal fraction differs from a re-estimated fetal fraction by a predetermined tolerance value. A predetermined tolerance value can be between about 1% to about 25%. For example, a predetermined tolerance value can be about 2%, 3%, 4%, 5%, 6%, 7%, 8%, 9%, 10%, 11%, 12%, 13%, 14%, 15%, 16%, 17%, 18%, 19%, 20%, 21%, 22%, 23% or 24%.

Counts

Sequence reads that are mapped or partitioned based on a selected feature or variable can be quantified to determine the number of reads that are mapped to one or more portions (e.g., portion of a reference genome), in some embodiments.

In certain embodiments the quantity of sequence reads that are mapped to a portion are termed counts (e.g., a count). Often a count is associated with a portion. In certain embodiments counts for two or more portions (e.g., a set of portions) are mathematically manipulated (e.g., averaged, added, normalized, the like or a combination thereof). In some embodiments a count is determined from some or all of the sequence reads mapped to (i.e., associated with) a portion. In certain embodiments, a count is determined from a pre-defined subset of mapped sequence reads. Pre-defined subsets of mapped sequence reads can be defined or selected utilizing any suitable feature or variable. In some embodiments, pre-defined subsets of mapped sequence reads can include from 1 to n sequence reads, where n represents a number equal to the sum of all sequence reads generated from a test subject or reference subject sample.

In certain embodiments a count is derived from sequence reads that are processed or manipulated by a suitable method, operation or mathematical process known in the art. A count (e.g., counts) can be determined by a suitable method, operation or mathematical process. In certain embodiments a count is derived from sequence reads associated with a portion where some or all of the sequence reads are weighted, removed, filtered, normalized, adjusted, averaged, derived as a mean, added, or subtracted or processed by a combination thereof. In some embodiments, a count is derived from raw sequence reads and or filtered sequence reads. In certain embodiments a count value is determined by a mathematical process. In certain embodiments a count value is an average, mean or sum of sequence reads mapped to a portion. Often a count is a mean number of counts. In some embodiments, a count is associated with an uncertainty value.

In some embodiments, counts can be manipulated or transformed (e.g., normalized, combined, added, filtered, selected, averaged, derived as a mean, the like, or a combination thereof). In some embodiments, counts can be transformed to produce normalized counts. Counts can be processed (e.g., normalized) by a method known in the art and/or as described herein (e.g., portion-wise normalization, median count (median bin count, median portion count) normalization, normalization by GC content, linear and nonlinear least squares regression, LOESS (e.g., GC LOESS), LOWESS, ChAI, principal component normalization, RM, GCRM, cQn and/or combinations thereof). In certain embodiments, counts can be processed (e.g., normalized) by one or more of LOESS, median count (median bin count, median portion count) normalization, and principal component normalization. In certain embodiments, counts can be processed (e.g., normalized) by LOESS followed by median count (median bin count, median portion count) normalization. In certain embodiments, counts can be processed (e.g., normalized) by LOESS followed by median count (median bin count, median portion count) normalization followed by principal component normalization.

Counts (e.g., raw, filtered and/or normalized counts) can be processed and normalized to one or more levels. Levels and profiles are described in greater detail hereafter. In certain embodiments counts can be processed and/or normalized to a reference level. Reference levels are addressed later herein. Counts processed according to a level (e.g., processed counts) can be associated with an uncertainty value (e.g., a calculated variance, an error, standard deviation, Z-score, p-value, mean absolute deviation, etc.). In some embodiments an uncertainty value defines a range above and below a level. A value for deviation can be used in place of an uncertainty value, and non-limiting examples of measures of deviation include standard deviation, average absolute deviation, median absolute deviation, standard score (e.g., Z-score, Z-score, normal score, standardized variable) and the like.

Counts are often obtained from a nucleic acid sample from a pregnant female bearing a fetus. Counts of nucleic acid sequence reads mapped to one or more portions often are counts representative of both the fetus and the mother of the fetus (e.g., a pregnant female subject). In certain embodiments some of the counts mapped to a portion are from a fetal genome and some of the counts mapped to the same portion are from a maternal genome.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments. In some embodiments one or more or all processing methods (e.g., normalization methods, portion filtering, mapping, validation, the like or combinations thereof) are performed by a processor, a microprocessor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative portions of a reference genome", and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g. a copy number variation, an aneuploidy, a microduplication, a microdeletion, a chromosomal aberration, and the like). In certain embodiments a threshold is exceeded by results obtained by methods described herein and a subject is diagnosed with a genetic variation (e.g. trisomy 21). A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, one or more processing steps can comprise one or more filtering steps. The term "filtering" as used herein refers to removing portions or portions of a reference genome from consideration. Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or segment of a chromosome by a predetermined multiple of the profile variance, and in certain embodiments, a filtering process comprises removing data points from a data set that do not deviate from the mean profile level of a portion, a chromosome or segment of a chromosome by a predetermined multiple of the profile variance. In some embodiments, a filtering process is utilized to reduce the number of candidate portions of a reference genome analyzed for the presence or absence of a genetic variation. Reducing the number of candidate portions of a reference genome analyzed for the presence or absence of a genetic variation (e.g., micro-deletion, micro-duplication) often reduces the complexity and/or dimensionality of a data set, and sometimes increases the speed of searching for and/or identifying genetic variations and/or genetic aberrations by two or more orders of magnitude.

In some embodiments one or more processing steps can comprise one or more normalization steps. Normalization can be performed by a suitable method described herein or known in the art. In certain embodiments normalization comprises adjusting values measured on different scales to a notionally common scale. In certain embodiments normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), ChAI, principal component normalization, repeat masking (RM), GC-normalization and repeat masking (GCRM), cQn and/or combinations thereof. In some embodiments, the determination of a presence or absence of a genetic variation (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), ChAI, principal component normalization, repeat masking (RM), GC-normalization and repeat masking (GCRM), cQn, a normalization method known in the art and/or a combination thereof). In some embodiments, the determination of a presence or absence of a genetic variation (e.g., an aneuploidy, a microduplication, a microdeletion) utilizes one or more of LOESS, median count (median bin count, median portion count) normalization, and principal component normalization. In some embodiments, the determination of a presence or absence of a genetic variation utilizes LOESS followed by median count (median bin count, median portion count) normalization. In some embodiments, the determination of a presence or absence of a genetic variation utilizes LOESS followed by median count (median bin count, median portion count) normalization followed by principal component normalization.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization".

In certain embodiments, a processing step comprising normalization includes normalizing to a static window, and in some embodiments, a processing step comprising normalization includes normalizing to a moving or sliding window. The term "window" as used herein refers to one or more portions chosen for analysis, and sometimes used as a reference for comparison (e.g., used for normalization and/ or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate genetic surrounding, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of micro-deletions and/or micro-insertions. In certain embodiments, displaying cumulative sums of one or more portions is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

Described in greater detail hereafter are certain examples of normalization processes that can be utilized, such as LOESS, ChAI and principal component normalization methods, for example.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with under represented or low quality sequence data can be "down weighted" to minimize the influence on a data set, whereas selected portions of a reference genome can be "up weighted" to increase the influence on a data set. A non-limiting example of a weighting function is $[1/(\text{standard deviation})^2]$. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

After data sets have been counted, optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

In some embodiments portions may be filtered according to a measure of error (e.g., standard deviation, standard error, calculated variance, p-value, mean absolute error (MAE), average absolute deviation and/or mean absolute deviation (MAD). In certain embodiments a measure of error refers to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments portions with a count variability above a pre-determined upper range are filtered (e.g., excluded from consideration). In some embodiments a pre-determined upper range is a MAD value equal to or greater than about 50, about 52, about 54, about 56, about 58, about 60, about 62, about 64, about 66, about 68, about 70, about 72, about 74 or equal to or greater than about 76. In some embodiments portions with a count variability below a pre-determined lower range are filtered (e.g., excluded from consideration). In some embodiments a pre-determined lower range is a MAD value equal to or less than about 40, about 35, about 30, about 25, about 20, about 15, about 10, about 5, about 1, or equal to or less than about 0. In some embodiments portions with a count variability outside a pre-determined range are filtered (e.g., excluded from consideration). In some embodiments a pre-determined range is a MAD value greater than zero and less than about 76, less than about 74, less than about 73, less than about 72, less than about 71, less than about 70, less than about 69, less than about 68, less than about 67, less than about 66, less than about 65, less than about 64, less than about 62, less than about 60, less than about 58, less than about 56, less than about 54, less than about 52 or less than about 50. In some embodiments a pre-determined range is a MAD value greater than zero and less than about 67.7. In some embodiments portions with a count variability within a pre-determined range are selected (e.g., used for determining the presence or absence of a genetic variation).

In some embodiments the count variability of portions represents a distribution (e.g., a normal distribution). In some embodiments portions are selected within a quantile of the distribution. In some embodiments portions within a quantile equal to or less than about 99.9%, 99.8%, 99.7%, 99.6%, 99.5%, 99.4%, 99.3%, 99.2%, 99.1%, 99.0%, 98.9%, 98.8%, 98.7%, 98.6%, 98.5%, 98.4%, 98.3%, 98.2%, 98.1%, 98.0%, 97%, 96%, 95%, 94%, 93%, 92%, 91%, 90%, 85%, 80%, or equal to or less than a quantile of about 75% for the distribution are selected. In some embodiments portions within a 99% quantile of the distribution of count variability are selected. In some embodiments portions with a MAD>0 and a MAD<67.725 a within the 99% quantile and are selected, resulting in the identification of a set of stable portions of a reference genome.

Portions may be filtered based on, or based on part on, a measure of error. A measure of error comprising absolute values of deviation, such as an R-factor, can be used for portion removal or weighting in certain embodiments. An R-factor, in some embodiments, is defined as the sum of the absolute deviations of the predicted count values from the actual measurements divided by the predicted count values from the actual measurements (e.g., Equation II herein). While a measure of error comprising absolute values of deviation may be used, a suitable measure of error may be alternatively employed. In certain embodiments, a measure of error not comprising absolute values of deviation, such as a dispersion based on squares, may be utilized. In some embodiments, portions are filtered or weighted according to a measure of mappability (e.g., a mappability score). A portion sometimes is filtered or weighted according to a relatively low number of sequence reads mapped to the portion (e.g., 0, 1, 2, 3, 4, 5 reads mapped to the portion). Portions can be filtered or weighted according to the type of analysis being performed. For example, for chromosome 13, 18 and/or 21 aneuploidy analysis, sex chromosomes may be filtered, and only autosomes, or a subset of autosomes, may be analyzed.

In particular embodiments, the following filtering process may be employed. The same set of portions (e.g., portions of a reference genome) within a given chromosome (e.g., chromosome 21) is selected and the number of reads in affected and unaffected samples are compared. The gap relates trisomy 21 and euploid samples and it involves a set of portions covering most of chromosome 21. The set of portions is the same between euploid and T21 samples. The distinction between a set of portions and a single section is not crucial, as a portion can be defined. The same genomic region is compared in different patients. This process can be utilized for a trisomy analysis, such as for T13 or T18 in addition to, or instead of, T21.

After data sets have been counted, optionally filtered and normalized, the processed data sets can be manipulated by weighting, in some embodiments. One or more portions can be selected for weighting to reduce the influence of data (e.g., noisy data, uninformative data) contained in the selected portions, in certain embodiments, and in some embodiments, one or more portions can be selected for weighting to enhance or augment the influence of data (e.g., data with small measured variance) contained in the selected portions. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., $[1/(\text{standard deviation})^2]$). In some embodiments, a profile plot of processed data further manipulated by weighting is generated to facilitate classification and/or providing an outcome. An outcome can be provided based on a profile plot of weighted data Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after genomic section levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

In some embodiments, data sets are processed utilizing one or more peak level analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak level analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak level analysis, peak width analysis, peak edge location analysis, peak lateral tolerances, the like, derivations thereof, or combinations of the foregoing.

In some embodiments, the use of one or more reference samples that are substantially free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected portion or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected portion or sections is expected to vary significantly from the predetermined value for affected genomic locations.

In some embodiments, analysis and processing of data can include the use of one or more assumptions. A suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

LOESS Normalization

LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

ChAI Normalization

Another normalization methodology that can be used to reduce error associated with nucleic acid indicators is referred to herein as ChAI and often makes use of a principal component analysis. In certain embodiments, a principal component analysis includes (a) filtering, according to a read density distribution, portions of a reference genome, thereby providing a read density profile for a test sample comprising read densities of filtered portions, where the read densities comprise sequence reads of circulating cell-free nucleic acid from a test sample from a pregnant female, and the read density distribution is determined for read densities of portions for multiple samples, (b) adjusting the read density profile for the test sample according to one or more principal components, which principal components are obtained from a set of known euploid samples by a principal component analysis, thereby providing a test sample profile comprising adjusted read densities, and (c) comparing the test sample profile to a reference profile, thereby providing a comparison. In some embodiments, a principal component analysis includes (d) determining the presence or absence of a genetic variation for the test sample according to the comparison.

Filtering Portions

In certain embodiments one or more portions (e.g., portions of a genome) are removed from consideration by a filtering process. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions. In some embodiments portions of a reference genome are filtered. In some embodiments portions of a reference genome that are removed by a filtering process are not included in a determination of the presence or absence of a genetic variation (e.g., a chromosome aneuploidy, microduplication, microdeletion). In some embodiments portions associated with read densities (e.g., where a read density is for a portion) are removed by a filtering process and read densities associated with removed portions are not included in a determination of the presence or absence of a genetic variation (e.g., a chromosome aneuploidy, microduplication, microdeletion). In some embodiments a read density profile comprises and/or consist of read densities of filtered portions. Portions can be selected, filtered, and/or removed from consideration using any suitable criteria and/or method known in the art or described herein. Non-limiting examples of criteria used for filtering portions include redundant data (e.g., redundant or overlapping mapped reads), non-informative data (e.g., portions of a reference genome with zero mapped counts), portions of a reference genome with over represented or under represented sequences, GC content, noisy data, mappability, counts, count variability, read density, variability of read density, a measure of uncertainty, a repeatability measure, the like, or combinations of the foregoing. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples is sometimes referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. A predetermined threshold is indicated by the dashed vertical lines enclosing a range of acceptable MAD values. In certain instances, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a pre-determined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

In some embodiments a system comprises a filtering module. A filtering module often accepts, retrieves and/or stores portions (e.g., portions of pre-determined sizes and/or overlap, portion locations within a reference genome) and read densities associated with portions, often from another suitable module. In some embodiments selected portions (e.g., filtered portions) are provided by a filtering module. In some embodiments, a filtering module is required to provide filtered portions and/or to remove portions from consideration. In certain embodiments a filtering module removes read densities from consideration where read densities are associated with removed portions. A filtering module often provides selected portions (e.g., filtered portions) to another suitable module.

Bias Estimates

Sequencing technologies can be vulnerable to multiple sources of bias. Sometimes sequencing bias is a local bias (e.g., a local genome bias). Local bias often is manifested at the level of a sequence read. A local genome bias can be any suitable local bias. Non-limiting examples of a local bias include sequence bias (e.g., GC bias, AT bias, and the like), bias correlated with DNase I sensitivity, entropy, repetitive sequence bias, chromatin structure bias, polymerase error-rate bias, palindrome bias, inverted repeat bias, PCR related bias, the like or combinations thereof. In some embodiments the source of a local bias is not determined or known.

In some embodiments a local genome bias estimate is determined. A local genome bias estimate is sometimes referred to herein as a local genome bias estimation. A local genome bias estimate can be determined for a reference genome, a segment or a portion thereof. In some embodiments a local genome bias estimate is determined for one or more sequence reads (e.g., some or all sequence reads of a sample). A local genome bias estimate is often determined for a sequence read according to a local genome bias estimation for a corresponding location and/or position of a reference (e.g., a reference genome). In some embodiments a local genome bias estimate comprises a quantitative measure of bias of a sequence (e.g., a sequence read, a sequence of a reference genome). A local genome bias estimation can be determined by a suitable method or mathematical process. In some embodiments a local genome bias estimate is determined by a suitable distribution and/or a suitable distribution function (e.g., a PDF). In some embodiments a local genome bias estimate comprises a quantitative representation of a PDF. In some embodiments a local genome bias estimate (e.g., a probability density estimation (PDE), a kernel density estimation) is determined by a probability density function (e.g., a PDF, e.g., a kernel density function) of a local bias content. In some embodiments a density estimation comprises a kernel density estimation. A local genome bias estimate is sometimes expressed as an average, mean, or median of a distribution. Sometimes a local genome bias estimate is expressed as a sum or an integral (e.g., an area under a curve (AUC) of a suitable distribution.

A PDF (e.g., a kernel density function, e.g., an Epanechnikov kernel density function) often comprises a bandwidth variable (e.g., a bandwidth). A bandwidth variable often defines the size and/or length of a window from which a probability density estimate (PDE) is derived when using a PDF. A window from which a PDE is derived often comprises a defined length of polynucleotides. In some embodiments a window from which a PDE is derived is a portion. A portion (e.g., a portion size, a portion length) is often determined according to a bandwidth variable. A bandwidth variable determines the length or size of the window used to determine a local genome bias estimate. a length of a polynucleotide segment (e.g., a contiguous segment of nucleotide bases) from which a local genome bias estimate is determined. A PDE (e.g., read density, local genome bias estimate (e.g., a GC density)) can be determined using any suitable bandwidth, non-limiting examples of which include a bandwidth of about 5 bases to about 100,000 bases, about 5 bases to about 50,000 bases, about 5 bases to about 25,000 bases, about 5 bases to about 10,000 bases, about 5 bases to about 5,000 bases, about 5 bases to about 2,500 bases, about 5 bases to about 1000 bases, about 5 bases to about 500 bases, about 5 bases to about 250 bases, about 20 bases to about 250 bases, or the like. In some embodiments a local genome bias estimate (e.g., a GC density) is determined using a bandwidth of about 400 bases or less, about 350 bases or less, about 300 bases or less, about 250 bases or less, about 225 bases or less, about 200 bases or less, about 175 bases or less, about 150 bases or less, about 125 bases or less, about 100 bases or less, about 75 bases or less, about 50 bases or less or about 25 bases or less. In certain embodiments a local genome bias estimate (e.g., a GC density) is determined using a bandwidth determined according to an average, mean, median, or maximum read length of sequence reads obtained for a given subject and/or sample. Sometimes a local genome bias estimate (e.g., a GC density) is determined using a bandwidth about equal to an average, mean, median, or maximum read length of sequence reads obtained for a given subject and/or sample. In some embodiments a local genome bias estimate (e.g., a GC density) is determined using a bandwidth of about 250, 240, 230, 220, 210, 200, 190, 180, 160, 150, 140, 130, 120, 110, 100, 90, 80, 70, 60, 50, 40, 30, 20 or about 10 bases.

A local genome bias estimate can be determined at a single base resolution, although local genome bias estimates (e.g., local GC content) can be determined at a lower resolution. In some embodiments a local genome bias estimate is determined for a local bias content. A local genome bias estimate (e.g., as determined using a PDF) often is determined using a window. In some embodiments, a local genome bias estimate comprises use of a window comprising a pre-selected number of bases. Sometimes a window comprises a segment of contiguous bases. Sometimes a window comprises one or more portions of non-contiguous bases. Sometimes a window comprises one or more portions (e.g., portions of a genome). A window size or length is often determined by a bandwidth and according to a PDF. In some embodiments a window is about 10 or more, 8 or more, 7 or more, 6 or more, 5 or more, 4 or more, 3 or more, or about 2 or more times the length of a bandwidth. A window is sometimes twice the length of a selected bandwidth when a PDF (e.g., a kernel density function) is used to determine a density estimate. A window may comprise any suitable number of bases. In some embodiments a window comprises about 5 bases to about 100,000 bases, about 5 bases to about 50,000 bases, about 5 bases to about 25,000 bases, about 5 bases to about 10,000 bases, about 5 bases to about 5,000 bases, about 5 bases to about 2,500 bases, about 5 bases to about 1000 bases, about 5 bases to about 500 bases, about 5 bases to about 250 bases, or about 20 bases to about 250 bases. In some embodiments a genome, or segments thereof, is partitioned into a plurality of windows. Windows encompassing regions of a genome may or may not overlap. In some embodiments windows are positioned at equal distances from each other. In some embodiments windows are positioned at different distances from each other. In certain embodiment a genome, or segment thereof, is partitioned into a plurality of sliding windows, where a window is slid incrementally across a genome, or segment thereof, where each window at each increment comprises a local genome bias estimate (e.g., a local GC density). A window can be slid across a genome at any suitable increment, according to any numerical pattern or according to any athematic defined sequence. In some embodiments, for a local genome bias estimate determination, a window is slid across a genome, or a segment thereof, at an increment of about 10,000 bp or more about 5,000 bp or more, about 2,500 bp or more, about 1,000 bp or more, about 750 bp or more, about 500 bp or more, about 400 bases or more, about 250 bp or more, about 100 bp or more, about 50 bp or more, or about 25 bp or more. In some embodiments, for a local genome bias estimate determination, a window is slid across a genome, or a segment thereof, at an increment of about 25, 24, 23, 22, 21, 20, 19, 18, 17, 16, 15, 14, 13, 12, 11, 10, 9, 8, 7, 6, 5, 4, 3, 2, or about 1 bp. For example, for a local genome bias estimate determination, a window may comprise about 400 bp (e.g., a bandwidth of 200 bp) and may be slid across a genome in increments of 1 bp. In some embodiments, a local genome bias estimate is determined for each base in a genome, or segment thereof, using a kernel density function and a bandwidth of about 200 bp.

In some embodiments a local genome bias estimate is a local GC content and/or a representation of local GC content. The term "local" as used herein (e.g., as used to describe a local bias, local bias estimate, local bias content, local genome bias, local GC content, and the like) refers to a polynucleotide segment of 10,000 bp or less. In some embodiments the term "local" refers to a polynucleotide segment of 5000 bp or less, 4000 bp or less, 3000 bp or less, 2000 bp or less, 1000 bp or less, 500 bp or less, 250 bp or less, 200 bp or less, 175 bp or less, 150 bp or less, 100 bp or less, 75 bp or less, or 50 bp or less. A local GC content is often a representation (e.g., a mathematical, a quantitative representation) of GC content for a local segment of a genome, sequence read, sequence read assembly (e.g., a contig, a profile, and the like). For example, a local GC content can be a local GC bias estimate or a GC density.

One or more GC densities are often determined for polynucleotides of a reference or sample (e.g., a test sample). In some embodiments a GC density is a representation (e.g., a mathematical, a quantitative representation) of local GC content (e.g., for a polynucleotide segment of 5000 bp or less). In some embodiments a GC density is a local genome bias estimate. A GC density can be determined using a suitable process described herein and/or known in the art. A GC density can be determined using a suitable PDF (e.g., a kernel density function (e.g., an Epanechnikov kernel density function). In some embodiments a GC density is a PDE (e.g., a kernel density estimation). In certain embodiments, a GC density is defined by the presence or absence of one or more guanine (G) and/or cytosine (C) nucleotides. Inversely, in some embodiments, a GC density can be defined by the presence or absence of one or more a adenine (A) and/or thymidine (T) nucleotides. GC densities for local GC content, in some embodiments, are normalized according to GC densities determined for an entire genome, or segment thereof (e.g., autosomes, set of chromosomes, single chromosome, a gene). One or more GC densities can be determined for polynucleotides of a sample (e.g., a test sample) or a reference sample. A GC density often is determined for a reference genome. In some embodiments a GC density is determined for a sequence read according to a reference genome. A GC density of a read is often determined according to a GC density determined for a corresponding location and/or position of a reference genome to which a read is mapped. In some embodiments a GC density determined for a location on a reference genome is assigned and/or provided for a read, where the read, or a segment thereof, maps to the same location on the reference genome. Any suitable method can be used to determine a location of a mapped read on a reference genome for the purpose of generating a GC density for a read. In some embodiments a median position of a mapped read determines a location on a reference genome from which a GC density for the read is determined. For example, where the median position of a read maps to Chromosome 12 at base number x of a reference genome, the GC density of the read is often provided as the GC density determined by a kernel density estimation for a position located on Chromosome 12 at or near base number x of the reference genome. In some embodiments a GC density is determined for some or all base positions of a read according to a reference genome. Sometimes a GC density of a read comprises an average, sum, median or integral of two or more GC densities determined for a plurality of base positions on a reference genome.

In some embodiments a local genome bias estimation (e.g., a GC density) is quantitated and/or is provided a value. A local genome bias estimation (e.g., a GC density) is sometimes expressed as an average, mean, and/or median. A local genome bias estimation (e.g., a GC density) is sometimes expressed as a maximum peak height of a PDE. Sometimes a local genome bias estimation (e.g., a GC density) is expressed as a sum or an integral (e.g., an area under a curve (AUC)) of a suitable PDE. In some embodiments a GC density comprises a kernel weight. In certain embodiments a GC density of a read comprises a value about equal to an average, mean, sum, median, maximum peak height or integral of a kernel weight.

Bias Frequencies

Bias frequencies are sometimes determined according to one or more local genome bias estimates (e.g., GC densities). A bias frequency is sometimes a count or sum of the number of occurrences of a local genome bias estimate for a sample, reference (e.g., a reference genome, a reference sequence) or part thereof. A bias frequency is sometimes a count or sum of the number of occurrences of a local genome bias estimate (e.g., each local genome bias estimate) for a sample, reference, or part thereof. In some embodiments a bias frequency is a GC density frequency. A GC density frequency is often determined according to one or more GC densities. For example, a GC density frequency may represent the number of times a GC density of value x is represented over an entire genome, or a segment thereof. A bias frequency is often a distribution of local genome bias estimates, where the number of occurrences of each local genome bias estimate is represented as a bias frequency. Bias frequencies are sometimes mathematically manipulated and/or normalized. Bias frequencies can be mathematically manipulated and/or normalized by a suitable method. In some embodiments, bias frequencies are normalized according to a representation (e.g., a fraction, a percentage) of each local genome bias estimate for a sample, reference or part thereof (e.g., autosomes, a subset of chromosomes, a single chromosome, or reads thereof). Bias frequencies can be determined for some or all local genome bias estimates of a sample or reference. In some embodiments bias frequencies can be determined for local genome bias estimates for some or all sequence reads of a test sample.

In some embodiments a system comprises a bias density module 6. A bias density module can accept, retrieve and/or store mapped sequence reads 5 and reference sequences 2 in any suitable format and generate local genome bias estimates, local genome bias distributions, bias frequencies, GC densities, GC density distributions and/or GC density frequencies (collectively represented by box 7). In some embodiments a bias density module transfers data and/or information (e.g., 7) to another suitable module (e.g., a relationship module 8).

Relationships

In some embodiments one or more relationships are generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In some embodiments a suitable relationship is determined between local genome bias estimates and bias frequencies. In some embodiments generating a relationship between (i) local genome bias estimates and (ii) bias frequencies for a sample provides a sample bias relationship. In some embodiments generating a relationship between (i) local genome bias estimates and (ii) bias frequencies for a reference provides a reference bias relationship. In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content. In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution.

Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments a system comprises a relationship module 8. A relationship module can generate relationships as well as functions, coefficients, constants and variables that define a relationship. A relationship module can accept, store and/or retrieve data and/or information (e.g., 7) from a suitable module (e.g., a bias density module 6) and generate a relationship. A relationship module often generates and compares distributions of local genome bias estimates. A relationship module can compare data sets and sometimes generate regressions and/or fitted relationships. In some embodiments a relationship module compares one or more distributions (e.g., distributions of local genome bias estimates of samples and/or references) and provides weighting factors and/or weighting assignments 9 for counts of sequence reads to another suitable module (e.g., a bias correction module). Sometimes a relationship module provides normalized counts of sequence reads directly to a distribution module 21 where the counts are normalized according to a relationship and/or a comparison.

Generating a Comparison and Use Thereof

In some embodiments a process for reducing local bias in sequence reads comprises normalizing counts of sequence reads. Counts of sequence reads are often normalized according to a comparison of a test sample to a reference. For example, sometimes counts of sequence reads are normalized by comparing local genome bias estimates of sequence reads of a test sample to local genome bias estimates of a reference (e.g., a reference genome, or part thereof). In some embodiments counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads are often normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample.

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count sometimes are determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

Sometimes a system comprises a bias correction module 10. In some embodiments, functions of a bias correction module are performed by a relationship modeling module 8. A bias correction module can accept, retrieve, and/or store mapped sequence reads and weighting factors (e.g., 9) from a suitable module (e.g., a relationship module 8, a compression module 4). In some embodiments a bias correction module provides a count to mapped reads. In some embodiments a bias correction module applies weighting assignments and/or bias correction factors to counts of sequence reads thereby providing normalized and/or adjusted counts. A bias correction module often provides normalized counts to a another suitable module (e.g., a distribution module 21).

In certain embodiments normalizing counts comprises factoring one or more features in addition to GC density, and normalizing counts of the sequence reads. In certain embodiments normalizing counts comprises factoring one or more different local genome bias estimates, and normalizing counts of the sequence reads. In certain embodiments counts of sequence reads are weighted according to a weighting determined according to one or more features (e.g., one or more biases). In some embodiments counts are normalized according to one or more combined weights. Sometimes factoring one or more features and/or normalizing counts according to one or more combined weights are by a process comprising use of a multivariate model. Any suitable multivariate model can be used to normalize counts. Non-limiting examples of a multivariate model include a multivariate linear regression, multivariate quantile regression, a multivariate interpolation of empirical data, a non-linear multivariate model, the like, or a combination thereof.

In some embodiments a system comprises a multivariate correction module 13. A multivariate correction module can perform functions of a bias density module 6, relationship module 8 and/or a bias correction module 10 multiple times thereby adjusting counts for multiple biases. In some embodiments a multivariate correction module comprises one or more bias density modules 6, relationship modules 8 and/or bias correction modules 10. Sometimes a multivariate correction module provides normalized counts 11 to another suitable module (e.g., a distribution module 21).

Weighted Portions

In some embodiments portions are weighted. In some embodiments one or more portions are weighted thereby providing weighted portions. Weighting portions sometimes removes portion dependencies. Portions can be weighted by a suitable process. In some embodiments one or more portions are weighted by an eigen function (e.g., an eigen-function). In some embodiments an eigen function comprises replacing portions with orthogonal eigen-portions. In some embodiments a system comprises a portion weighting module 42. In some embodiments a weighting module accepts, retrieves and/or stores read densities, read density profiles, and/or adjusted read density profiles. In some embodiments weighted portions are provided by a portion weighting module. In some embodiments, a weighting module is required to weight portions. A weighting module can weight portions by one or more weighting methods known in the art or described herein. A weighting module often provides weighted portions to another suitable module (e.g., a scoring module 46, a PCA statistics module 33, a profile generation module 26 and the like).

Principal Component Analysis

In some embodiments a read density profile (e.g., a read density profile of a test sample is adjusted according to a principal component analysis (PCA). A read density profile of one or more reference samples and/or a read density profile of a test subject can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies one or more biases in a read density profile. A bias identified by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments one or more biases can be removed from a read density profile by subtracting one or more principal components from a read density profile. Although bias in a read density profile is often identified and/or quantitated by a PCA of a profile, principal components are often subtracted from a profile at the level of read densities. A PCA often identifies one or more principal components. In some embodiments a PCA identifies a $1^{st}$, $2^{nd}$, $3^{rd}$, $4^{th}$, $5^{th}$, $6^{th}$, $7^{th}$, $8^{th}$, $9^{th}$, and a $10^{th}$ or more principal components. In certain embodiments 1, 2, 3, 4, 5, 6, 7, 8, 9, 10 or more principal components are used to adjust a profile. Often, principal components are used to adjust a profile in the order of there appearance in a PCA. For example, where three principal components are subtracted from a read density profile, a $1^{st}$, $2^{nd}$ and $3^{rd}$ principal component are used. Sometimes a bias identified by a principal component comprises a feature of a profile that is not used to adjust a profile. For example, a PCA may identify a genetic variation (e.g., an aneuploidy, microduplication, microdeletion, deletion, translocation, insertion) and/or a gender difference as a principal component. Thus, in some embodiments, one or more principal components are not used to adjust a profile. For example, sometimes a $1^{st}$, $2^{nd}$ and $4^{th}$ principal component are used to adjust a profile where a $3^{rd}$ principal component is not used to adjust a profile. A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). In certain instances, a PCA is performed on a median read density profile obtained from a training set comprising multiple samples resulting in the identification of a $1^{st}$ principal component and a second principal component. In some embodiments principal components are obtained from a set of subjects known to be devoid of a genetic variation in question. In some embodiments principal components are obtained from a set of known euploids. Principal component are often identified according to a PCA performed using one or more read density profiles of a reference (e.g., a training set). One or more principal components obtained from a reference are often subtracted from a read density profile of a test subject thereby providing an adjusted profile.

In some embodiments a system comprises a PCA statistics module 33. A PCA statistics module can accepts and/or retrieve read density profiles from another suitable module (e.g., a profile generation module 26). A PCA is often performed by a PCA statistics module. A PCA statistics module often accepts, retrieves and/or stores read density profiles and processes read density profiles from a reference set 32, training set 30 and/or from one or more test subjects 28. A PCA statistics module can generate and/or provide principal components and/or adjust read density profiles according to one or more principal components. Adjusted read density profiles (e.g., 40, 38) are often provided by a PCA statistics module. A PCA statistics module can provide and/or transfer adjusted read density profiles (e.g., 38, 40) to another suitable module (e.g., a portion weighting module 42, a scoring module 46). In some embodiments a PCA statistics module can provide a gender call 36. A gender call is sometimes a determination of fetal gender determined according to a PCA and/or according to one or more principal components. In some embodiments a PCA statistics module comprises some, all or a modification of the R code shown below. An R code for computing principal components generally starts with cleaning the data (e.g., subtracting median, filtering portions, and trimming extreme values):

```
#Clean the data outliers for PCA
dclean <- (dat - m)[mask,]
for (j in 1:ncol(dclean))
{
q <- quantile(dclean[,j],c(.25,.75))
qmin <- q[1] - 4*(q[2]-q[1])
qmax <- q[2] + 4*(q[2]-q[1])
dclean[dclean[,j] < qmin,j] <- qmin
dclean[dclean[,j] > qmax,j] <- qmax
}
```

Then the principal components are computed:
Compute principal components
pc←prcomp(dclean)$x
Finally, each sample's PCA-adjusted profile can be computed with:

```
#Compute residuals
mm <- model.matrix(~pc[,1:numpc])
for (j in 1:ncol(dclean))
dclean[,j] <- dclean[,j] - predict(lm(dclean[,j]~mm))
```

Comparing Profiles

In some embodiments, determining an outcome comprises a comparison. In certain embodiments, a read density profile, or a portion thereof, is utilized to provide an outcome. In some embodiments determining an outcome (e.g., a determination of the presence or absence of a genetic variation) comprises a comparison of two or more read density profiles. Comparing read density profiles often comprises comparing read density profiles generated for a selected segment of a genome. For example, a test profile is often compared to a reference profile where the test and reference profiles were determined for a segment of a genome (e.g., a reference genome) that is substantially the same segment. Comparing read density profiles sometimes comprises comparing two or more subsets of portions of a read density profile. A subset of portions of a read density profile may represent a segment of a genome (e.g., a chromosome, or segment thereof). A read density profile can comprise any amount of subsets of portions. Sometimes a read density profile comprises two or more, three or more, four or more, or five or more subsets. In certain embodiments a read density profile comprises two subsets of portions where each portion represents segments of a reference genome that are adjacent. In some embodiments a test profile can be compared to a reference profile where the test profile and reference profile both comprise a first subset of portions and a second subset of portions where the first and second subsets represent different segments of a genome.

Some subsets of portions of a read density profile may comprise genetic variations and other subsets of portions are sometimes substantially free of genetic variations. Sometimes all subsets of portions of a profile (e.g., a test profile) are substantially free of a genetic variation. Sometimes all subsets of portions of a profile (e.g., a test profile) comprise a genetic variation. In some embodiments a test profile can comprise a first subset of portions that comprise a genetic variation and a second subset of portions that are substantially free of a genetic variation.

In some embodiments methods described herein comprise preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In certain embodiments comparing two or more read density profiles comprises determining and/or comparing a measure of uncertainty for two or more read density profiles. Read density profiles and/or associated measures of uncertainty are sometimes compared to facilitate interpretation of mathematical and/or statistical manipulations of a data set and/or to provide an outcome. A read density profile generated for a test subject sometimes is compared to a read density profile generated for one or more references (e.g., reference samples, reference subjects, and the like). In some embodiments an outcome is provided by comparing a read density profile from a test subject to a read density profile from a reference for a chromosome, portions or segments thereof, where a reference read density profile is obtained from a set of reference subjects known not to possess a genetic variation (e.g., a reference). In some embodiments an outcome is provided by comparing a read density profile from a test subject to a read density profile from a reference for a chromosome, portions or segments thereof, where a reference read density profile is obtained from a set of reference subjects known to possess a specific genetic variation (e.g., a chromosome aneuploidy, a trisomy, a microduplication, a microdeletion).

In certain embodiments, a read density profile of a test subject is compared to a predetermined value representative of the absence of a genetic variation, and sometimes deviates from a predetermined value at one or more genomic locations (e.g., portions) corresponding to a genomic location in which a genetic variation is located. For example, in test subjects (e.g., subjects at risk for, or suffering from a medical condition associated with a genetic variation), read density profiles are expected to differ significantly from read density profiles of a reference (e.g., a reference sequence, reference subject, reference set) for selected portions when a test subject comprises a genetic variation in question. Read density profiles of a test subject are often substantially the same as read density profiles of a reference (e.g., a reference sequence, reference subject, reference set) for selected portions when a test subject does not comprise a genetic variation in question. Read density profiles are often compared to a predetermined threshold and/or threshold range. The term "threshold" as used herein refers to any number that is calculated using a qualifying data set and serves as a limit of diagnosis of a genetic variation (e.g., a copy number variation, an aneuploidy, a chromosomal aberration, a microduplication, a microdeletion, and the like). In certain embodiments a threshold is exceeded by results obtained by methods described herein and a subject is diagnosed with a genetic variation (e.g., a trisomy). In some embodiments a threshold value or range of values often is calculated by mathematically and/or statistically manipulating sequence read data (e.g., from a reference and/or subject). A predetermined threshold or threshold range of values indicative of the presence or absence of a genetic variation can vary while still providing an outcome useful for determining the presence or absence of a genetic variation. In certain embodiments, a read density profile comprising normalized read densities and/or normalized counts is generated to facilitate classification and/or providing an outcome. An outcome can be provided based on a plot of a read density profile comprising normalized counts (e.g., using a plot of such a read density profile).

In some embodiments a system comprises a scoring module 46. A scoring module can accept, retrieve and/or store read density profiles (e.g., adjusted, normalized read density profiles) from another suitable module (e.g., a profile generation module 26, a PCA statistics module 33, a portion weighting module 42, and the like). A scoring module can accept, retrieve, store and/or compare two or more read density profiles (e.g., test profiles, reference profiles, training sets, test subjects). A scoring module can often provide a score (e.g., a plot, profile statistics, a comparison (e.g., a difference between two or more profiles), a Z-score, a measure of uncertainty, a call zone, a sample call 50 (e.g., a determination of the presence or absence of a genetic variation), and/or an outcome). A scoring module can provide a score to an end user and/or to another suitable module (e.g., a display, printer, the like). In some embodiments a scoring module comprises some, all or a modification of the R code shown below which comprises an R function for computing Chi-square statistics for a specific test (e.g., High-chr21 counts).

The three parameters are:

```
x = sample read data (portion x sample)
m = median values for portions
y = test vector (Ex. False for all portions except True for chr21)
getChisqP <- function(x,m,y)
{
ahigh <- apply(x[!y,],2,function(x) sum((x>m[!y])))
alow <- sum((!y))-ahigh
bhigh <- apply(x[y,],2,function(x) sum((x>m[y])))
blow <- sum(y)-bhigh
p <- sapply(1:length(ahigh), function(i) {
p <- chisq.test(matrix(c(ahigh[i],alow[i],bhigh[i],blow[i]),2))$p.value/2
if (ahigh[i]/alow[i] > bhigh[i]/blow[i]) p <- max(p, 1-p)
else p <- min(p, 1-p); p})
return(p)
```

Hybrid Regression Normalization

In some embodiments a hybrid normalization method is used. In some embodiments a hybrid normalization method reduces bias (e.g., GC bias). A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method. For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, genomic section levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by ChAI or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome. A suitable measure of GC content can be used, non-limiting examples of which include a measure of guanine, cytosine, adenine, thymine, purine (GC), or pyrimidine (AT or ATU) content, melting temperature ($T_m$) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample (e.g., a sample obtained from a pregnant female). In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis. An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is predetermined. In some embodiments a correlation coefficient cut-off is about 0.5 or greater, about 0.55 or greater, about 0.6 or greater, about 0.65 or greater, about 0.7 or greater, about 0.75 or greater, about 0.8 or greater or about 0.85 or greater.

For example, in certain embodiments, a normalization method comprising a linear regression is used when a correlation coefficient is equal to or greater than about 0.6. In certain embodiments, counts of a sample (e.g., counts per portion of a reference genome, counts per portion) are normalized according to a linear regression when a correlation coefficient is equal to or greater than a correlation coefficient cut-off of 0.6, otherwise the counts are normalized according to a non-linear regression (e.g., when the coefficient is less than a correlation coefficient cut-off of 0.6). In some embodiments a normalization process comprises generating a linear regression or non-linear regression for the (i) the counts and (ii) the GC content, for each portion of multiple portions of a reference genome. In certain embodiments, a normalization method comprising a non-linear regression (e.g., a LOWESS, a LOESS) is used when a correlation coefficient is less than a correlation coefficient cut-off of 0.6. In some embodiments a normalization method comprising a non-linear regression (e.g., a LOWESS) is used when a correlation coefficient (e.g., a correlation coefficient) is less than a correlation coefficient cut-off of about 0.7, less than about 0.65, less than about 0.6, less than about 0.55 or less than about 0.5. For example, in some embodiments a normalization method comprising a non-linear regression (e.g., a LOWESS, a LOESS) is used when a correlation coefficient is less than a correlation coefficient cut-off of about 0.6.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts. Any suitable method can be used to subtract a regression line from the counts. For example, if counts x are derived from portion i (e.g., a portion i) comprising a GC content of 0.5 and a regression line determines counts y at a GC content of 0.5, then x−y=normalized counts for portion i. In some embodiments counts are normalized prior to and/or after subtracting a regression. In some embodiments, counts normalized by a hybrid normalization approach are used to generate genomic section levels, Z-cores, levels and/or profiles of a genome or a segment thereof. In certain embodiments, counts normalized by a hybrid normalization approach are analyzed by methods described herein to determine the presence or absence of a genetic variation (e.g., in a fetus).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

For example, in some embodiments multiple samples from multiple pregnant female subjects are analyzed and a subset of portions (e.g., portions of a reference genome) are selected according to count variability. In certain embodiments a linear regression is used to determine a correlation coefficient for (i) counts and (ii) GC content, for each of the selected portions for a sample obtained from a pregnant female subject. In some embodiments a correlation coefficient is determined that is greater than a pre-determined correlation cutoff value (e.g., of about 0.6), an assessment of the goodness of fit is indicative of a linear regression and the counts are normalized by subtracting the linear regression from the counts. In certain embodiments a correlation coefficient is determined that is less than a pre-determined correlation cutoff value (e.g., of about 0.6), an assessment of the goodness of fit is indicative of a non-linear regression, an LOESS regression is generated and the counts are normalized by subtracting the LOESS regression from the counts.

Profiles

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a segment of a chromosome) often is a collection of normalized or non-normalized counts for two or more portions. A profile often includes at least one level (e.g., a genomic section level), and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to maternal microdeletions or maternal duplications (e.g., copy number variations). In some embodiments levels are padded that are due to fetal microduplications or fetal microdeletions. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments levels in a profile that are due to microduplications and/or deletions are identified and adjusted (e.g., padded and/or removed) by a process sometimes referred to as padding or hole padding. In certain embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured fetal fraction, principle components). The terms "raw count profile plot" or "raw profile plot" as used herein refer to a plot of counts in each portion in a region normalized to total counts in a region (e.g., genome, portion, chromosome, chromosome portions of a reference genome or a segment of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected portion is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or threshold range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, portions or segments thereof from a set of references known not to carry a genetic variation, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

A data set profile can be generated by one or more manipulations of counted mapped sequence read data. Some embodiments include the following. Sequence reads are mapped and the number of sequence tags mapping to each genomic portion are determined (e.g., counted). A raw count profile is generated from the mapped sequence reads that are counted. An outcome is provided by comparing a raw count profile from a test subject to a reference median count profile for chromosomes, portions or segments thereof from a set of reference subjects known not to possess a genetic variation, in certain embodiments.

In some embodiments, sequence read data is optionally filtered to remove noisy data or uninformative portions. After filtering, the remaining counts typically are summed to generate a filtered data set. A filtered count profile is generated from a filtered data set, in certain embodiments.

After sequence read data have been counted and optionally filtered, data sets can be normalized to generate levels or profiles. A data set can be normalized by normalizing one or more selected portions to a suitable normalizing reference value. In some embodiments, a normalizing reference value is representative of the total counts for the chromosome or chromosomes from which portions are selected. In certain embodiments, a normalizing reference value is representative of one or more corresponding portions, portions of chromosomes or chromosomes from a reference data set prepared from a set of reference subjects known not to possess a genetic variation. In some embodiments, a normalizing reference value is representative of one or more corresponding portions, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a profile comprising normalized counts is generated to facilitate classification and/or providing an outcome. An outcome can be provided based on a plot of a profile comprising normalized counts (e.g., using a plot of such a profile).

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which include portion-wise normalization, normalization by GC content, median count normalization, linear and nonlinear least squares regression, LOESS (e.g., GC LOESS), LOWESS, ChAI, principal component normalization, RM, GCRM, cQn, the like and/or combinations thereof. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value. A level for one or more portions is synonymous with a "genomic section level" herein.

A level for one or more portions is synonymous with a "genomic section level" herein. The term "level" as used herein is sometimes synonymous with the term "elevation". A determination of the meaning of the term "level" can be determined from the context in which it is used. For example, the term "level", when used in the context of genomic sections, profiles, reads and/or counts often means an elevation. The term "level", when used in the context of a substance or composition (e.g., level of RNA, plexing level) often refers to an amount. The term "level", when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or segment thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a segment of a chromosome).

In some embodiments, a level is determined for normalized or non-normalized counts of portions that are contiguous. In some embodiments portions (e.g., a set of portions) that are contiguous represent neighboring segments of a genome or neighboring segments of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or segment thereof. In some embodiments a level is determined from a collection (e.g., a set) of contiguous portions and/or non-contiguous portions.

Outcome

Methods described herein can provide a determination of the presence or absence of a genetic variation (e.g., fetal aneuploidy) for a sample, thereby providing an outcome (e.g., thereby providing an outcome determinative of the presence or absence of a genetic variation (e.g., fetal aneuploidy)). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to portions (e.g., counts, counts of genomic portions of a reference genome). Determining an outcome, in some embodiments, comprises analyzing nucleic acid from a pregnant female. In certain embodiments, an outcome is determined according to counts (e.g., normalized counts) obtained from a pregnant female where the counts are from nucleic acid obtained from the pregnant female.

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. In certain embodiments methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to portions of a reference genome. Counts of sequence reads utilized to determine presence or absence of a genetic variation sometimes are raw counts and/or filtered counts, and often are normalized counts. A suitable normalization process or processes can be used to generate normalized counts, non-limiting examples of which include portion-wise normalization, normalization by GC content, linear and nonlinear least squares regression, LOESS, GC LOESS, LOWESS, ChAI, RM, GCRM and combinations thereof. Normalized counts sometimes are expressed as one or more levels or levels in a profile for a particular set or sets of portions. Normalized counts sometimes are adjusted or padded prior to determining presence or absence of a genetic variation.

In some embodiments an outcome is determined according to one or more levels. In some embodiments, a determination of the presence or absence of a genetic variation (e.g., a chromosome aneuploidy) is determined according to one or more adjusted levels. In some embodiments a determination of the presence or absence of a genetic variation (e.g., a chromosome aneuploidy) is determined according to a profile comprising 1 to about 10,000 adjusted levels. Often a determination of the presence or absence of a genetic variation (e.g., a chromosome aneuploidy) is determined according to a profile comprising about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 adjustments. In some embodiments a determination of the presence or absence of a genetic variation (e.g., a chromosome aneuploidy) is determined according to a profile comprising about 1 adjustment (e.g., one adjusted level). In some embodiments an outcome is determined according to one or more profiles (e.g., a profile of a chromosome or segment thereof) comprising one or more, 2 or more, 3 or more, 5 or more, 6 or more, 7 or more, 8 or more, 9 or more or sometimes 10 or more adjustments. In some embodiments, a determination of the presence or absence of a genetic variation (e.g., a chromosome aneuploidy) is determined according to a profile where some levels in a profile are not adjusted. In some embodiments, a determination of the presence or absence of a genetic variation (e.g., a chromosome aneuploidy) is determined according to a profile where adjustments are not made.

In some embodiments, an adjustment of a level (e.g., a first level) in a profile reduces a false determination or false outcome. In some embodiments, an adjustment of a level (e.g., a first level) in a profile reduces the frequency and/or probability (e.g., statistical probability, likelihood) of a false determination or false outcome. A false determination or outcome can be a determination or outcome that is not accurate. A false determination or outcome can be a determination or outcome that is not reflective of the actual or true genetic make-up or the actual or true genetic disposition (e.g., the presence or absence of a genetic variation) of a subject (e.g., a pregnant female, a fetus and/or a combination thereof). In some embodiments a false determination or outcome is a false negative determination. In some embodiments a negative determination or negative outcome is the absence of a genetic variation (e.g., aneuploidy, copy number variation). In some embodiments a false determination or false outcome is a false positive determination or false positive outcome. In some embodiments a positive determination or positive outcome is the presence of a genetic variation (e.g., aneuploidy, copy number variation). In some embodiments, a determination or outcome is utilized in a diagnosis. In some embodiments, a determination or outcome is for a fetus.

Presence or absence of a genetic variation (e.g., fetal aneuploidy) sometimes is determined without comparing counts for a set of portions to a reference. Counts measured for a test sample and are in a test region (e.g., a set of portions of interest) are referred to as "test counts" herein. Test counts sometimes are processed counts, averaged or summed counts, a representation, normalized counts, or one or more levels or levels as described herein. In certain embodiments test counts are averaged or summed (e.g., an average, mean, median, mode or sum is calculated) for a set of portions, and the averaged or summed counts are compared to a threshold or range. Test counts sometimes are expressed as a representation, which can be expressed as a ratio or percentage of counts for a first set of portions to counts for a second set of portions. In certain embodiments the first set of portions is for one or more test chromosomes (e.g., chromosome 13, chromosome 18, chromosome 21, or combination thereof) and sometimes the second set of portions is for the genome or a part of the genome (e.g., autosomes or autosomes and sex chromosomes). In certain embodiments a representation is compared to a threshold or range. In certain embodiments test counts are expressed as one or more levels or levels for normalized counts over a set of portions, and the one or more levels or levels are compared to a threshold or range. Test counts (e.g., averaged or summed counts, representation, normalized counts, one or more levels or levels) above or below a particular threshold, in a particular range or outside a particular range sometimes are determinative of the presence of a genetic variation or lack of euploidy (e.g., not euploidy). Test counts (e.g., averaged or summed counts, representation, normalized counts, one or more levels or levels) below or above a particular threshold, in a particular range or outside a particular range sometimes are determinative of the absence of a genetic variation or euploidy.

Presence or absence of a genetic variation (e.g., fetal aneuploidy) sometimes is determined by comparing counts, non-limiting examples of which include test counts, reference counts, raw counts, filtered counts, averaged or summed counts, representations (e.g., chromosome representations), normalized counts, one or more levels or levels (e.g., for a set of portions, e.g., genomic section levels, profiles), Z-scores, the like or combinations thereof. In some embodiments test counts are compared to a reference (e.g., reference counts). A reference (e.g., a reference count) can be a suitable determination of counts, non-limiting examples of which include raw counts, filtered counts, averaged or summed counts, representations (e.g., chromosome representations), normalized counts, one or more levels or levels (e.g., for a set of portions, e.g., genomic section levels, profiles), Z-scores, the like or combinations thereof. Reference counts often are counts for a euploid test region or from a segment of a genome or chromosome that is euploid. In some embodiments reference counts and test counts are obtained from the same sample and/or the same subject. In some embodiments reference counts are from different samples and/or from different subjects. In some embodiments reference counts are determined from and/or compared to a corresponding segment of the genome from which the test counts are derived and/or determined. A corresponding segment refers to a segment, portion or set of portions that map to the same location of a reference genome. In some embodiments reference counts are determined from and/or compared to a different segment of the genome from which the test counts are derived and/or determined.

In certain embodiments, test counts sometimes are for a first set of portions and a reference includes counts for a second set of portions different than the first set of portions. Reference counts sometimes are for a nucleic acid sample from the same pregnant female from which the test sample is obtained. In certain embodiments reference counts are for a nucleic acid sample from one or more pregnant females different than the female from which the test sample was obtained. In some embodiments, a first set of portions is in chromosome 13, chromosome 18, chromosome 21, a segment thereof or combination of the foregoing, and the second set of portions is in another chromosome or chromosomes or segment thereof. In a non-limiting example, where a first set of portions is in chromosome 21 or segment thereof, a second set of portions often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of deviation between the test counts and the reference counts can be generated.

In certain embodiments a reference comprises counts for the same set of portions as for the test counts, where the counts for the reference are from one or more reference samples (e.g., often multiple reference samples from multiple reference subjects). A reference sample often is from one or more pregnant females different than a female from which a test sample is obtained. A measure of deviation (e.g., a measure of uncertainty, an uncertainty value) between the test counts and the reference counts can be generated. In some embodiments a measure of deviation is determined from the test counts. In some embodiments a measure of deviation is determined from the reference counts. In some embodiments a measure of deviation is determined from an entire profile or a subset of portions within a profile.

A suitable measure of deviation can be selected, non-limiting examples of which include standard deviation, average absolute deviation, median absolute deviation, maximum absolute deviation, standard score (e.g., z-value, z-score, normal score, standardized variable) and the like. In some embodiments, reference samples are euploid for a test region and deviation between the test counts and the reference counts is assessed. In some embodiments a determination of the presence or absence of a genetic variation is according to the number of deviations (e.g., measures of deviations, MAD) between test counts and reference counts for a segment or portion of a genome or chromosome. In some embodiments the presence of a genetic variation is determined when the number of deviations between test counts and reference counts is greater than about 1, greater than about 1.5, greater than about 2, greater than about 2.5, greater than about 2.6, greater than about 2.7, greater than about 2.8, greater than about 2.9, greater than about 3, greater than about 3.1, greater than about 3.2, greater than about 3.3, greater than about 3.4, greater than about 3.5, greater than about 4, greater than about 5, or greater than about 6. For example, sometimes a test count differs from a reference count by more than 3 measures of deviation (e.g., 3 sigma, 3 MAD) and the presence of a genetic variation is determined. In some embodiments a test count obtained from a pregnant female is larger than a reference count by more than 3 measures of deviation (e.g., 3 sigma, 3 MAD) and the presence of a fetal chromosome aneuploidy (e.g., a fetal trisomy) is determined. A deviation of greater than three between test counts and reference counts often is indicative of a non-euploid test region (e.g., presence of a genetic variation). Test counts significantly above reference counts, which reference counts are indicative of euploidy, sometimes are determinative of a trisomy. In some embodiments a test count obtained from a pregnant female is less than a reference count by more than 3 measures of deviation (e.g., 3 sigma, 3 MAD) and the presence of a fetal chromosome aneuploidy (e.g., a fetal monosomy) is determined.

Test counts significantly below reference counts, which reference counts are indicative of euploidy, sometimes are determinative of a monosomy.

In some embodiments the absence of a genetic variation is determined when the number of deviations between test counts and reference counts is less than about 3.5, less than about 3.4, less than about 3.3, less than about 3.2, less than about 3.1, less than about 3.0, less than about 2.9, less than about 2.8, less than about 2.7, less than about 2.6, less than about 2.5, less than about 2.0, less than about 1.5, or less than about 1.0. For example, sometimes a test count differs from a reference count by less than 3 measures of deviation (e.g., 3 sigma, 3 MAD) and the absence of a genetic variation is determined. In some embodiments a test count obtained from a pregnant female differs from a reference count by less than 3 measures of deviation (e.g., 3 sigma, 3 MAD) and the absence of a fetal chromosome aneuploidy (e.g., a fetal euploid) is determined. In some embodiments (e.g., deviation of less than three between test counts and reference counts (e.g., 3-sigma for standard deviation) often is indicative of a euploid test region (e.g., absence of a genetic variation). A measure of deviation between test counts for a test sample and reference counts for one or more reference subjects can be plotted and visualized (e.g., z-score plot).

Any other suitable reference can be factored with test counts for determining presence or absence of a genetic variation (or determination of euploid or non-euploid) for a test region of a test sample. For example, a fetal fraction determination can be factored with test counts to determine the presence or absence of a genetic variation. A suitable process for quantifying fetal fraction can be utilized, non-limiting examples of which include a mass spectrometric process, sequencing process or combination thereof.

In some embodiments the presence or absence of a fetal chromosomal aneuploidy (e.g., a trisomy) is determined, in part, from a fetal ploidy determination. In some embodiments a fetal ploidy is determined by a suitable method described herein. In some certain embodiments a fetal ploidy determination of about 1.20 or greater, 1.25 or greater, 1.30 or greater, about 1.35 or greater, about 1.4 or greater, or about 1.45 or greater indicates the presence of a fetal chromosome aneuploidy (e.g., the presence of a fetal trisomy). In some embodiments a fetal ploidy determination of about 1.20 to about 2.0, about 1.20 to about 1.9, about 1.20 to about 1.85, about 1.20 to about 1.8, about 1.25 to about 2.0, about 1.25 to about 1.9, about 1.25 to about 1.85, about 1.25 to about 1.8, about 1.3 to about 2.0, about 1.3 to about 1.9, about 1.3 to about 1.85, about 1.3 to about 1.8, about 1.35 to about 2.0, about 1.35 to about 1.9, about 1.35 to about 1.8, about 1.4 to about 2.0, about 1.4 to about 1.85 or about 1.4 to about 1.8 indicates the presence of a fetal chromosome aneuploidy (e.g., the presence of a fetal trisomy). In some embodiments the fetal aneuploidy is a trisomy. In some embodiments the fetal aneuploidy is a trisomy of chromosome 13, 18 and/or 21.

In some embodiments a fetal ploidy of less than about 1.35, less than about 1.30, less than about 1.25, less than about 1.20 or less than about 1.15 indicates the absence of a fetal aneuploidy (e.g., the absence of a fetal trisomy, e.g., euploid). In some embodiments a fetal ploidy determination of about 0.7 to about 1.35, about 0.7 to about 1.30, about 0.7 to about 1.25, about 0.7 to about 1.20, about 0.7 to about 1.15, about 0.75 to about 1.35, about 0.75 to about 1.30, about 0.75 to about 1.25, about 0.75 to about 1.20, about 0.75 to about 1.15, about 0.8 to about 1.35, about 0.8 to about 1.30, about 0.8 to about 1.25, about 0.8 to about 1.20, or about 0.8 to about 1.15 indicates the absence of a fetal chromosome aneuploidy (e.g., the absence of a fetal trisomy, e.g., euploid).

In some embodiments a fetal ploidy of less than about 0.8, less than about 0.75, less than about 0.70 or less than about 0.6 indicates the presence of a fetal aneuploidy (e.g., the presence of a chromosome deletion). In some embodiments a fetal ploidy determination of about 0 to about 0.8, about 0 to about 0.75, about 0 to about 0.70, about 0 to about 0.65, about 0 to about 0.60, about 0.1 to about 0.8, about 0.1 to about 0.75, about 0.1 to about 0.70, about 0.1 to about 0.65, about 0.1 to about 0.60, about 0.2 to about 0.8, about 0.2 to about 0.75, about 0.2 to about 0.70, about 0.2 to about 0.65, about 0.2 to about 0.60, about 0.25 to about 0.8, about 0.25 to about 0.75, about 0.25 to about 0.70, about 0.25 to about 0.65, about 0.25 to about 0.60, about 0.3 to about 0.8, about 0.3 to about 0.75, about 0.3 to about 0.70, about 0.3 to about 0.65, about 0.3 to about 0.60 indicates the presence of a fetal chromosome aneuploidy (e.g., the presence of a chromosome deletion). In some embodiments the fetal aneuploidy determined is a whole chromosome deletion.

In some embodiments a determination of the presence or absence of a fetal aneuploidy (e.g., according to one or more of the ranges of a ploidy determination above) is determined according to a call zone. In certain embodiments a call is made (e.g., a call determining the presence or absence of a genetic variation, e.g., an outcome) when a value (e.g. a ploidy value, a fetal fraction value, a level of uncertainty) or collection of values falls within a pre-defined range (e.g., a zone, a call zone). In some embodiments a call zone is defined according to a collection of values that are obtained from the same patient sample. In certain embodiments a call zone is defined according to a collection of values that are derived from the same chromosome or segment thereof. In some embodiments a call zone based on a ploidy determination is defined according a level of confidence (e.g., high level of confidence, e.g., low level of uncertainty) and/or a fetal fraction. In some embodiments a call zone is defined according to a ploidy determination and a fetal fraction of about 2.0% or greater, about 2.5% or greater, about 3% or greater, about 3.25% or greater, about 3.5% or greater, about 3.75% or greater, or about 4.0% or greater. For example, in some embodiments a call is made that a fetus comprises a trisomy 21 based on a ploidy determination of greater than 1.25 with a fetal fraction determination of 2% or greater or 4% or greater for a sample obtained from a pregnant female bearing a fetus. In certain embodiments, for example, a call is made that a fetus is euploid based on a ploidy determination of less than 1.25 with a fetal fraction determination of 2% or greater or 4% or greater for a sample obtained from a pregnant female bearing a fetus. In some embodiments a call zone is defined by a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments a call is made without using a call zone. In some embodiments a call is made using a call zone and additional data or information. In some embodiments a call is made based on a ploidy value without the use of a call zone. In some embodiments a call is made without calculating a ploidy value. In some embodiments a call is made based on visual inspection of a profile (e.g., visual inspection of genomic section levels). A call can be made by any suitable method based in full, or in part, upon determinations, values and/or data obtained by methods described herein, non-limiting examples of which include a fetal ploidy determination, a fetal fraction determination, maternal ploidy, uncertainty and/or confidence determinations, portion levels, levels, profiles, z-scores, expected chromosome representations, measured chromosome representations, counts (e.g., normalized counts, raw counts), fetal or maternal copy number variations (e.g., categorized copy number variations), significantly different levels, adjusted levels (e.g., padding), the like or combinations thereof.

In some embodiments a no-call zone is where a call is not made. In some embodiments a no-call zone is defined by a value or collection of values that indicate low accuracy, high risk, high error, low level of confidence, high level of uncertainty, the like or a combination thereof. In some embodiments a no-call zone is defined, in part, by a fetal fraction of about 5% or less, about 4% or less, about 3% or less, about 2.5% or less, about 2.0% or less, about 1.5% or less or about 1.0% or less.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Table 1). In certain embodiments a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis). Analysis and processing of data can provide one or more outcomes. The term "outcome" as used herein can refer to a result of data processing that facilitates determining the presence or absence of a genetic variation (e.g., an aneuploidy, a copy number variation). In certain embodiments the term "outcome" as used herein refers to a conclusion that predicts and/or determines the presence or absence of a genetic variation (e.g., an aneuploidy, a copy number variation). In certain embodiments the term "outcome" as used herein refers to a conclusion that predicts and/or determines a risk or probability of the presence or absence of a genetic variation (e.g., an aneuploidy, a copy number variation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Table 1) comprises use of an outcome determinative of the presence or absence of a genetic variation. In some embodiments, an outcome based on counted mapped sequence reads or transformations thereof is determinative of the presence or absence of a genetic variation. In certain embodiments, an outcome generated utilizing one or more methods (e.g., data processing methods) described herein is determinative of the presence or absence of one or more conditions, syndromes or abnormalities listed in Table 1. In certain embodiments a diagnosis comprises a determination of a presence or absence of a condition, syndrome or abnormality. Often a diagnosis comprises a determination of a genetic variation as the nature and/or cause of a condition, syndrome or abnormality. In certain embodiments an outcome is not a diagnosis. An outcome often comprises one or more numerical values generated using a processing method described herein in the context of one or more considerations of probability. A consideration of risk or probability can include, but is not limited to: an uncertainty value, a measure of variability, confidence level, sensitivity, specificity, standard deviation, coefficient of variation (CV) and/or confidence level, Z-scores, Chi values, Phi values, ploidy values, fitted fetal fraction, area ratios, median level, the like or combinations thereof. A consideration of probability can facilitate determining whether a subject is at risk of having, or has, a genetic variation, and an outcome determinative of a presence or absence of a genetic disorder often includes such a consideration.

An outcome sometimes is a phenotype. An outcome sometimes is a phenotype with an associated level of confidence (e.g., an uncertainty value, e.g., a fetus is positive for trisomy 21 with a confidence level of 99%, a test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or portion from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a level, a profile and/or a plot (e.g., a profile plot). In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. In certain embodiments a predetermined threshold or cutoff value is an expected level or an expected level range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein.

The term "sensitivity" as used herein refers to the number of true positives divided by the number of true positives plus the number of false negatives, where sensitivity (sens) may be within the range of $0 \leq sens \leq 1$. The term "specificity" as used herein refers to the number of true negatives divided by the number of true negatives plus the number of false positives, where sensitivity (spec) may be within the range of $0 \leq spec \leq 1$. In some embodiments a method that has sensitivity and specificity equal to one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

In some embodiments, presence or absence of a genetic variation (e.g., chromosome aneuploidy) is determined for a fetus. In such embodiments, presence or absence of a fetal genetic variation (e.g., fetal chromosome aneuploidy) is determined.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

After one or more outcomes have been generated, an outcome often is used to provide a determination of the presence or absence of a genetic variation and/or associated medical condition. An outcome typically is provided to a health care professional (e.g., laboratory technician or manager; physician or assistant). Often an outcome is provided by an outcome module. In certain embodiments an outcome is provided by a plotting module. In certain embodiments an outcome is provided on a peripheral or component of an apparatus. For example, sometimes an outcome is provided by a printer or display. In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence read data, or the like, into a representation of a subject's cellular nucleic acid, in certain embodiments. For example, analyzing sequence reads of nucleic acid from a subject and generating a chromosome profile and/or outcome can be viewed as a transformation of relatively small sequence read fragments to a representation of relatively large chromosome structure. In some embodiments, an outcome results from a transformation of sequence reads from a subject (e.g., a pregnant female), into a representation of an existing structure (e.g., a genome, a chromosome or segment thereof) present in the subject (e.g., a maternal and/or fetal nucleic acid). In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus).

In certain embodiments an outcome can be generated according to analyzing one or more candidate segments. In some embodiments the presence of absence of a genetic variation is determined according to a discrete segment, candidate segment or composite candidate segment (e.g., the presence or absence of a discrete segment, candidate segment or composite candidate segment). In some embodiments two candidate segments derived from two decomposition renderings of the same profile are substantially the same (e.g., according to a comparison) and the presence of a chromosome aneuploidy, microduplication or microdeletion is determined. In some embodiments the presence of a composite candidate segment indicates the presence of a chromosome aneuploidy, microduplication or microdeletion. In some embodiments the presence of a whole chromosome aneuploidy is determined according to the presence of a discrete segment, candidate segment or composite candidate segment in a profile and the profile is a segment of a genome (e.g., a segment larger than a chromosome, e.g., a segment representing two or more chromosomes, a segment representing an entire genome). In some embodiments the presence of a whole chromosome aneuploidy is determined according to the presence of a discrete segment, candidate segment or composite candidate segment in a profile and the discrete segment edges are substantially the same as the edges of a chromosome. In certain embodiments the presence of a microduplication or microdeletion is determined when at least one edge of a discrete segment, candidate segment or composite candidate segment in a profile is different than an edge of a chromosome and/or the discrete segment is within a chromosome. In some embodiments the presence of a microduplication is determined and a level or AUC for a discrete segment, candidate segment or composite candidate segment is substantially larger than a reference level (e.g., a euploid region). In some embodiments the presence of a microdeletion is determined and a level or AUC for a discrete segment, candidate segment or composite candidate segment is substantially less than a reference level (e.g., a euploid region). In some embodiments candidate segments identified in two or more different decomposition renderings are not substantially the same (e.g., are different) and the absence of a chromosome aneuploidy, microduplication and/or microdeletion is determined. In some embodiments the absence of a discrete segment, candidate segment or composite candidate segment in a profile or decomposition rendering of a profile indicates the absence of a chromosome aneuploidy, microduplication or microdeletion.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Laboratory personnel (e.g., a laboratory manager) can analyze values (e.g., test counts, reference counts, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

Genetic Variations and Medical Conditions

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In certain embodiments a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In certain embodiments a duplication is a mutation (e.g., a genetic aberration) in which a part of a chromosome or a sequence of DNA is copied and inserted back into the genome. In certain embodiments a genetic duplication (i.e. duplication) is any duplication of a region of DNA. In some embodiments a duplication is a nucleic acid sequence that is repeated, often in tandem, within a genome or chromosome.

In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In certain embodiments an insertion comprises the addition of a segment of a chromosome into a genome, chromosome, or segment thereof. In certain embodiments an insertion comprises the addition of an allele, a gene, an intron, an exon, any non-coding region, any coding region, segment thereof or combination thereof into a genome or segment thereof. In certain embodiments an insertion comprises the addition (i.e., insertion) of nucleic acid of unknown origin into a genome, chromosome, or segment thereof. In certain embodiments an insertion comprises the addition (i.e. insertion) of a single base.

As used herein a "copy number variation" generally is a class or type of genetic variation or chromosomal aberration. A copy number variation can be a deletion (e.g. microdeletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In certain embodiments a duplication comprises an insertion. In certain embodiments an insertion is a duplication. In certain embodiments an insertion is not a duplication. For example, often a duplication of a sequence in a portion increases the counts for a portion in which the duplication is found. Often a duplication of a sequence in a portion increases the level. In certain embodiments, a duplication present in portions making up a first level increases the level relative to a second level where a duplication is absent. In certain embodiments an insertion increases the counts of a portion and a sequence representing the insertion is present (i.e., duplicated) at another location within the same portion. In certain embodiments an insertion does not significantly increase the counts of a portion or level and the sequence that is inserted is not a duplication of a sequence within the same portion. In certain embodiments an insertion is not detected or represented as a duplication and a duplicate sequence representing the insertion is not present in the same portion.

In some embodiments a copy number variation is a fetal copy number variation. Often, a fetal copy number variation is a copy number variation in the genome of a fetus. In some embodiments a copy number variation is a maternal and/or fetal copy number variation. In certain embodiments a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" is a reference to the number of chromosomes present in a fetus or mother. In certain embodiments "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes is a reference to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of a level in a profile. Thus, a level representing an autosomal chromosome pair (e.g., a euploid) is often normalized to a ploidy of 1. Similarly, a level within a segment of a chromosome representing the absence of a duplication, deletion or insertion is often normalized to a microploidy of 1. Ploidy and microploidy are often portion-specific (e.g., portion specific) and sample-specific. Ploidy is often defined as integral multiples of ½, with the values of 1, ½, 0, 3/2, and 2 representing euploid (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploid (e.g., no copy number variation), a heterozygous deletion, homozygous deletion, heterozygous duplication and homozygous duplication, respectively. Some examples of ploidy values for a fetus are provided in Table 2.

In certain embodiments the microploidy of a fetus matches the microploidy of the mother of the fetus (i.e., the pregnant female subject). In certain embodiments the microploidy of a fetus matches the microploidy of the mother of the fetus and both the mother and fetus carry the same heterozygous copy number variation, homozygous copy number variation or both are euploid. In certain embodiments the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected level. For example, sometimes a level (e.g., a level in a profile, sometimes a level that includes substantially no copy number variation) is normalized to a value of 1 (e.g., a ploidy of 1, a microploidy of 1) and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method or apparatus described herein. Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In certain embodiments, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In certain embodiments, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjærg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinitis pigmentosa, and azoospermia.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome. The term "euploid", in some embodiments, refers a normal complement of chromosomes.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome). In some embodiments, a trisomy is a duplication of most or all of an autosome. In certain embodiments a trisomy is a whole chromosome aneuploidy resulting in three instances (e.g., three copies) of a particular type of chromosome (e.g., instead of two instances (i.e., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including) (XXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods and apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphoproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p, 5p minus | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobsen Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy; 15q deletion | Prader-Willi, Angelman's syndrome |
| 15 | trisomy (somatic) | myeloid and lymphoid lineages affected, e.g., MDS, ANLL, ALL, CLL) |
| 16 | trisomy | Full Trisomy 16 Mosaic Trisomy 16 |
| 16 | 16q13.3 deletion | Rubenstein-Taybi |
| 3 | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |

TABLE 1A-continued

| Chromosome | Abnormality | Disease Association |
|---|---|---|
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |

TABLE 1B-continued

| Syndrome | Chromosome | Start | End | Interval (Mb) | Grade |
|---|---|---|---|---|---|
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |

TABLE 1B-continued

| Syndrome | Chromosome | Start | End | Interval (Mb) | Grade |
|---|---|---|---|---|---|
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, Genereviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In certain embodiments, preeclampsia also is associated with elevated levels of extracellular nucleic acid and/or alterations in methylation patterns. For example, a positive correlation between extracellular fetal-derived hypermethylated RASSF1A levels and the severity of pre-eclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

Software can be used to perform one or more steps in the processes described herein, including but not limited to; counting, data processing, generating an outcome, and/or providing one or more recommendations based on generated outcomes, as described in greater detail hereafter.

Machines, Software and Interfaces

Certain processes and methods described herein (e.g., quantifying, partitioning, mapping, normalizing, range setting, adjusting, categorizing, counting and/or determining sequence reads, counts, levels (e.g., levels) and/or profiles) often cannot be performed without a computer, processor, software, module or other apparatus. Methods described herein typically are computer-implemented methods, and one or more portions of a method sometimes are performed by one or more processors (e.g., microprocessors), computers, or microprocessor controlled apparatuses. Embodiments pertaining to methods described in this document generally are applicable to the same or related processes implemented by instructions in systems, apparatus and computer program products described herein. In some embodiments, processes and methods described herein (e.g., quantifying, partitioning, counting and/or determining sequence reads, counts, levels and/or profiles) are performed by automated methods. In some embodiments one or more steps and a method described herein is carried out by a processor and/or computer, and/or carried out in conjunction with memory. In some embodiments, an automated method is embodied in software, modules, processors, peripherals and/or an apparatus comprising the like, that determine sequence reads, partitioning, counts, mapping, mapped sequence tags, levels, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, levels, and profiles derived from a test subject (e.g., a patient, a pregnant female) and/or from a reference subject can be further analyzed and processed to determine the presence or absence of a genetic variation. Sequence reads, counts, levels and/or profiles sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, portion or portion specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by maternal age, maternal ploidy, and fetal contribution. In certain embodiments, data sets characterized by one or more features or variables sometimes are processed after counting.

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more apparatus. Each apparatus comprises one or more of memory, one or more processors, and instructions. Where a system includes two or more apparatus, some or all of the apparatus may be located at the same location, some or all of the apparatus may be located at different locations, all of the apparatus may be located at one location and/or all of the apparatus may be located at different locations. Where a system includes two or more apparatus, some or all of the apparatus may be located at the same location as a user, some or all of the apparatus may be located at a location different than a user, all of the apparatus may be located at the same location as the user, and/or all of the apparatus may be located at one or more locations different than the user.

A system sometimes comprises a computing apparatus and a sequencing apparatus, where the sequencing apparatus is configured to receive physical nucleic acid and generate sequence reads, and the computing apparatus is configured to process the reads from the sequencing apparatus. The computing apparatus sometimes is configured to determine the presence or absence of a genetic variation (e.g., copy number variation; fetal chromosome aneuploidy) from the sequence reads.

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., sequencing module, logic processing module, data display organization module). The term "software" refers to computer readable program instructions that, when executed by a computer, perform computer operations. Instructions executable by the one or more processors sometimes are provided as executable code, that when executed, can cause one or more processors to implement a method described herein. A module described herein can exist as software, and instructions (e.g., processes, routines, subroutines) embodied in the software can be implemented or performed by a processor. For example, a module (e.g., a software module) can be a part of a program that performs a particular process or task. The term "module" refers to a self-contained functional unit that can be used in a larger apparatus or software system. A module can comprise a set of instructions for carrying out a function of the module. A module can transform data and/or information. Data and/or information can be in a suitable form. For example, data and/or information can be digital or analogue. In certain embodiments, data and/or information can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an apparatus, peripheral, component or another module. A module can perform one or more of the following non-limiting functions: partitioning a reference genome, or part thereof, mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a segment thereof, and/or padding), providing identification (e.g., identifying a copy number variation, genetic variation or aneuploidy), categorizing, plotting, and/or determining an outcome, for example. A processor can, in certain embodiments, carry out the instructions in a module. In some embodiments, one or more processors are required to carry out instructions in a module or group of modules. A module can provide data and/or information to another module, apparatus or source and can receive data and/or information from another module, apparatus or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and processor capable of implementing instructions from a module can be located in an apparatus or in different apparatus. A module and/or processor capable of implementing an instruction for a module can be located in the same location as a user (e.g., local network) or in a different location from a user (e.g., remote network, cloud system). In embodiments in which a method is carried out in conjunction with two or more modules, the modules can be located in the same apparatus, one or more modules can be located in different apparatus in the same physical location, and one or more modules may be located in different apparatus in different physical locations.

An apparatus, in some embodiments, comprises at least one processor for carrying out the instructions in a module. Counts of sequence reads mapped to portions of a reference genome sometimes are accessed by a processor that executes instructions configured to carry out a method described herein. Counts that are accessed by a processor can be within memory of a system, and the counts can be accessed and placed into the memory of the system after they are obtained. In some embodiments, an apparatus includes a processor (e.g., one or more processors) which processor can perform and/or implement one or more instructions (e.g., processes, routines and/or subroutines) from a module. In some embodiments, an apparatus includes multiple processors, such as processors coordinated and working in parallel. In some embodiments, an apparatus operates with one or more external processors (e.g., an internal or external network, server, storage device and/or storage network (e.g., a cloud)). In some embodiments, an apparatus comprises a module. In certain embodiments an apparatus comprises one or more modules. An apparatus comprising a module often can receive and transfer one or more of data and/or information to and from other modules. In certain embodiments, an apparatus comprises peripherals and/or components. In certain embodiments an apparatus can comprise one or more peripherals or components that can transfer data and/or information to and from other modules, peripherals and/or components. In certain embodiments an apparatus interacts with a peripheral and/or component that provides data and/or information. In certain embodiments peripherals and components assist an apparatus in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium having a computer readable program code embodied therein, the computer readable program code adapted to be executed to implement a method comprising: (a) obtaining sequence reads of sample nucleic acid from a test subject; (b) partitioning a reference genome, or part thereof; (c) mapping the sequence reads obtained in (a) to a reference genome, which reference genome has been divided into portions according to the partitioning in (b); (d) counting the mapped sequence reads within the portions; (e) generating a sample normalized count profile by normalizing the counts for the portions obtained in (d); and (f) determining the presence or absence of a genetic variation from the sample normalized count profile in (e).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed.

Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified result, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate counts of sequence reads, partition a reference genome, or part thereof, map the sequence reads to portions, count the mapped reads, and utilize the counted mapped reads in a method, system, apparatus or computer program product described herein, in some embodiments. Counts of sequence reads mapped to portions sometimes are transferred by one entity to a second entity for use by the second entity in a method, system, apparatus or computer program product described herein, in certain embodiments.

In some embodiments, one entity generates sequence reads and a second entity maps those sequence reads to portions in a reference genome in some embodiments. The second entity sometimes counts the mapped reads and utilizes the counted mapped reads in a method, system, apparatus or computer program product described herein. In certain embodiments the second entity transfers the mapped reads to a third entity, and the third entity counts the mapped reads and utilizes the mapped reads in a method, system, apparatus or computer program product described herein. In certain embodiments the second entity counts the mapped reads and transfers the counted mapped reads to a third entity, and the third entity utilizes the counted mapped reads in a method, system, apparatus or computer program product described herein. In embodiments involving a third entity, the third entity sometimes is the same as the first entity. That is, the first entity sometimes transfers sequence reads to a second entity, which second entity can map sequence reads to portions in a reference genome (e.g., a partitioned reference genome, or part thereof) and/or count the mapped reads, and the second entity can transfer the mapped and/or counted reads to a third entity. A third entity sometimes can utilize the mapped and/or counted reads in a method, system, apparatus or computer program product described herein, where the third entity sometimes is the same as the first entity, and sometimes the third entity is different from the first or second entity. In some embodiments a fourth entity generates the partitioned reference genome, or part thereof.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

Figure 12:
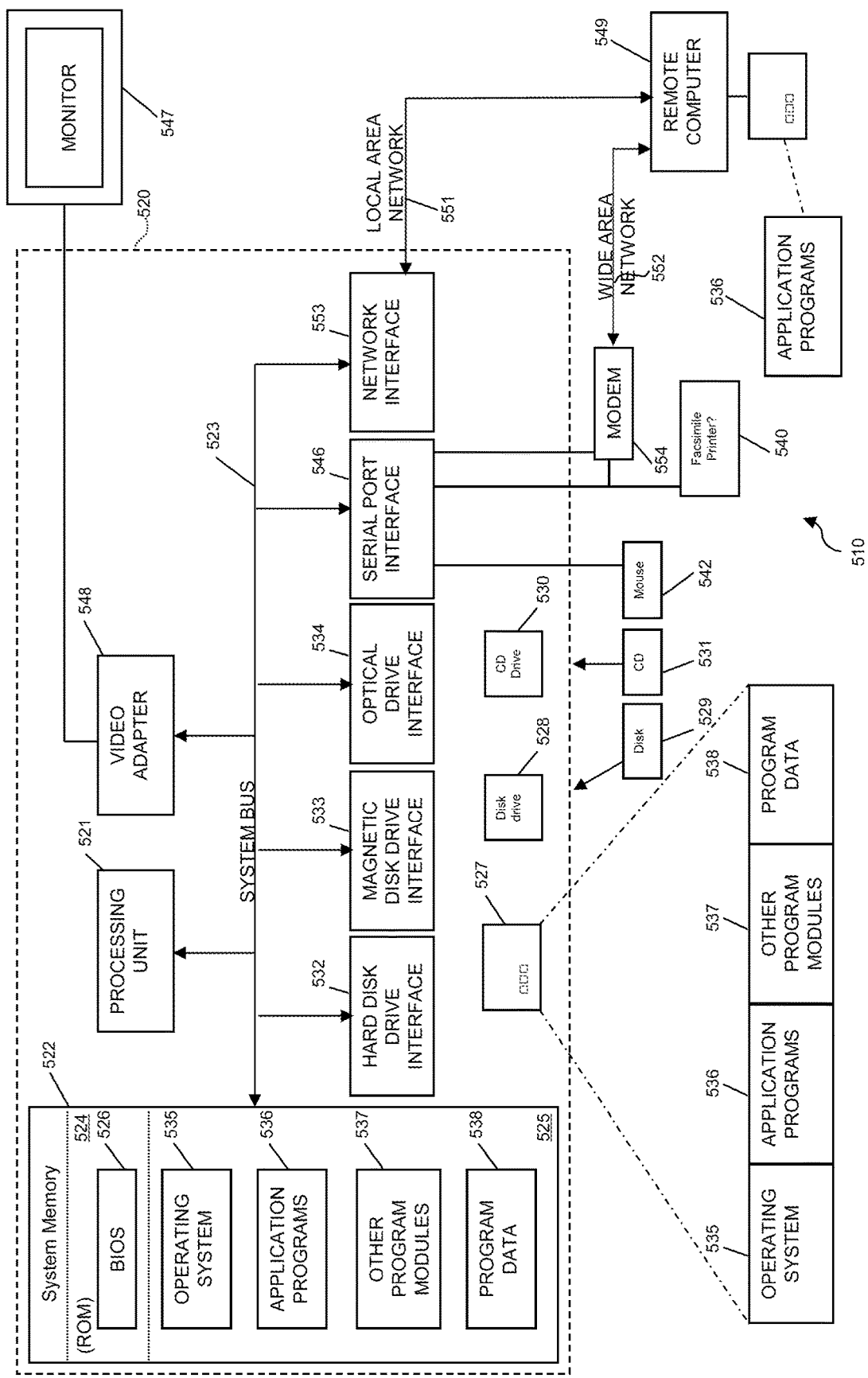
FIG. 12 shows an illustrative embodiment of a system in which certain embodiments of the technology may be implemented.

FIG. 12 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 12 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 12 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the processor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 12. The logical connections depicted in FIG. 12 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

Modules

One or more modules can be utilized in a method described herein, non-limiting examples of which include a logic processing module, sequencing module, partitioning module, mapping module, counting module, filtering module, weighting module, normalization module, GC bias module, level module, comparison module, range setting module, categorization module, plotting module, representation module, relationship module, outcome module and/or data display organization module, the like or combination thereof. Modules are sometimes controlled by a microprocessor. In certain embodiments a module or an apparatus comprising one or more modules, gather, assemble, receive, obtain, access, recover provide and/or transfer data and/or information to or from another module, apparatus, component, peripheral or operator of an apparatus. In some embodiments, data and/or information (e.g., sequencing reads) are provided to a module by an apparatus comprising one or more of the following: one or more flow cells, a camera, a detector (e.g., a photo detector, a photo cell, an electrical detector (e.g., an amplitude modulation detector, a frequency and phase modulation detector, a phase-locked loop detector), a counter, a sensor (e.g., a sensor of pressure, temperature, volume, flow, weight), a fluid handling device, a printer, a display (e.g., an LED, LCT or CRT), the like or combinations thereof. For example, sometimes an operator of an apparatus provides a constant, a threshold value, a formula or a predetermined value to a module. A module is often configured to transfer data and/or information to or from another module or apparatus. A module can receive data and/or information from another module, non-limiting examples of which include a logic processing module, sequencing module, partitioning module, mapping module, counting module, filtering module, weighting module, normalization module, GC bias module, level module, comparison module, range setting module, categorization module, plotting module, representation module, relationship module, outcome module and/or data display organization module, the like or combination thereof. A module can manipulate and/or transform data and/or information. Data and/or information derived from or transformed by a module can be transferred to another suitable apparatus and/or module, non-limiting examples of which include a logic processing module, sequencing module, partitioning module, mapping module, counting module, filtering module, weighting module, normalization module, GC bias module, level module, comparison module, range setting module, categorization module, plotting module, representation module, relationship module, outcome module and/or data display organization module, the like or combination thereof. An apparatus comprising a module can comprise at least one processor. In some embodiments, data and/or information are received by and/or provided by an apparatus comprising a module. An apparatus comprising a module can include a processor (e.g., one or more processors) which processor can perform and/or implement one or more instructions (e.g., processes, routines and/or subroutines) of a module. In some embodiments, a module operates with one or more external processors (e.g., an internal or external network, server, storage device and/or storage network (e.g., a cloud)).

Logic Processing Module

In certain embodiments a logic processing module orchestrates, controls, limits, organizes, orders, distributes, partitions, transforms and/or regulates data and/or information or the transfer of data and/or information to and from one or more other modules, peripherals or devices.

Data Display Organization Module

In certain embodiments a data display organization module processes and/or transforms data and/or information into a suitable visual medium non-limiting examples of which include images, video and/or text (e.g., numbers, letters and symbols). In some embodiments, a data display organization module processes, transforms and/or transfers data and/or information for presentation on a suitable display (e.g., a monitor, LED, LCD, CRT, the like or combinations thereof), a printer, a suitable peripheral or device. In some embodiments, a data display organization module processes, transforms data and/or information into a visual representation of a fetal or maternal genome, chromosome or part thereof.

Sequencing Module

In some embodiments, a sequence module obtains, generates, gathers, assembles, manipulates, transforms, processes, transforms and/or transfers sequence reads. A "sequence receiving module" as used herein is the same as a "sequencing module". An apparatus comprising a sequencing module can be any apparatus that determines the sequence of a nucleic acid utilizing a sequencing technology known in the art. In some embodiments a sequencing module can align, assemble, fragment, complement, reverse complement, error check, or error correct sequence reads.

Partitioning Module

A reference genome or part thereof (e.g., a chromosome, or part thereof, in a reference genome) can be partitioned by a partitioning module. A partitioning module can partition a reference genome, or part thereof, by a method described herein. In some embodiments, a partitioning module or an apparatus comprising a partitioning module is required to provide a partitioned reference genome, or part thereof.

Mapping Module

Sequence reads can be mapped by a mapping module or by an apparatus comprising a mapping module, which mapping module generally maps reads to a reference genome or segment thereof. A mapping module can map sequencing reads by a suitable method known in the art. In some embodiments, a mapping module or an apparatus comprising a mapping module is required to provide mapped sequence reads.

Counting Module

Counts can be provided by a counting module or by an apparatus comprising a counting module. In some embodiments a counting module counts sequence reads mapped to a reference genome. In some embodiments a counting module generates, assembles, and/or provides counts according to a counting method known in the art. In some embodiments, a counting module or an apparatus comprising a counting module is required to provide counts.

Filtering Module

Filtering portions (e.g., portions of a reference genome) can be provided by a filtering module (e.g., by an apparatus comprising a filtering module). In some embodiments, a filtering module is required to provide filtered portion data (e.g., filtered portions) and/or to remove portions from consideration. In certain embodiments a filtering module removes counts mapped to a portion from consideration. In certain embodiments a filtering module removes counts mapped to a portion from a determination of a level or a profile. A filtering module can filter data (e.g., counts, counts mapped to portions, portions, portion levels, normalized counts, raw counts, and the like) by one or more filtering methods known in the art or described herein.

Weighting Module

Weighting portions (e.g., portions of a reference genome) can be provided by a weighting module (e.g., by an apparatus comprising a weighting module). In some embodiments, a weighting module is required to weight genomics sections and/or provide weighted portion values. A weighting module can weight portions by one or more weighting methods known in the art or described herein.

Normalization Module

Normalized data (e.g., normalized counts) can be provided by a normalization module (e.g., by an apparatus comprising a normalization module). In some embodiments, a normalization module is required to provide normalized data (e.g., normalized counts) obtained from sequencing reads. A normalization module can normalize data (e.g., counts, filtered counts, raw counts) by one or more normalization methods described herein (e.g., ChAI, hybrid normalization, the like or combinations thereof) or known in the art.

GC Bias Module

Determining GC bias (e.g., determining GC bias for each of the portions of a reference genome (e.g., portions, portions of a reference genome)) can be provided by a GC bias module (e.g., by an apparatus comprising a GC bias module). In some embodiments, a GC bias module is required to provide a determination of GC bias. In some embodiments a GC bias module provides a determination of GC bias from a fitted relationship (e.g., a fitted linear relationship) between counts of sequence reads mapped to each of the portions of a reference genome and GC content of each portion. A GC bias module sometimes is part of a normalization module (e.g., ChAI normalization module).

Level Module

Determining levels (e.g., levels) and/or calculating genomic section levels for portions of a reference genome can be provided by a level module (e.g., by an apparatus comprising a level module). In some embodiments, a level module is required to provide a level or a calculated genomic section level (e.g., according to Equation I or II). In some embodiments a level module provides a level from a fitted relationship (e.g., a fitted linear relationship) between a GC bias and counts of sequence reads mapped to each of the portions of a reference genome. In some embodiments, a level module provides a genomic section level (i.e., $L_i$) according to equation $L_i = (m_i - G_i S) I^{-1}$ where $G_i$ is the GC bias, $m_i$ is measured counts mapped to each portion of a reference genome, i is a sample, and I is the intercept and S is the slope of the a fitted relationship (e.g., a fitted linear relationship) between a GC bias and counts of sequence reads mapped to each of the portions of a reference genome.

Comparison Module

A first level can be identified as significantly different from a second level by a comparison module or by an apparatus comprising a comparison module. In some embodiments, a comparison module or an apparatus comprising a comparison module is required to provide a comparison between two levels.

Range Setting Module

Expected ranges (e.g., expected level ranges) for various copy number variations (e.g., duplications, insertions and/or deletions) or ranges for the absence of a copy number variation can be provided by a range setting module or by an apparatus comprising a range setting module. In certain embodiments, expected levels are provided by a range setting module or by an apparatus comprising a range setting module. In some embodiments, a range setting module or an apparatus comprising a range setting module is required to provide expected levels and/or ranges.

Categorization Module

A copy number variation (e.g., a maternal and/or fetal copy number variation, a fetal copy number variation, a duplication, insertion, deletion) can be categorized by a categorization module or by an apparatus comprising a categorization module. In certain embodiments a copy number variation (e.g., a maternal and/or fetal copy number variation) is categorized by a categorization module. In certain embodiments a level (e.g., a first level) determined to be significantly different from another level (e.g., a second level) is identified as representative of a copy number variation by a categorization module. In certain embodiments the absence of a copy number variation is determined by a categorization module. In some embodiments, a determination of a copy number variation can be determined by an apparatus comprising a categorization module. A categorization module can be specialized for categorizing a maternal and/or fetal copy number variation, a fetal copy number variation, a duplication, deletion or insertion or lack thereof or combination of the foregoing. For example, a categorization module that identifies a maternal deletion can be different than and/or distinct from a categorization module that identifies a fetal duplication. In some embodiments, a categorization module or an apparatus comprising a categorization module is required to identify a copy number variation or an outcome determinative of a copy number variation.

Plotting Module

In some embodiments a plotting module processes and/or transforms data and/or information into a suitable visual medium, non-limiting examples of which include a chart, plot, graph, the like or combinations thereof. In some embodiments, a plotting module processes, transforms and/or transfers data and/or information for presentation on a suitable display (e.g., a monitor, LED, LCD, CRT, the like or combinations thereof), a printer, a suitable peripheral or device. In certain embodiments a plotting module provides a visual display of a count, a level, and/or a profile. In some embodiments, a data display organization module processes, transforms data and/or information into a visual representation of a fetal or maternal genome, chromosome or part thereof. In some embodiments, a plotting module or an apparatus comprising a plotting module is required to plot a count, a level or a profile.

Relationship Module

In certain embodiments, a relationship module processes and/or transforms data and/or information into a relationship. In certain embodiments, a relationship is generated by and/or transferred from a relationship module.

Outcome Module

The presence or absence of a genetic variation (an aneuploidy, a fetal aneuploidy, a copy number variation, a microdeletion, a microduplication) is, in some embodiments, identified by an outcome module or by an apparatus comprising an outcome module. In certain embodiments a genetic variation is identified by an outcome module. Often a determination of the presence or absence of an aneuploidy, a microdeletion, and/or a microduplication is identified by an outcome module. In some embodiments, an outcome determinative of a genetic variation (an aneuploidy, a copy number variation, a microdeletion, a microduplication) can be identified by an outcome module or by an apparatus comprising an outcome module. An outcome module can be specialized for determining a specific genetic variation (e.g., a trisomy, a trisomy 21, a trisomy 18, certain microdeletions or microduplications). For example, an outcome module that identifies a trisomy 21 can be different than and/or distinct from an outcome module that identifies a trisomy 18. In some embodiments, an outcome module or an apparatus comprising an outcome module is required to identify a genetic variation or an outcome determinative of a genetic variation (e.g., an aneuploidy, a copy number variation, a microdeletion, a microduplication). In some embodiments, an outcome module can identify whether a genetic variation (e.g., microduplication or microdeletion) is a maternal genetic variation or a fetal genetic variation. A genetic variation or an outcome determinative of a genetic variation identified by methods described herein can be independently verified by further testing (e.g., by targeted sequencing of maternal and/or fetal nucleic acid).

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Certain methods described herein may be performed in conjunction with methods described, for example in International Patent Application Publication No. WO2013/052907, International Patent Application Publication No. WO2013/055817, International Patent Application Publication No. WO2013/109981, International Patent Application Publication No. WO2013/177086, International Patent Application Publication No. WO2013/192562, International Patent Application Publication No. WO2014/116598, International Patent Application Publication No. WO2014/055774, International Patent Application Publication No. WO2014/190286, International Patent Application Publication No. WO2014/205401, and International Patent Application Publication No. WO2015/051163, each of which is incorporated by reference herein in its entirety.

EXAMPLES

The examples set forth below illustrate certain embodiments and do not limit the technology.

Example 1: Limit of Detection for Arbitrary Size Microdeletion/Microduplication

For extended content research (e.g., determining the presence or absence of a microdeletion or microduplication), one aspect is to understand the limit of detection (LoD) for an arbitrary size event. Four factors may affect the LoD of a given event: fetal fraction, event size, sequencing depth, and the genomic location of the event. Regarding the first three factors, an event generally can be more readily detected with higher fetal fraction, larger size and deeper sequencing. The fourth factor generally relates to the nature of sequencing: certain regions can be more unstable than others due to various reasons (e.g., guanine and cytosine (GC) bias, repetitive elements, mappability, and the like), and therefore events in certain regions can be more difficult to detect. In this example, a theoretical framework was developed to incorporate the aforementioned factors and derive an analytic formula to calculate the LoD.

Throughout the study, the event location and size were known (i.e., targeted detection). Also, samples were selected for which the event of interest was trisomic for the child and euploid for the mother, although the theory can be extended to other maternal-fetal ploidy combinations.

Independent Bin Count

Assume the genome has been portioned into $N_{total}$ equally spaced non-overlapping bins. For an unaffected euploid sample, let $x_i$ represent the bin count for bin $i \in (1, \ldots, N_{total})$. Due to the inherent randomness in sequencing, $x_i$ is a random variable with $x_i \sim f(\mu_{x_i}, \sigma_{x_i})$, where $\mu_{x_i}$ and $\sigma_{x_i}$ are the mean and standard deviation for bin i and $f(\bullet)$ is some distribution function. Similarly, for an affected trisomy sample, the bin count for the trisomy region is $y_i \sim f(\mu_{y_i}, \sigma_{y_i})$, where $\mu_{y_i} = \mu_{x_i}(1+f/2)$ and f is the fetal fraction. Note that the bin count variability is location specific, which accounts for the fourth factor described above.

For an event with size N spanning bin p to q, define the summed bin count $X \triangleq \sum_p^q x_i$ and $Y \triangleq \sum_p^q y_i$. Assuming bin counts are independent, $E[X] = \sum_p^q \mu_{x_i} \triangleq N\mu_x$, $sd[X] = \sqrt{\sum_p^q \sigma_{x_i}^2} \triangleq \sqrt{N}\sigma_x$, $E[Y] = \sum_p^q \mu_{y_i} \triangleq N\mu_y$ and $sd[Y] = \sqrt{\sum_p^q \sigma_{y_i}^2} \triangleq \sqrt{N}\sigma_y$, where $\mu_x$, $\sigma_x$, $\mu_y$, and $\sigma_y$ represent the average bin count mean and standard deviation for the event region.

The z-score of the event can be calculated as $$Z = \frac{Y - E[X]}{sd[X]} \tag{1}$$

It follows that $$E[Z] = \sqrt{N}\frac{\mu_x}{\sigma_x}\frac{f}{2}, \quad sd[Z] = \frac{\sigma_y}{\sigma_x} \approx 1.$$

Furthermore, by central limit theorem, Z can be approximated by a normal distribution if the number of bins N is reasonably large. In sum, we have derived the distribution of z-scores for an arbitrary size event $$Z \sim \text{Normal}\left(\sqrt{N}\frac{\mu_x}{\sigma_x}\frac{f}{2}, 1\right) \quad (2)$$

where N is the number bins for the event, $\mu_x$ and $\sigma_x$ are the average bin count mean and standard deviation for the event region in euploid samples, and f is the fetal fraction.

At a given false negative rate CZ, the minimum fetal fraction needed can be derived from Eq. (2)

$$f = \frac{2(Z_\alpha + c)\frac{\sigma_x}{\mu_x}}{\sqrt{N}} \quad (3)$$

Where c is the predefined z-score cutoff for euploids (e.g. c=3 for T21 detection), and $Z_\alpha$ is the critical value for standard normal distribution with a tail probability of α.

Dependent Bin Count

The method described above assumes that bins are independent; however, weak correlations sometimes are observed among the different bins for normalized data. In such case, $sd[X] \neq \sqrt{\sum_p {}^q\sigma_{x_i}^2}$. To calculate the LoD, redefine $E[X] \triangleq \mu_X$, $sd[X] \triangleq \sigma_X$, $E[Y] \triangleq \mu_Y = \mu_X(1+f/2)$ and $sd[Y] \triangleq \sigma_Y$. Assuming $\sigma_Y \approx \sigma_X$, the z-score distribution can be rewritten as:

$$Z \sim \text{Normal}\left(\frac{\mu_x}{\sigma_x}\frac{f}{2}, 1\right) \quad (4)$$

and at a given false negative rate α, the minimum fetal fraction is $$f = 2(Z_\alpha + c)\frac{\sigma_x}{\mu_x} \quad (5)$$

Note that $\mu_X$ and $\sigma_X$ can be empirically evaluated from a large pool of euploid samples.

Population Level Limit of Detection Calculation

Figure 6:
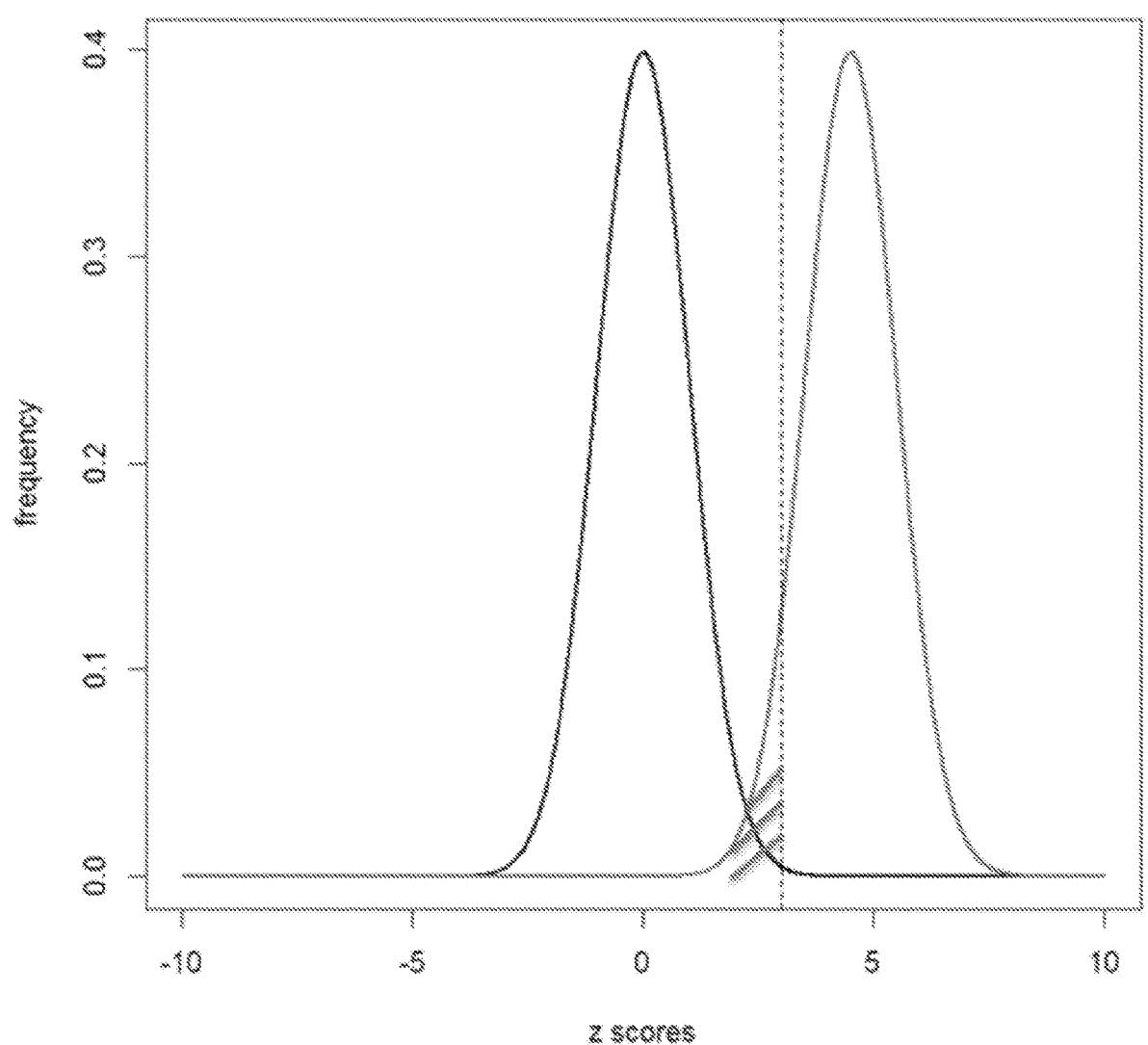
FIG. 6 shows z-score distributions for euploid events (left peak) and trisomic events (right peak). The shaded area represents false negative (FN) rate $\alpha$.

The population level false negative (FN) rate can be calculated by the following equation $$FN_{total} = \int_{f=0}^{1} FN(f)p(f)df \quad (6)$$

where FN(f) represent the FN rate at a given f (shaded area on FIG. 6), and p(f) represent the fetal fraction distribution. Therefore, to ensure a population level FN rate of α, one can solve $f_0$ for the following equation $$\alpha = \int_{f=f_0}^{1} FN(f)p(f)df \quad (7)$$

Results

Figure 7:
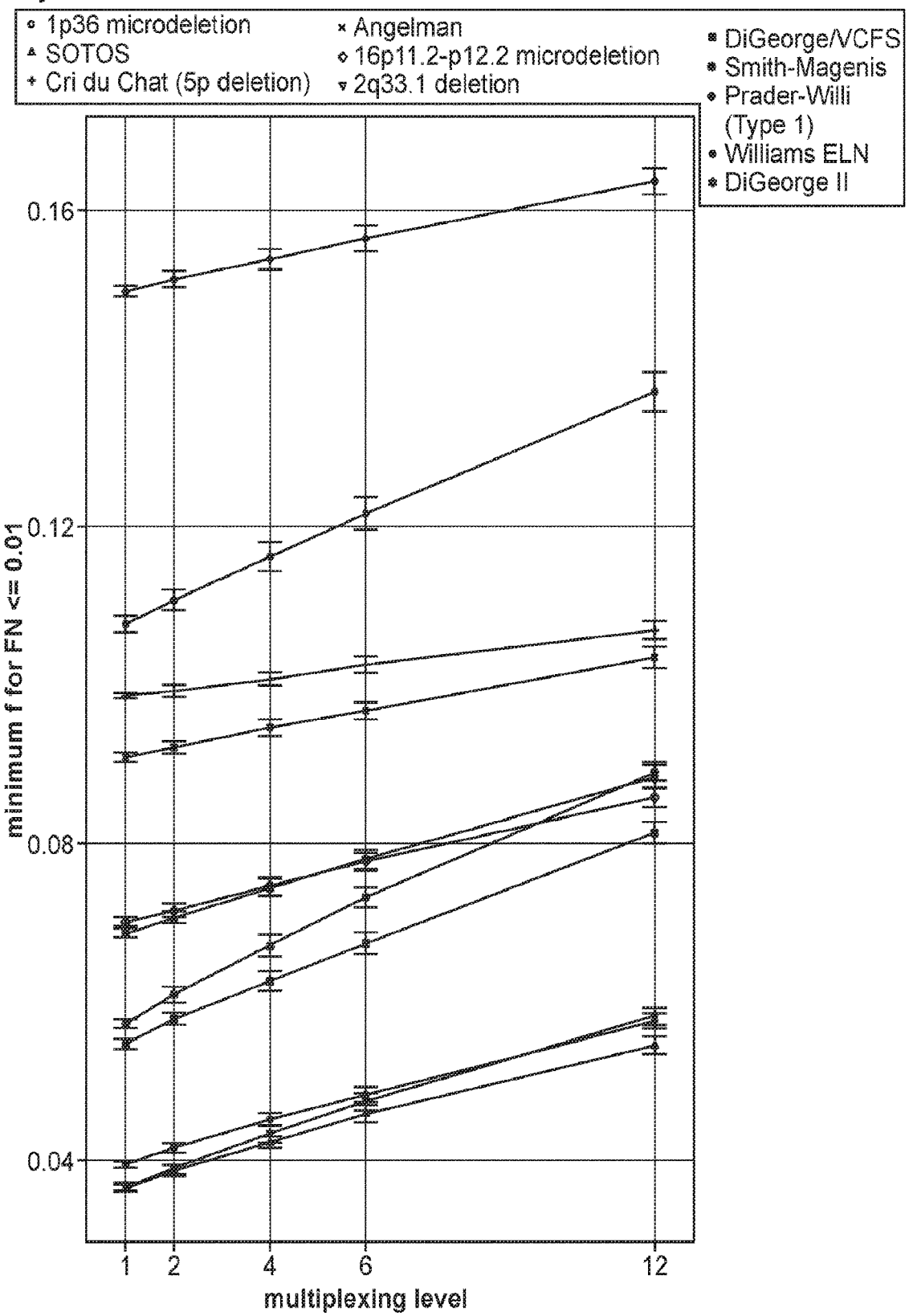
FIG. 7 shows minimum fetal fraction for microdeletion and/or microduplication detection to achieve a population level false negative (FN) rate of 1%.

The table in FIG. 8 shows a list of common microdeletion syndromes. Given this table, Equation (7) was applied to calculate the minimum fetal fractions to achieve a population level FN rate of 1% at different sequencing coverage (FIG. 7). In general, the minimum required fetal fraction is lower for larger syndromes and higher sequencing coverage.

Example 2: Optimal Discretization of Sequencing Data

This example provides methods for deriving optimal discretization of sequencing data for non-invasive prenatal testing (NIPT). For certain types of molecular diagnostics, copy number variations are detected for a subject. In certain instances, a nucleotide sequencing methodology (e.g., massively parallel sequencing) is applied to genomic material. One parameter of nucleotide sequencing is sequencing depth. Certain types of diagnostics and certain types of copy number variations may require different levels of sequencing depth. Generally, a lower sequencing depth can be used to detect larger copy number variations. In certain instances for which the analyte corresponds to a mixture of genomic material, such as for non-invasive prenatal testing (NIPT), the sequencing depth required to achieve a certain level of detection of copy number variations (CNVs) can related to the properties of the mixture.

Sequencing data can reflect properties of the original genomic material, and also can be influenced by various steps in the experimental process (e.g., preferential amplification of certain regions as a function of nucleotide composition). Features introduced by an experimental process sometimes are referred to as "bias". Quantifying these features can be an important step in an overall quantification scheme for the assessment of copy number variations (CNVs). Such features can be correlated with other properties of a reference data set, such as with the nucleotide composition of a reference genome. Depending on the sequencing depth (and, possibly, on the complexity of the analyte), sequencing data might be grouped or aggregated by specific regions from a reference dataset (such as regions from a reference genome). The discretization of genomic data (also referred to as "grouping", "aggregation", "segmenting", "partitioning" or "binning") typically uses regions of predetermined and equal length. In this example, methods are presented for performing more advanced groupings of sequencing data.

Discretization Using Wavelet GC Binning

As noted above, one factor which can influence the ability to determine copy number variations is variability in nucleotide composition as a function of a genomic region of interest. One method for optimal discretization of sequencing data is one which directly accounts for variability in nucleotide composition. Using a reference genome, an average nucleotide composition (such as, e.g., GC content) can be estimated at fixed resolution (e.g., 1 kb size) and then analyzed in the context of an extended genomic region, including an entire genome. In this example, GC content was estimated for a reference genome at a resolution of 1 kb. A transformation of these data can be applied, such a wavelet transformation with a Haar wavelet basis, using a pre-established level of decomposition. The proper choice of decomposition level can depend on the length of the chromosome $L_{chr}$ and the minimum desired bin size $L_{min}$. The wavelet decomposition level C can be computed by $C = \log_2 (L_{chr}/L_{min})$. In certain instances, decomposition level of C+1 or C−1 also can be used. $L_{min} = T_A * L_{Genome}/T_C$, where $T_A$ is the average count per bin (e.g. 250), $L_{genome}$ is the length of the genome, and $T_C$ is the total number of counts. The wavelet-transformed data, when using this basis, can determine the segmentation of the genomic region by which the sequencing data can be aggregated. In certain instances, a sliding window method, as described herein, can be applied.

After aggregating experimental data with respect to the segmentation described above, an optional step is to further filter regions for which the observed read density has an outlier behavior. The merits of such filtering can be judged based on the accuracy of CNV detection estimated from clinical studies.

Figure 2:
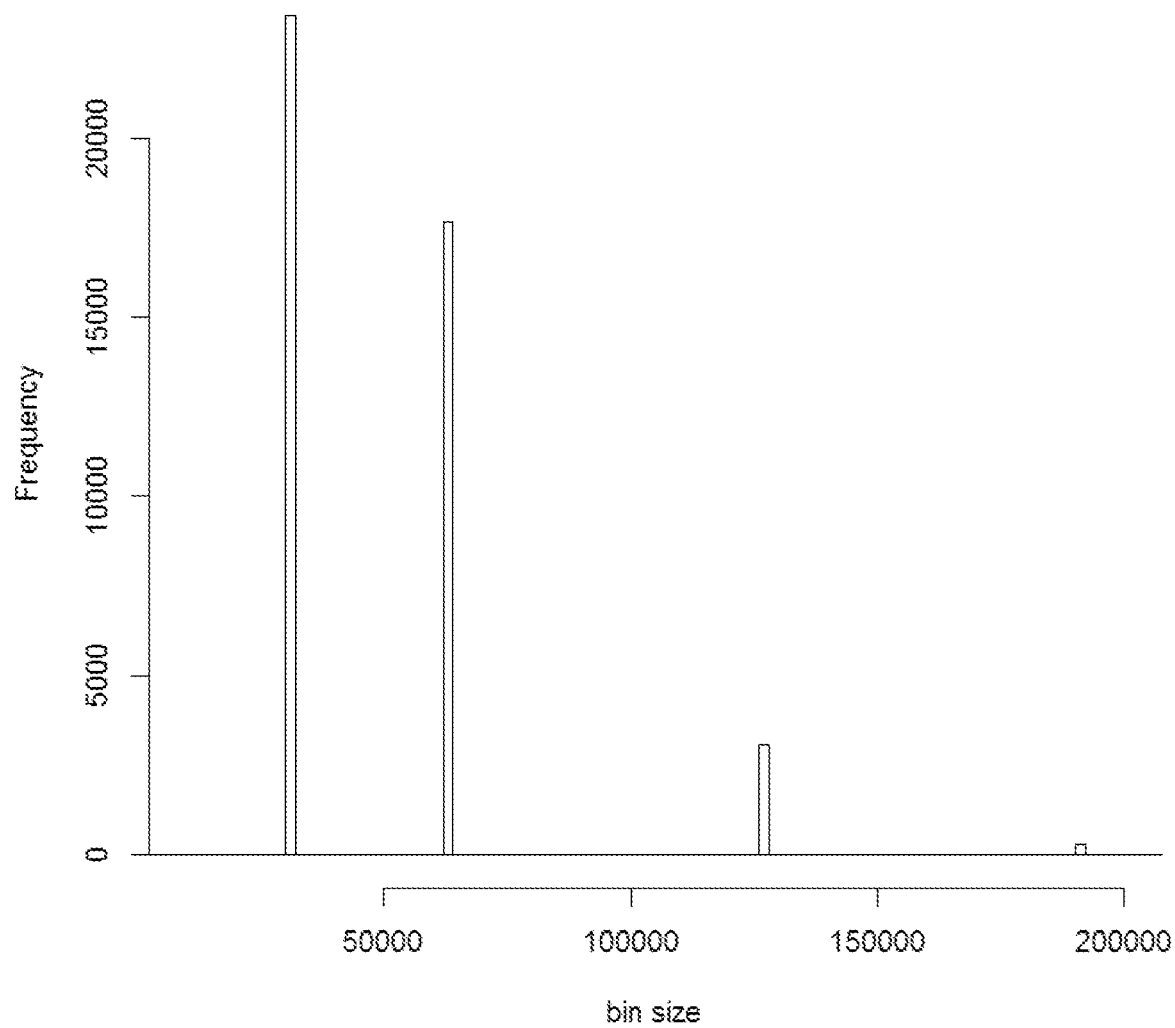
FIG. 2 shows an example of bin size distribution using a wavelet binning method.

FIG. 1 illustrates the wavelet GC binning method. The peaks/troughs represent GC content for 1 kb non-overlapping windows on chromosome 18 and the horizontal lines represent the GC content for the wavelet partitioned bins. As shown in FIG. 1, wavelet binning generally does not produce constant size bins (as opposed to 50 kb binning), but captures local GC effects by grouping bins with similar GC content together. FIG. 2 illustrates bin size distribution using the wavelet method, where the majority of bins are 32 kb or 64 kb long.

Figure 3:
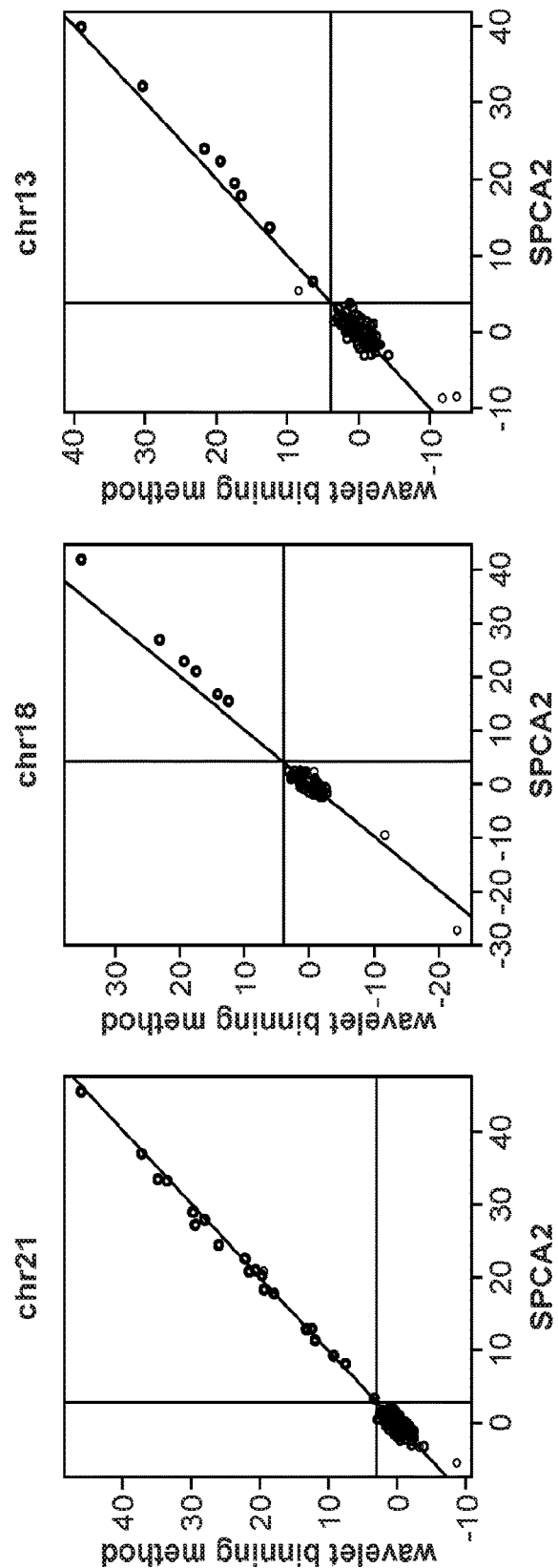
FIG. 3 shows classification results for chromosomes 21, 18 and 13 using a wavelet binning method and a 50 kb binning method on the LDTv4CE2 study. The accuracy is identical for the two methods.
Figure 5:
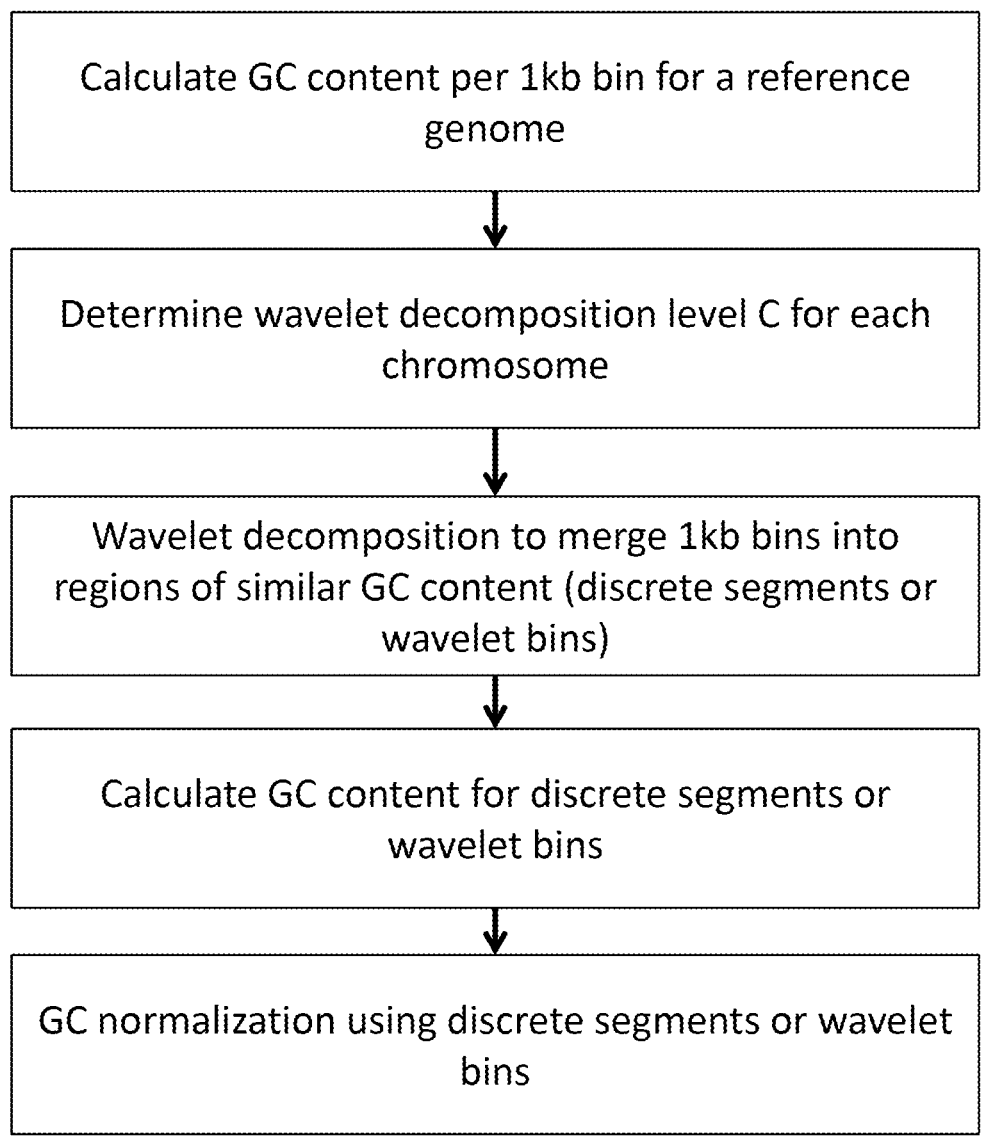
FIG. 5 shows an example workflow using a wavelet binning method.

After wavelet binning, samples can be normalized (e.g., LOESS, bin median, and/or PCA) with one additional step to compensate for the size of the bins. FIG. 3 shows classification results for the wavelet binning method and the 50 kb binning method on LDTv4CE2 data. The classification results were identical. FIG. 4 shows truth tables for chromosomes 21, 18 and 13 for the LDTv4CE2 study.

Discretization Based on Coverage Variability

Another method for optimal discretization of sequencing data can be derived using previously collected sequencing data. Variations in sequencing coverage as a function of genomic location were observed for sequencing results from mixtures of maternal and fetal ccfDNA. This variability may be present even when accounting for alignment artifacts or experimental factors (sometimes referred to as experimental bias).

Copy number variations can be determined by analyzing the density of sequencing data from various genomic regions of interest. According to a general statistical theory of density estimation, one method is to derive a histogram. The number of windows (also known as "breaks" or "bins" or "portions") in a histogram can vary but there are several theoretical methods which can be used to determine an optimal number of windows. Examples of these methods include Scott's rule or the Freedman-Diaconis rule. Given two genomic regions of interest which expand approximately equal sizes (as determined using a reference genome) and covered, either for a particular sample or on average, by N and, correspondingly, M reads, the ratio of optimal number of windows covering the first region and the one covering the second region can be estimated to be equal to $(M/N)^{1/3}$. This ratio also can be expressed as $(var_1/var_2)^{1/3}$, where $var_1$ is coverage variability for region 1 and $var_2$ is coverage variability for region 2. This ratio can be referred to as a proportionality factor. Using a predetermined value for average sequencing depth and a predetermined value for the complexity of the analyte (such a value of fetal fraction of interest), a limit of detection (LoD) calculation can be carried out to estimate an average size of CNV which can be detected with a predetermined accuracy. This value can be used to establish a general scale or resolution level for detecting CNVs in samples which have comparable complexity with the value used in the above calculation. Using this value and knowing the extent of a genomic region of interest over which CNVs can be investigated (which can also include an entire genome), an overall total number of bins can be calculated. Under the constraint of keeping this total number of bins constant and using the proportionality factors listed above, the number of windows for various genomic regions of interest can be calculated.

The above procedure can be applied to determine an average discretization. It also can be used to calculate a sample specific discretization by taking into account the sample specific analyte complexity, such as fetal fraction. This complexity can be obtained from either other experimental data (e.g., a fetal quantifier assay) or from the sequencing data itself to be discretized. For the latter case, an iterative approach can be taken: starting with a predefined grid, the sample complexity is first estimated (e.g., fetal fraction can be estimated using the BFF algorithm (e.g., portion-specific fetal fraction estimation, as described herein)). A statistical calculation can then be carried out to estimate a confidence interval for this value. Either the point estimate for this value or the confidence interval can then be used to recalculate the optimal discretization as described above.

Figure 9:
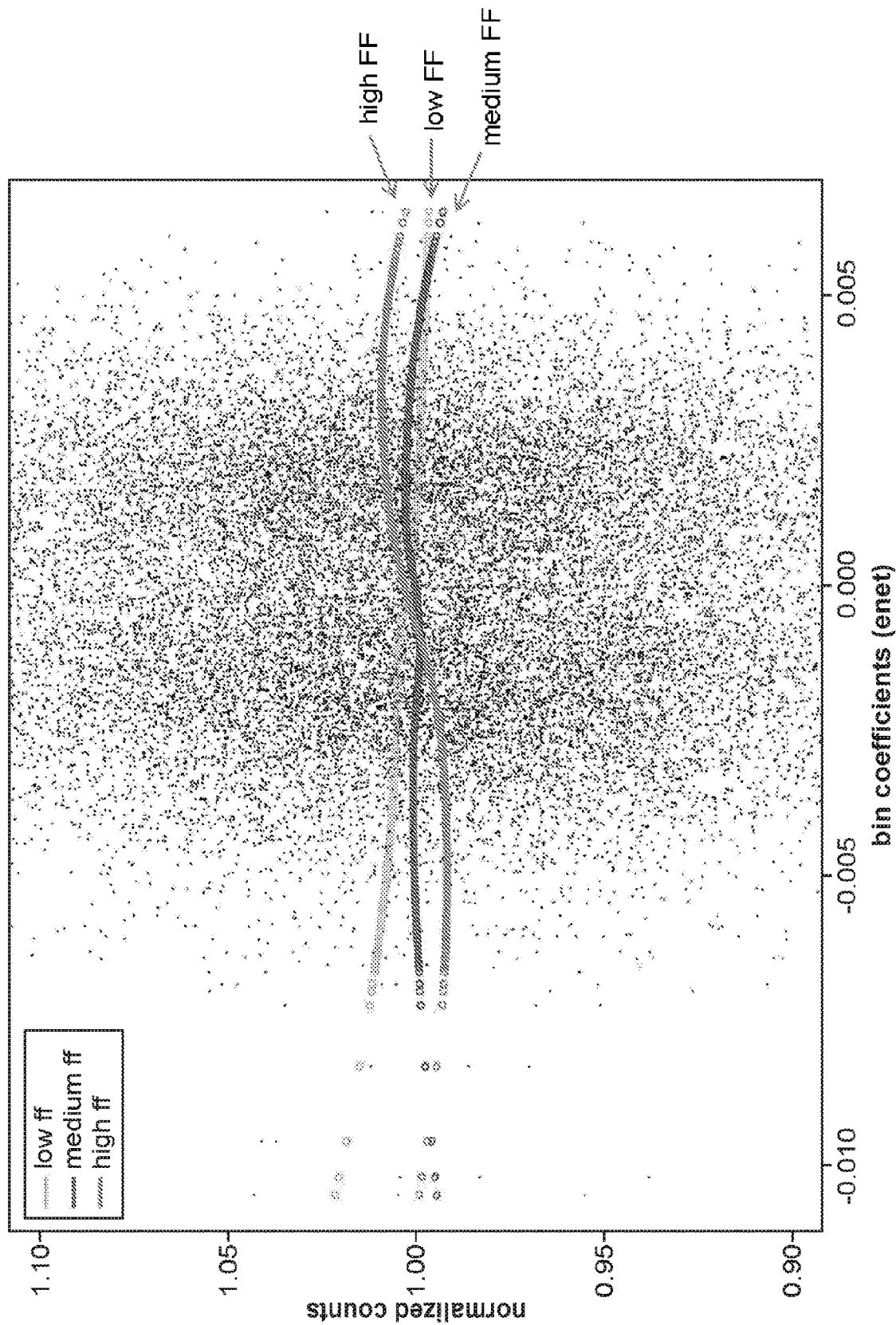
FIG. 9 shows a LOESS regression plot of normalized counts vs. enet bin coefficients (excluding bins with 0 coefficient) for three samples. Sample 1 had low fetal fraction (about 5%), sample 2 had medium fetal fraction (about 10%), and sample 3 had high fetal fraction (about 20%).

In addition to variability in sequencing coverage from one region to another, in certain instances there will be variability in local analyte complexity when considered in the context of genomic regions. For example, in NIPT samples where the analyte is a mixture of maternal and fetal ccfDNA, there can be differences in the fetal fraction associated with some genomic regions when compared to other regions. FIG. 9 shows a LOESS regression plot of normalized counts vs. enet (BFF; portion-specific fetal fraction) bin coefficients (excluding bins with 0 coefficient) for three samples. Sample 1 had low fetal fraction (about 5%), sample 2 had medium fetal fraction (about 10%), and sample 3 had high fetal fraction (about 20%). This plot highlights differences in coverage as a function of enet (BFF; portion-specific fetal fraction) bin coefficients and fetal fraction and supports the observation that certain regions provide more fetal DNA than other regions. Thus, a finer grid for example, can be constructed for regions providing more fetal DNA, and a coarse grid can be constructed for regions providing less fetal DNA.

The above described discretization method can be further refined by accounting for region-related variability in analyte complexity by repeating the LoD calculation using a local estimate of, e.g., fetal fraction. Sample specific discretization also can be accomplished by first estimating the sequencing depth (using the total number of reads) and then carrying out the calculations described above.

Figure 10:
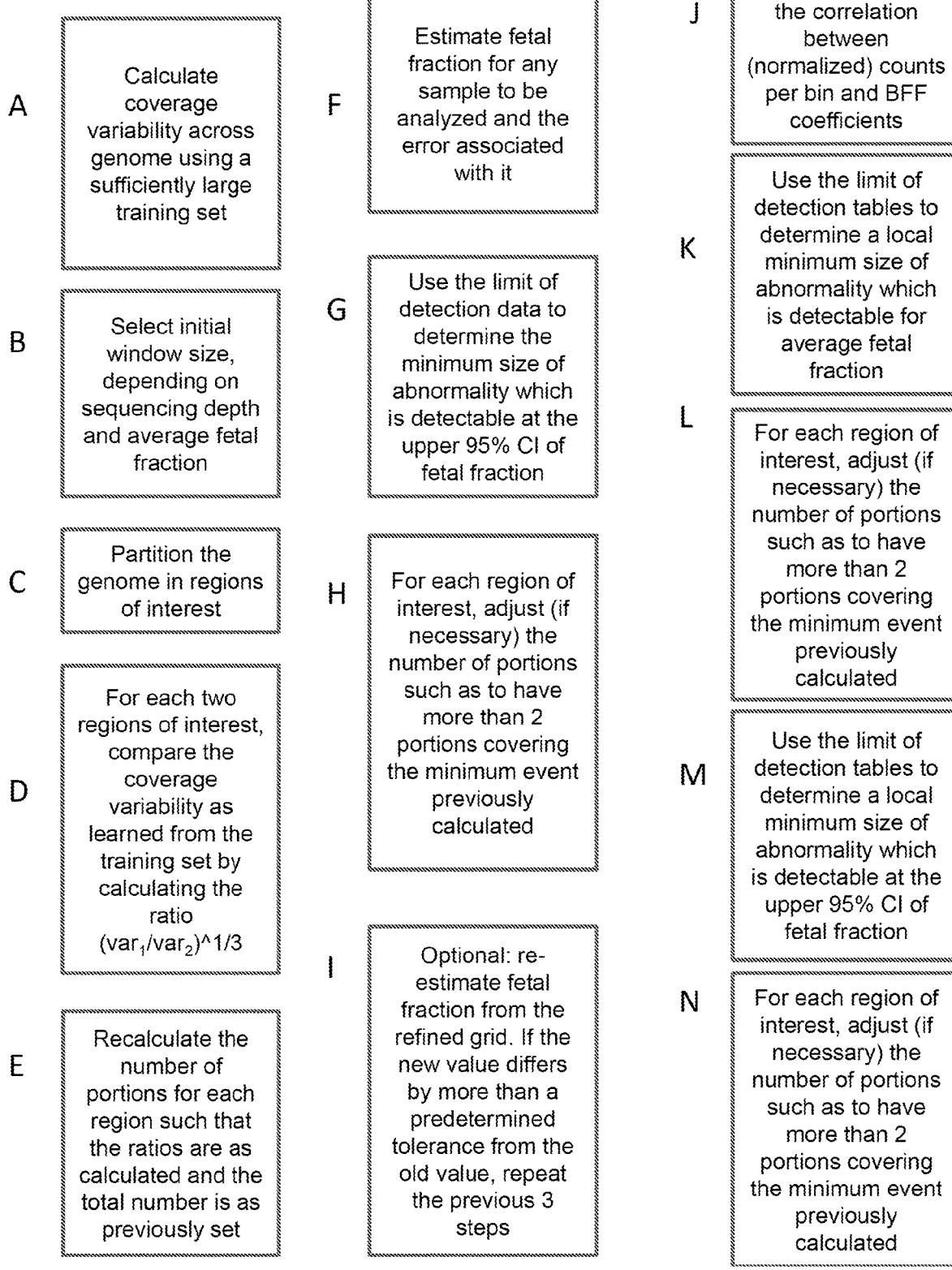
FIG. 10 shows certain steps that can be used in an optimal discretization method.

FIG. 10 shows certain steps that can be used in an optimal discretization method, and FIG. 11 shows example workflows for an optimal discretization method using certain steps presented in FIG. 10.

Example 3: Examples of Embodiments

A1. A method for partitioning one or more genomic regions of a reference genome into a plurality of portions comprising:
   a) determining sequencing coverage variability across a reference genome;
   b) selecting an initial portion length;
   c) partitioning at least two genomic regions according to the initial portion length in (b);
   d) comparing the sequencing coverage variability determined in (a) for each of the at least two genomic regions, thereby generating a comparison;

e) recalculating the number of portions for at least one of the genomic regions according to the comparison in (d), thereby determining an optimized portion length; and f) re-partitioning at least one of the genomic regions into a plurality of portions according to the optimized portion length in (e).

A1.1 A method for identifying the presence or absence of a genetic variation comprising quantifying nucleotide sequence reads for a test sample, which sequence reads are mapped to one or more genomic regions of a reference genome that have been partitioned by a process comprising:

a) determining sequencing coverage variability across a reference genome;

b) selecting an initial portion length;

c) partitioning at least two genomic regions according to the initial portion length in (b);

d) comparing the sequencing coverage variability determined in (a) for each of the at least two genomic regions, thereby generating a comparison;

e) recalculating the number of portions for at least one of the genomic regions according to the comparison in (d), thereby determining an optimized portion length; and f) re-partitioning at least one of the genomic regions into a plurality of portions according to the optimized portion length in (e).

A2. The method of embodiment A1 or A1.1, wherein determining the sequencing coverage variability in (a) comprises use of a training set of nucleotide sequence reads mapped to portions of a reference genome, which sequence reads are reads of circulating cell-free nucleic acid from a plurality of samples from pregnant females bearing a fetus.

A3. The method of embodiment A2, wherein the initial portion length in (b) is selected according to sequencing depth for the training set.

A4. The method of embodiment A2 or A3, wherein the initial portion length in (b) is selected according to an average fetal fraction for the training set.

A5. The method of embodiment A4, wherein the average fetal fraction is determined using the training set.

A6. The method of any one of embodiments A1 to A5, wherein the initial portion length is between about 1 kb to about 1000 kb.

A7. The method of any one of embodiments A1 to A6, wherein the initial portion length is about 30 kb.

A8. The method of any one of embodiments A1 to A6, wherein the initial portion length is about 40 kb.

A9. The method of any one of embodiments A1 to A6, wherein the initial portion length is about 50 kb.

A9.1 The method of any one of embodiments A1 to A6, wherein the initial portion length is not 50 kb.

A10. The method of any one of embodiments A1 to A6, wherein the initial portion length is about 60 kb.

A11. The method of any one of embodiments A1 to A6, wherein the initial portion length is about 70 kb.

A11.1 The method of any one of embodiments A1 to A11, wherein a total number of portions for a genome is determined according to the initial portion length in (b).

A12. The method of any one of embodiments A1 to A11.1, wherein the at least two genomic regions comprise a first genomic region and a second genomic region.

A13. The method of embodiment A12, wherein the first genomic region and the second genomic region are substantially similar in size.

A14. The method of embodiment A12 or A13, wherein comparing the sequencing coverage variability in (d) comprises calculating a proportionality factor (P) according to the following equation:

$$P = (\text{var}_1/\text{var}_2)^{1/3} \qquad \text{equation A}$$

wherein $\text{var}_1$ is the sequencing coverage variability of the first genomic region and $\text{var}_2$ is the sequencing coverage variability of the second genomic region.

A15. The method of embodiment A14, wherein the sequencing coverage variability of the first genomic region is determined from a nucleotide sequence read count, or a derivative thereof, for the first genomic region, and wherein sequencing coverage variability of the second genomic region is determined from a nucleotide sequence read count, or a derivative thereof, for the second genomic region.

A16. The method of embodiment A14, wherein the sequencing coverage variability of the first genomic region is determined from an average nucleotide sequence read count, or a derivative thereof, for the first genomic region, and wherein sequencing coverage variability of the second genomic region is determined from an average nucleotide sequence read count, or a derivative thereof, for the second genomic region.

A17. The method of embodiment A16, wherein the average nucleotide sequencing read counts for each genomic region are determined using the training set.

A18. The method of embodiment A15, wherein the nucleotide sequence read count is a normalized nucleotide sequence read count.

A19. The method of embodiment A16 or A17, wherein the average nucleotide sequence read count is an average normalized nucleotide sequence read count.

A20. The method of any one of embodiments A14 to A19, wherein the recalculating the number of portions for at least one of the genomic region in (e) is performed according to the proportionality factor and the total number of portions determined from the initial portion length in (b).

A21. The method of any one of embodiments A1 to A20, wherein the plurality of portions in (f) comprises portions of constant size.

A22. The method of any one of embodiments A1 to A20, wherein the plurality of portions in (f) comprises portions of varying size.

A23. The method of embodiment A21 or A22, wherein the plurality of portions in (f) comprises portion lengths of between about 1 kb to about 1000 kb.

A24. The method of embodiment A21 or A22, wherein the plurality of portions in (f) comprises portions of about 30 kb.

A25. The method of embodiment A21 or A22, wherein the plurality of portions in (f) comprises portions of about 40 kb.

A26. The method of embodiment A21 or A22, wherein the plurality of portions in (f) comprises portions of about 50 kb.

A27. The method of embodiment A21 or A22, wherein the plurality of portions in (f) does not comprise 50 kb portions.

A28. The method of embodiment A21 or A22, wherein the plurality of portions in (f) comprises portions of about 60 kb.

A29. The method of embodiment A21 or A22, wherein the plurality of portions in (f) comprises portions of about 70 kb.

A30. The method of any one of embodiments A1 to A29, comprising sequencing nucleic acid from a test sample by a nucleotide sequencing process to generate nucleotide sequence reads.

A31. The method of embodiment A30, wherein the nucleic acid is circulating cell-free nucleic acid from a pregnant female bearing a fetus.

A32. The method of any one of embodiments A1 to A31, comprising mapping nucleotide sequence reads from a test sample to re-partitioned portions of a reference genome, thereby generating mapped nucleotide sequence reads.

A33. The method of embodiment A32, comprising normalizing counts of the mapped nucleotide sequence reads, thereby generating normalized counts.

A34. The method of embodiment A33, wherein the normalizing comprises LOESS normalization of guanine and cytosine (GC) bias (GC-LOESS normalization).

A35. The method of embodiment A33 or A34, wherein the normalizing comprises adjusting a sequence read count according to a median count.

A35.1 The method of embodiment A35, wherein the sequence read count is adjusted according to a median portion count.

A36. The method of any one of embodiments A33 to A35.1, wherein the normalizing comprises a principal component normalization.

A37. The method of any one of embodiments A33 to A36, wherein the normalizing comprises GC-LOESS normalization followed by normalization according to a median portion count followed by a principal component normalization.

A38. The method of any one of embodiments A33 to A37, comprising determining the presence or absence of a genetic variation for the test sample according to the normalized counts.

A38.1 The method of any one of embodiments A33 to A38, comprising determining a chromosome structure according to the normalized counts.

A38.2 The method of any one of embodiments A33 to A38.1, wherein the normalized counts are representative of chromosome dosage for the test sample.

A38.3 The method of embodiment A38.2, wherein determining a presence or absence of a genetic variation is according to the chromosome dosage.

A38.4 The method of any one of embodiments A38 to A38.3, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

A39. The method of embodiment A32, wherein the method does not comprise normalizing counts of the mapped nucleotide sequence reads.

A40. The method of embodiment A39, comprising determining the presence or absence of a genetic variation for the test sample according to raw counts of the mapped nucleotide sequence reads.

A41. The method of embodiment A39 or A40, comprising determining a chromosome structure according to raw counts of the mapped nucleotide sequence reads.

A42. The method of embodiment A40 or A41, wherein the raw counts are representative of chromosome dosage for the test sample.

A43. The method of embodiment A42, wherein determining a presence or absence of a genetic variation is according to the chromosome dosage.

A44. The method of any one of embodiments A40 to A43, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

B1. A method for partitioning one or more genomic regions of a reference genome into a plurality of portions comprising:
   a) determining sequencing coverage variability across a reference genome;
   b) selecting an initial portion length;
   c) partitioning at least two genomic regions according to the initial portion length in (b);
   d) comparing the sequencing coverage variability determined in (a) for each of the at least two genomic regions, thereby generating a comparison;
   e) recalculating the number of portions for at least one of the genomic regions according to the comparison in (d), thereby determining an optimized portion length;
   f) re-partitioning at least one of the genomic regions into a plurality of portions according to the optimized portion length in (e), thereby generating a re-partitioned genomic region;
   g) estimating fetal fraction for a test sample from a pregnant female bearing a fetus;
   h) determining a minimum genomic region size; and
   i) adjusting the number of portions for each genomic region to comprise at least two portions, thereby generating a refined re-partitioned genomic region.

B1.1 A method for identifying the presence or absence of a genetic variation comprising quantifying nucleotide sequence reads for a test sample, which sequence reads are mapped to one or more genomic regions of a reference genome that have been partitioned by a process comprising:
   a) determining sequencing coverage variability across a reference genome;
   b) selecting an initial portion length;
   c) partitioning at least two genomic regions according to the initial portion length in (b);
   d) comparing the sequencing coverage variability determined in (a) for each of the at least two genomic regions, thereby generating a comparison;
   e) recalculating the number of portions for at least one of the genomic regions according to the comparison in (d), thereby determining an optimized portion length;
   f) re-partitioning at least one of the genomic regions into a plurality of portions according to the optimized portion length in (e), thereby generating a re-partitioned genomic region;
   g) estimating fetal fraction for a test sample from a pregnant female bearing a fetus;
   h) determining a minimum genomic region size; and
   i) adjusting the number of portions for each genomic region to comprise at least two portions, thereby generating a refined re-partitioned genomic region.

B2. The method of embodiment B1 or B1.1, wherein determining the sequencing coverage variability in (a) comprises use of a training set of nucleotide sequence reads mapped to portions of a reference genome, which sequence reads are reads of circulating cell-free nucleic acid from a plurality of samples from pregnant females bearing a fetus.

B3. The method of embodiment B2, wherein the initial portion length in (b) is selected according to sequencing depth for the training set.

B4. The method of embodiment B2 or B3, wherein the initial portion length in (b) is selected according to an average fetal fraction for the training set.

B5. The method of embodiment B4, wherein the average fetal fraction is determined using the training set.

B6. The method of any one of embodiments B1 to B5, wherein the initial portion length is between about 1 kb to about 1000 kb.

B7. The method of any one of embodiments B1 to B6, wherein the initial portion length is about 30 kb.

B8. The method of any one of embodiments B1 to B6, wherein the initial portion length is about 40 kb.

B9. The method of any one of embodiments B1 to B6, wherein the initial portion length is about 50 kb.

B9.1 The method of any one of embodiments B1 to B6, wherein the initial portion length is not 50 kb.

B10. The method of any one of embodiments B1 to B6, wherein the initial portion length is about 60 kb.

B11. The method of any one of embodiments B1 to B6, wherein the initial portion length is about 70 kb.

B11.1 The method of any one of embodiments B1 to B11, wherein a total number of portions for a genome is determined according to the initial portion length in (b).

B12. The method of any one of embodiments B1 to B11.1, wherein the at least two genomic regions comprise a first genomic region and a second genomic region.

B13. The method of embodiment B12, wherein the first genomic region and the second genomic region are substantially similar in size.

B14. The method of embodiment B12 or B13, wherein comparing the sequencing coverage variability in (d) comprises calculating a proportionality factor (P) according to the following equation:

$$P=(\text{var}_1/\text{var}_2)^{1/3} \qquad \text{equation A}$$

wherein $\text{var}_1$ is the sequencing coverage variability of the first genomic region and $\text{var}_2$ is the sequencing coverage variability of the second genomic region.

B15. The method of embodiment B14, wherein the sequencing coverage variability of the first genomic region is determined from a nucleotide sequence read count, or a derivative thereof, for the first genomic region, and wherein sequencing coverage variability of the second genomic region is determined from a nucleotide sequence read count, or a derivative thereof, for the second genomic region.

B16. The method of embodiment B14, wherein the sequencing coverage variability of the first genomic region is determined from an average nucleotide sequence read count, or a derivative thereof, for the first genomic region, and wherein sequencing coverage variability of the second genomic region is determined from an average nucleotide sequence read count, or a derivative thereof, for the second genomic region.

B17. The method of embodiment B16, wherein the average nucleotide sequencing read counts for each genomic region are determined using the training set.

B18. The method of embodiment B15, wherein the nucleotide sequence read count is a normalized nucleotide sequence read count.

B19. The method of embodiment B16 or B17, wherein the average nucleotide sequence read count is an average normalized nucleotide sequence read count.

B20. The method of any one of embodiments B14 to B19, wherein the recalculating the number of portions for at least one of the genomic region in (e) is performed according to the proportionality factor and the total number of portions determined from the initial portion length in (b).

B21. The method of any one of embodiments B1 to B20, wherein the plurality of portions in (f) comprises portions of constant size.

B22. The method of any one of embodiments B1 to B20, wherein the plurality of portions in (f) comprises portions of varying size.

B23. The method of embodiment B21 or B22, wherein the plurality of portions in (f) comprises portion lengths of between about 1 kb to about 1000 kb.

B24. The method of embodiment B21 or B22, wherein the plurality of portions in (f) comprises portions of about 30 kb.

B25. The method of embodiment B21 or B22, wherein the plurality of portions in (f) comprises portions of about 40 kb.

B26. The method of embodiment B21 or B22, wherein the plurality of portions in (f) comprises portions of about 50 kb.

B27. The method of embodiment B21 or B22, wherein the plurality of portions in (f) does not comprise 50 kb portions.

B28. The method of embodiment B21 or B22, wherein the plurality of portions in (f) comprises portions of about 60 kb.

B29. The method of embodiment B21 or B22, wherein the plurality of portions in (f) comprises portions of about 70 kb.

B30. The method of any one of embodiments B1 to B29, wherein estimating fetal fraction in (g) comprises determining an error value.

B31. The method of any one of embodiments B1 to B30, wherein determining a minimum genomic region size in (h) comprises determining a minimum genomic region size that is detectable for a sample having a fetal fraction as estimated in (g).

B32. The method of embodiment B31, wherein a minimum genomic region size is determined according to an upper 95% confidence interval of fetal fraction.

B33. The method of any one of embodiments B1 to B32, further comprising (j) re-estimating fetal fraction from the refined re-partitioned genomic region.

B34. The method of embodiment B33, comprising comparing the estimated fetal fraction in (g) to the re-estimated fetal fraction in (j).

B35. The method of embodiment B34, comprising repeating parts (g), (h) and (i) when the estimated fetal fraction in (g) differs from the re-estimated fetal fraction in (j) by a predetermined tolerance value.

B35.1 The method of embodiment B35, wherein the predetermined tolerance value is between about 1% to about 25%.

B36. The method of any one of embodiments B1 to B35.1, comprising sequencing nucleic acid from a test sample by a nucleotide sequencing process to generate nucleotide sequence reads.

B37. The method of embodiment B36, wherein the nucleic acid is circulating cell-free nucleic acid from a pregnant female bearing a fetus.

B38. The method of any one of embodiments B1 to B37, comprising mapping nucleotide sequence reads from a test sample to refined re-partitioned portions of a reference genome, thereby generating mapped nucleotide sequence reads.

B39. The method of embodiment B38, comprising normalizing counts of the mapped nucleotide sequence reads, thereby generating normalized counts.

B40. The method of embodiment B39, wherein the normalizing comprises LOESS normalization of guanine and cytosine (GC) bias (GC-LOESS normalization).

B41. The method of embodiment B39 or B40, wherein the normalizing comprises adjusting a sequence read count according to a median count.

B41.1 The method of embodiment B41, wherein the sequence read count is adjusted according to a median portion count.

B42. The method of any one of embodiments B39 to B41.1, wherein the normalizing comprises a principal component normalization.

B43. The method of any one of embodiments B39 to B42, wherein the normalizing comprises GC-LOESS normalization followed by normalization according to a median portion count followed by a principal component normalization.

B44. The method of any one of embodiments B39 to B43, comprising determining the presence or absence of a genetic variation for the test sample according to the normalized counts.

B44.1 The method of any one of embodiments B39 to B44, comprising determining a chromosome structure according to the normalized counts.

B44.2 The method of any one of embodiments B39 to B44.1, wherein the normalized counts are representative of chromosome dosage for the test sample.

B44.3 The method of embodiment B44.2, wherein determining a presence or absence of a genetic variation is according to the chromosome dosage.

B44.4 The method of any one of embodiments B44 to B44.3, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

B45. The method of embodiment B38, wherein the method does not comprise normalizing counts of the mapped nucleotide sequence reads.

B46. The method of embodiment B45, comprising determining the presence or absence of a genetic variation for the test sample according to raw counts of the mapped nucleotide sequence reads.

B47. The method of embodiment B45 of B46, comprising determining a chromosome structure according to raw counts of the mapped nucleotide sequence reads.

B48. The method of embodiment B46 or B47, wherein the raw counts are representative of chromosome dosage for the test sample.

B49. The method of embodiment B48, wherein determining a presence or absence of a genetic variation is according to the chromosome dosage.

B50. The method of any one of embodiments B46 to B49, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

C1. A method for partitioning one or more genomic regions of a reference genome into a plurality of portions comprising:
  a) determining sequencing coverage variability across a reference genome;
  b) selecting an initial portion length;
  c) partitioning at least two genomic regions according to the initial portion length in (b);
  d) comparing the sequencing coverage variability determined in (a) for each of the at least two genomic regions, thereby generating a comparison;
  e) recalculating the number of portions for at least one of the genomic regions according to the comparison in (d), thereby determining an optimized portion length;
  f) re-partitioning at least one of the genomic regions into a plurality of portions according to the optimized portion length in (e), thereby generating a re-partitioned genomic region;
  g) determining a region-specific fetal fraction for each genomic region according to a correlation between nucleotide sequence read counts per portion and a weighting factor;
  h) determining a local minimum genomic region size; and
  i) adjusting the number of portions for each genomic region to comprise at least two portions, thereby generating a refined re-partitioned genomic region.

C1.1 A method for identifying the presence or absence of a genetic variation comprising quantifying nucleotide sequence reads for a test sample, which sequence reads are mapped to one or more genomic regions of a reference genome that have been partitioned by a process comprising:
  a) determining sequencing coverage variability across a reference genome;
  b) selecting an initial portion length;
  c) partitioning at least two genomic regions according to the initial portion length in (b);
  d) comparing the sequencing coverage variability determined in (a) for each of the at least two genomic regions, thereby generating a comparison;
  e) recalculating the number of portions for at least one of the genomic regions according to the comparison in (d), thereby determining an optimized portion length;
  f) re-partitioning at least one of the genomic regions into a plurality of portions according to the optimized portion length in (e), thereby generating a re-partitioned genomic region;
  g) determining a region-specific fetal fraction for each genomic region according to a correlation between nucleotide sequence read counts per portion and a weighting factor;
  h) determining a local minimum genomic region size; and
  i) adjusting the number of portions for each genomic region to comprise at least two portions, thereby generating a refined re-partitioned genomic region.

C2. The method of embodiment C1 or C1.1, wherein determining the sequencing coverage variability in (a) comprises use of a training set of nucleotide sequence reads mapped to portions of a reference genome, which sequence reads are reads of circulating cell-free nucleic acid from a plurality of samples from pregnant females bearing a fetus.

C3. The method of embodiment C2, wherein the initial portion length in (b) is selected according to sequencing depth for the training set.

C4. The method of embodiment C2 or C3, wherein the initial portion length in (b) is selected according to an average fetal fraction for the training set.

C5. The method of embodiment C4, wherein the average fetal fraction is determined using the training set.

C6. The method of any one of embodiments C1 to C5, wherein the initial portion length is between about 1 kb to about 1000 kb.

C7. The method of any one of embodiments C1 to C6, wherein the initial portion length is about 30 kb.

C8. The method of any one of embodiments C1 to C6, wherein the initial portion length is about 40 kb.

C9. The method of any one of embodiments C1 to C6, wherein the initial portion length is about 50 kb.

C9.1 The method of any one of embodiments C1 to C6, wherein the initial portion length is not 50 kb.

C10. The method of any one of embodiments C1 to C6, wherein the initial portion length is about 60 kb.

C11. The method of any one of embodiments C1 to C6, wherein the initial portion length is about 70 kb.

C11.1 The method of any one of embodiments C1 to C11, wherein a total number of portions for a genome is determined according to the initial portion length in (b).

C12. The method of any one of embodiments C1 to C11.1, wherein the at least two genomic regions comprise a first genomic region and a second genomic region.

C13. The method of embodiment C12, wherein the first genomic region and the second genomic region are substantially similar in size.

C14. The method of embodiment C12 or C13, wherein comparing the sequencing coverage variability in (d) comprises calculating a proportionality factor (P) according to the following equation:

$$P = (var_1/var_2)^{1/3} \qquad \text{equation A}$$

wherein $var_1$ is the sequencing coverage variability of the first genomic region and $var_2$ is the sequencing coverage variability of the second genomic region.

C15. The method of embodiment C14, wherein the sequencing coverage variability of the first genomic region is determined from a nucleotide sequence read count, or a derivative thereof, for the first genomic region, and wherein sequencing coverage variability of the second genomic region is determined from a nucleotide sequence read count, or a derivative thereof, for the second genomic region.

C16. The method of embodiment C14, wherein the sequencing coverage variability of the first genomic region is determined from an average nucleotide sequence read count, or a derivative thereof, for the first genomic region, and wherein sequencing coverage variability of the second genomic region is determined from an average nucleotide sequence read count, or a derivative thereof, for the second genomic region.

C17. The method of embodiment C16, wherein the average nucleotide sequencing read counts for each genomic region are determined using the training set.

C18. The method of embodiment C15, wherein the nucleotide sequence read count is a normalized nucleotide sequence read count.

C19. The method of embodiment C16 or C17, wherein the average nucleotide sequence read count is an average normalized nucleotide sequence read count.

C20. The method of any one of embodiments C14 to C19, wherein the recalculating the number of portions for at least one of the genomic region in (e) is performed according to the proportionality factor and the total number of portions determined from the initial portion length in (b).

C21. The method of any one of embodiments C1 to C20, wherein the plurality of portions in (f) comprises portions of constant size.

C22. The method of any one of embodiments C1 to C20, wherein the plurality of portions in (f) comprises portions of varying size.

C23. The method of embodiment C21 or C22, wherein the plurality of portions in (f) comprises portion lengths of between about 1 kb to about 1000 kb.

C24. The method of embodiment C21 or C22, wherein the plurality of portions in (f) comprises portions of about 30 kb.

C25. The method of embodiment C21 or C22, wherein the plurality of portions in (f) comprises portions of about 40 kb.

C26. The method of embodiment C21 or C22, wherein the plurality of portions in (f) comprises portions of about 50 kb.

C27. The method of embodiment C21 or C22, wherein the plurality of portions in (f) does not comprise 50 kb portions.

C28. The method of embodiment C21 or C22, wherein the plurality of portions in (f) comprises portions of about 60 kb.

C29. The method of embodiment C21 or C22, wherein the plurality of portions in (f) comprises portions of about 70 kb.

C30. The method of any one of embodiments C1 to C29, wherein determining a local minimum genomic region size in (h) comprises determining a local genomic region size that is detectable for a sample having an average fetal fraction.

C31. The method of any one of embodiments C1 to C30, comprising sequencing nucleic acid from a test sample by a nucleotide sequencing process to generate nucleotide sequence reads.

C32. The method of embodiment C31, wherein the nucleic acid is circulating cell-free nucleic acid from a pregnant female bearing a fetus.

C33. The method of any one of embodiments C1 to C32, comprising mapping nucleotide sequence reads from a test sample to refined re-partitioned portions of a reference genome, thereby generating mapped nucleotide sequence reads.

C34. The method of embodiment C33, comprising normalizing counts of the mapped nucleotide sequence reads, thereby generating normalized counts.

C35. The method of embodiment C34, wherein the normalizing comprises LOESS normalization of guanine and cytosine (GC) bias (GC-LOESS normalization).

C36. The method of embodiment C34 or C35, wherein the normalizing comprises adjusting a sequence read count according to a median count.

C36.1 The method of embodiment C36, wherein the sequence read count is adjusted according to a median portion count.

C37. The method of any one of embodiments C34 to C36.1, wherein the normalizing comprises a principal component normalization.

C38. The method of any one of embodiments C34 to C37, wherein the normalizing comprises GC-LOESS normalization followed by normalization according to a median portion count followed by a principal component normalization.

C39. The method of any one of embodiments C34 to C38, comprising determining the presence or absence of a genetic variation for the test sample according to the normalized counts.

C39.1 The method of any one of embodiments C34 to C39, comprising determining a chromosome structure according to the normalized counts.

C39.2 The method of any one of embodiments C34 to C39.1, wherein the normalized counts are representative of chromosome dosage for the test sample.

C39.3 The method of embodiment C39.2, wherein determining a presence or absence of a genetic variation is according to the chromosome dosage.

C39.4 The method of any one of embodiments C39 to C39.3, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

C40. The method of embodiment C33, wherein the method does not comprise normalizing counts of the mapped nucleotide sequence reads.

C41. The method of embodiment C40, comprising determining the presence or absence of a genetic variation for the test sample according to raw counts of the mapped nucleotide sequence reads.

C42. The method of embodiment C40 or C41, comprising determining a chromosome structure according to raw counts of the mapped nucleotide sequence reads.

C43. The method of embodiment C41 or C42, wherein the raw counts are representative of chromosome dosage for the test sample.

C44. The method of embodiment C43, wherein determining a presence or absence of a genetic variation is according to the chromosome dosage.

C45. The method of any one of embodiments C41 to C44, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

D1. A method for partitioning one or more genomic regions of a reference genome into a plurality of portions comprising:
 a) determining sequencing coverage variability across a reference genome;
 b) selecting an initial portion length;
 c) partitioning at least two genomic regions according to the initial portion length in (b);
 d) comparing the sequencing coverage variability determined in (a) for each of the at least two genomic regions, thereby generating a comparison;
 e) recalculating the number of portions for at least one of the genomic regions according to the comparison in (d), thereby determining an optimized portion length;
 f) re-partitioning at least one of the genomic regions into a plurality of portions according to the optimized portion length in (e), thereby generating a re-partitioned genomic region;
 g) estimating fetal fraction for a test sample from a pregnant female bearing a fetus;
 h) determining a region-specific fetal fraction for each genomic region according to a correlation between nucleotide sequence read counts per portion and a weighting factor;
 i) determining a local minimum genomic region size; and
 j) adjusting the number of portions for each genomic region to comprise at least two portions, thereby generating a refined re-partitioned genomic region.

D1.1 A method for identifying the presence or absence of a genetic variation comprising quantifying nucleotide sequence reads for a test sample, which sequence reads are mapped to one or more genomic regions of a reference genome that have been partitioned by a process comprising:
 a) determining sequencing coverage variability across a reference genome;
 b) selecting an initial portion length;
 c) partitioning at least two genomic regions according to the initial portion length in (b);
 d) comparing the sequencing coverage variability determined in (a) for each of the at least two genomic regions, thereby generating a comparison;
 e) recalculating the number of portions for at least one of the genomic regions according to the comparison in (d), thereby determining an optimized portion length;
 f) re-partitioning at least one of the genomic regions into a plurality of portions according to the optimized portion length in (e), thereby generating a re-partitioned genomic region;
 g) estimating fetal fraction for a test sample from a pregnant female bearing a fetus;
 h) determining a region-specific fetal fraction for each genomic region according to a correlation between nucleotide sequence read counts per portion and a weighting factor;
 i) determining a local minimum genomic region size; and
 j) adjusting the number of portions for each genomic region to comprise at least two portions, thereby generating a refined re-partitioned genomic region.

D2. The method of embodiment D1 or D1.1, wherein determining the sequencing coverage variability in (a) comprises use of a training set of nucleotide sequence reads mapped to portions of a reference genome, which sequence reads are reads of circulating cell-free nucleic acid from a plurality of samples from pregnant females bearing a fetus.

D3. The method of embodiment D2, wherein the initial portion length in (b) is selected according to sequencing depth for the training set.

D4. The method of embodiment D2 or D3, wherein the initial portion length in (b) is selected according to an average fetal fraction for the training set.

D5. The method of embodiment D4, wherein the average fetal fraction is determined using the training set.

D6. The method of any one of embodiments D1 to D5, wherein the initial portion length is between about 1 kb to about 1000 kb.

D7. The method of any one of embodiments D1 to D6, wherein the initial portion length is about 30 kb.

D8. The method of any one of embodiments D1 to D6, wherein the initial portion length is about 40 kb.

D9. The method of any one of embodiments D1 to D6, wherein the initial portion length is about 50 kb.

D9.1 The method of any one of embodiments D1 to D6, wherein the initial portion length is not 50 kb.

D10. The method of any one of embodiments D1 to D6, wherein the initial portion length is about 60 kb.

D11. The method of any one of embodiments D1 to D6, wherein the initial portion length is about 70 kb.

D11.1 The method of any one of embodiments D1 to D11, wherein a total number of portions for a genome is determined according to the initial portion length in (b).

D12. The method of any one of embodiments D1 to D11.1, wherein the at least two genomic regions comprise a first genomic region and a second genomic region.

D13. The method of embodiment D12, wherein the first genomic region and the second genomic region are substantially similar in size.

D14. The method of embodiment D12 or D13, wherein comparing the sequencing coverage variability in (d) comprises calculating a proportionality factor (P) according to the following equation:

$$P = (\text{var}_1/\text{var}_2)^{1/3} \qquad \text{equation A}$$

wherein $\text{var}_1$ is the sequencing coverage variability of the first genomic region and $\text{var}_2$ is the sequencing coverage variability of the second genomic region.

D15. The method of embodiment D14, wherein the sequencing coverage variability of the first genomic region is determined from a nucleotide sequence read count, or a derivative thereof, for the first genomic region, and wherein sequencing coverage variability of the second genomic region is determined from a nucleotide sequence read count, or a derivative thereof, for the second genomic region.

D16. The method of embodiment D14, wherein the sequencing coverage variability of the first genomic region is determined from an average nucleotide sequence read count, or a derivative thereof, for the first genomic region, and wherein sequencing coverage variability of the second genomic region is determined from an average nucleotide sequence read count, or a derivative thereof, for the second genomic region.

D17. The method of embodiment D16, wherein the average nucleotide sequencing read counts for each genomic region are determined using the training set.

D18. The method of embodiment D15, wherein the nucleotide sequence read count is a normalized nucleotide sequence read count.

D19. The method of embodiment D16 or D17, wherein the average nucleotide sequence read count is an average normalized nucleotide sequence read count.

D20. The method of any one of embodiments D14 to D19, wherein the recalculating the number of portions for at least one of the genomic region in (e) is performed according to the proportionality factor and the total number of portions determined from the initial portion length in (b).

D21. The method of any one of embodiments D1 to D20, wherein the plurality of portions in (f) comprises portions of constant size.

D22. The method of any one of embodiments D1 to D20, wherein the plurality of portions in (f) comprises portions of varying size.

D23. The method of embodiment D21 or D22, wherein the plurality of portions in (f) comprises portion lengths of between about 1 kb to about 1000 kb.

D24. The method of embodiment D21 or D22, wherein the plurality of portions in (f) comprises portions of about 30 kb.

D25. The method of embodiment D21 or D22, wherein the plurality of portions in (f) comprises portions of about 40 kb.

D26. The method of embodiment D21 or D22, wherein the plurality of portions in (f) comprises portions of about 50 kb.

D27. The method of embodiment D21 or D22, wherein the plurality of portions in (f) does not comprise 50 kb portions.

D28. The method of embodiment D21 or D22, wherein the plurality of portions in (f) comprises portions of about 60 kb.

D29. The method of embodiment D21 or D22, wherein the plurality of portions in (f) comprises portions of about 70 kb.

D30. The method of any one of embodiments D1 to D29, wherein estimating fetal fraction in (g) comprises determining an error value.

D31. The method of any one of embodiments D1 to D30, wherein determining a local minimum genomic region size in (i) comprises determining a minimum local genomic region size that is detectable for a sample having a fetal fraction as estimated in (g).

D32. The method of embodiment D31, wherein a local minimum genomic region size is determined according to an upper 95% confidence interval of fetal fraction.

D33. The method of any one of embodiments D1 to D32, further comprising (k) re-estimating fetal fraction from the refined re-partitioned genomic region.

D34. The method of embodiment D33, comprising comparing the estimated fetal fraction in (g) to the re-estimated fetal fraction in (k).

D35. The method of embodiment D34, comprising repeating parts (g), (h), (i) and (j) when the estimated fetal fraction in (g) differs from the re-estimated fetal fraction in (k) by a predetermined tolerance value.

D35.1 The method of embodiment D35, wherein the predetermined tolerance value is between about 1% to about 25%.

D36. The method of any one of embodiments D1 to D35.1, comprising sequencing nucleic acid from a test sample by a nucleotide sequencing process to generate nucleotide sequence reads.

D37. The method of embodiment D36, wherein the nucleic acid is circulating cell-free nucleic acid from a pregnant female bearing a fetus.

D38. The method of any one of embodiments D1 to D37, comprising mapping nucleotide sequence reads from a test sample to refined re-partitioned portions of a reference genome, thereby generating mapped nucleotide sequence reads.

D39. The method of embodiment D38, comprising normalizing counts of the mapped nucleotide sequence reads, thereby generating normalized counts.

D40. The method of embodiment D39, wherein the normalizing comprises LOESS normalization of guanine and cytosine (GC) bias (GC-LOESS normalization).

D41. The method of embodiment D39 or D40, wherein the normalizing comprises adjusting a sequence read count according to a median count.

D41.1 The method of embodiment D41, wherein the sequence read count is adjusted according to a median portion count.

D42. The method of any one of embodiments D39 to D41.1, wherein the normalizing comprises a principal component normalization.

D43. The method of any one of embodiments D39 to D42, wherein the normalizing comprises GC-LOESS normalization followed by normalization according to a median portion count followed by a principal component normalization.

D44. The method of any one of embodiments D39 to D43, comprising determining the presence or absence of a genetic variation for the test sample according to the normalized counts.

D44.1 The method of any one of embodiments D39 to D44, comprising determining a chromosome structure according to the normalized counts.

D44.2 The method of any one of embodiments D39 to D44.1, wherein the normalized counts are representative of chromosome dosage for the test sample.

D44.3 The method of embodiment D44.2, wherein determining a presence or absence of a genetic variation is according to the chromosome dosage.

D44.4 The method of any one of embodiments D44 to D44.3, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

D45. The method of embodiment D38, wherein the method does not comprise normalizing counts of the mapped nucleotide sequence reads.

D46. The method of embodiment D45, comprising determining the presence or absence of a genetic variation for the test sample according to raw counts of the mapped nucleotide sequence reads.

D47. The method of embodiment D45 or D46, comprising determining a chromosome structure according to raw counts of the mapped nucleotide sequence reads.

D48. The method of embodiment D46 or D47, wherein the raw counts are representative of chromosome dosage for the test sample.

D49. The method of embodiment D48, wherein determining a presence or absence of a genetic variation is according to the chromosome dosage.

D50. The method of any one of embodiments D46 to D49, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

E1. A method for partitioning one or more genomic regions of a reference genome into a plurality of portions comprising:
  a) determining sequencing coverage variability across a reference genome;
  b) selecting an initial portion length;
  c) partitioning at least two genomic regions according to the initial portion length in (b);
  d) determining a region-specific fetal fraction for each genomic region according to a correlation between nucleotide sequence read counts per portion and a weighting factor;
  e) determining a local minimum genomic region size; and
  f) adjusting the number of portions for each genomic region to comprise at least two portions, thereby generating a re-partitioned genomic region.

E1.1 A method for identifying the presence or absence of a genetic variation comprising quantifying nucleotide sequence reads for a test sample, which sequence reads are mapped to one or more genomic regions of a reference genome that have been partitioned by a process comprising:
  a) determining sequencing coverage variability across a reference genome;
  b) selecting an initial portion length;
  c) partitioning at least two genomic regions according to the initial portion length in (b);
  d) determining a region-specific fetal fraction for each genomic region according to a correlation between nucleotide sequence read counts per portion and a weighting factor;
  e) determining a local minimum genomic region size; and
  f) adjusting the number of portions for each genomic region to comprise at least two portions, thereby generating a re-partitioned genomic region.

E2. The method of embodiment E1 or E1.1, wherein determining the sequencing coverage variability in (a) comprises use of a training set of nucleotide sequence reads mapped to portions of a reference genome, which sequence reads are reads of circulating cell-free nucleic acid from a plurality of samples from pregnant females bearing a fetus.

E3. The method of embodiment E1 or E2, wherein the initial portion length in (b) is selected according to sequencing depth.

E4. The method of embodiment E1, E2 or E3, wherein the initial portion length in (b) is selected according to an average fetal fraction.

E5. The method of embodiment E4, wherein the average fetal fraction is determined using the training set.

E6. The method of any one of embodiments E1 to E5, wherein the initial portion length is between about 1 kb to about 1000 kb.

E7. The method of any one of embodiments E1 to E6, wherein the initial portion length is about 30 kb.

E8. The method of any one of embodiments E1 to E6, wherein the initial portion length is about 40 kb.

E9. The method of any one of embodiments E1 to E6, wherein the initial portion length is about 50 kb.

E9.1 The method of any one of embodiments E1 to E6, wherein the initial portion length is not 50 kb.

E10. The method of any one of embodiments E1 to E6, wherein the initial portion length is about 60 kb.

E11. The method of any one of embodiments E1 to E6, wherein the initial portion length is about 70 kb.

E11.1 The method of any one of embodiments E1 to E11, wherein a total number of portions for a genome is determined according to the initial portion length in (b).

E12. The method of any one of embodiments E1 to E11.1, wherein the at least two genomic regions comprise a first genomic region and a second genomic region.

E13. The method of embodiment E12, wherein the first genomic region and the second genomic region are substantially similar in size.

E14. The method of any one of embodiments E1 to E13, wherein the re-partitioned genomic region in (f) comprises portions of constant size.

E15. The method of any one of embodiments E1 to E13, wherein the re-partitioned genomic region in (f) comprises portions of varying size.

E16. The method of embodiment E14 or E15, wherein the re-partitioned genomic region in (f) comprises portions having sizes of between about 1 kb to about 1000 kb.

E17. The method of embodiment E14 or E15, wherein the re-partitioned genomic region in (f) comprises portions having sizes of about 30 kb.

E18. The method of embodiment E14 or E15, wherein the re-partitioned genomic region in (f) comprises portions having sizes of about 40 kb.

E18.1 The method of embodiment E14 or E15, wherein the re-partitioned genomic region in (f) comprises portions having sizes of about 50 kb.

E19. The method of embodiment E14 or E15, wherein the re-partitioned genomic region does not comprise 50 kb portions.

E20. The method of embodiment E14 or E15, wherein the re-partitioned genomic region in (f) comprises portions having sizes of about 60 kb.

E21. The method of embodiment E14 or E15, wherein the re-partitioned genomic region in (f) comprises portions having sizes of about 70 kb.

E22. The method of any one of embodiments E1 to E21, wherein determining a local minimum genomic region size in (e) comprises identifying a local genomic region size that is detectable for a sample having an average fetal fraction.

E23. The method of any one of embodiments E1 to E22, further comprising (g) re-estimating fetal fraction from the re-partitioned genomic region.

E24. The method of embodiment E23, comprising comparing the region-specific fetal fraction in (d) to the re-estimated fetal fraction in (g).

E25. The method of embodiment E24, comprising repeating parts (d), (e) and (f) when the region-specific fetal fraction in (d) differs from the re-estimated fetal fraction in (g) by a predetermined tolerance value.

E25.1 The method of embodiment E25, wherein the predetermined tolerance value is between about 1% to about 25%.

E26. The method of any one of embodiments E1 to E25.1, comprising sequencing nucleic acid from a test sample by a nucleotide sequencing process to generate nucleotide sequence reads.

E27. The method of embodiment E26, wherein the nucleic acid is circulating cell-free nucleic acid from a pregnant female bearing a fetus.

E28. The method of any one of embodiments E1 to E27, comprising mapping nucleotide sequence reads from a test sample to re-partitioned portions of a reference genome, thereby generating mapped nucleotide sequence reads.

E29. The method of embodiment E28, comprising normalizing counts of the mapped nucleotide sequence reads, thereby generating normalized counts.

E30. The method of embodiment E29, wherein the normalizing comprises LOESS normalization of guanine and cytosine (GC) bias (GC-LOESS normalization).

E31. The method of embodiment E29 or E30, wherein the normalizing comprises adjusting a sequence read count according to a median count.

E31.1 The method of embodiment E31, wherein the sequence read count is adjusted according to a median portion count.

E32. The method of any one of embodiment E29 to E31.1, wherein the normalizing comprises a principal component normalization.

E33. The method of any one of embodiments E29 to E32, wherein the normalizing comprises GC-LOESS normalization followed by normalization according to a median portion count followed by a principal component normalization.

E34. The method of any one of embodiments E29 to E33, comprising determining the presence or absence of a genetic variation for the test sample according to the normalized counts.

E34.1 The method of any one of embodiments E29 to E34, comprising determining a chromosome structure according to the normalized counts.

E34.2 The method of any one of embodiments E29 to E34.1, wherein the normalized counts are representative of chromosome dosage for the test sample.

E34.3 The method of embodiment E34.2, wherein determining a presence or absence of a genetic variation is according to the chromosome dosage.

E34.4 The method of any one of embodiments E34 to E34.3, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

E35. The method of embodiment E28, wherein the method does not comprise normalizing counts of the mapped nucleotide sequence reads.

E36. The method of embodiment E35, comprising determining the presence or absence of a genetic variation for the test sample according to raw counts of the mapped nucleotide sequence reads.

E37. The method of embodiment E35 or E36, comprising determining a chromosome structure according to raw counts of the mapped nucleotide sequence reads.

E38. The method of embodiment E36 or E37, wherein the raw counts are representative of chromosome dosage for the test sample.

E39. The method of embodiment E38, wherein determining a presence or absence of a genetic variation is according to the chromosome dosage.

E40. The method of any one of embodiments E36 to E39, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

F1. A method for partitioning a reference genome, or part thereof, into a plurality of portions comprising:
  a) generating a guanine and cytosine (GC) profile for a reference genome, or part thereof;
  b) applying a segmenting process to the GC profile generated in (a), thereby providing discrete segments; and
  c) partitioning the reference genome, or part thereof, into a plurality of portions according to the discrete segments provided in (b), thereby generating a GC partitioned reference genome, or part thereof.

F1.1 A method for identifying the presence or absence of a genetic variation comprising quantifying nucleotide sequence reads for a test sample, which sequence reads are mapped to a reference genome, or part thereof, that has been partitioned by a process comprising:
  a) generating a guanine and cytosine (GC) profile for a reference genome, or part thereof;
  b) applying a segmenting process to the GC profile generated in (a), thereby providing discrete segments; and
  c) partitioning the a reference genome, or part thereof, into a plurality of portions according to the discrete segments provided in (b), thereby generating a GC partitioned reference genome, or part thereof.

F1.2 The method of embodiment F1 or F1.1, comprising partitioning a chromosome, or segment of a chromosome, from the reference genome, thereby generating a GC partitioned chromosome, or GC partitioned chromosome segment.

F2. The method of embodiment F1, F1.1 or F1.2, wherein the GC profile in (a) comprises GC content levels determined for each 1 kb of nucleotide sequence in the reference genome.

F3. The method of embodiment F2, wherein the segmenting process in (b) is performed on the GC content levels.

F4. The method of embodiment F3, wherein 1 kb nucleotide sequences having similar GC content levels are merged into the discrete segments.

F5. The method of any one of embodiments F1 to F4, wherein the segmenting process in (b) generates a decomposition rendering comprising the discrete segments.

F5.1 The method of any one of embodiments F1 to F5, wherein the segmenting process in (b) is performed according to a level of decomposition based on chromosome length ($L_{chr}$) and minimum portion length ($L_{min}$).

F6. The method of any one of embodiments F1 to F5.1, wherein the segmenting process in (b) comprises Haar wavelet segmentation.

F7. The method of any one of embodiments F1 to F6, wherein the plurality of portions comprises portions of varying size.

F8. The method of embodiment F7, wherein the plurality of portions comprises portions having sizes between about 30 kb to about 300 kb.

F9. The method of embodiment F7, wherein the plurality of portions comprises portions of about 32 kb.

F10. The method of embodiment F7, wherein the plurality of portions comprises portions of about 64 kb.

F11. The method of embodiment F7, wherein the plurality of portions comprises portions of about 128 kb.

F12. The method of embodiment F7, wherein the plurality of portions comprises portions of about 256 kb.

F13. The method of embodiment F7, wherein the plurality of portions does not comprise 50 kb portions.

F14. The method of any one of embodiments F1 to F13, comprising determining a GC content for the discrete segments in (b).

F15. The method of any one of embodiments F1 to F14, comprising sequencing nucleic acid from a test sample by a nucleotide sequencing process to generate nucleotide sequence reads.

F16. The method of embodiment F15, wherein the nucleic acid is circulating cell-free nucleic acid from a pregnant female bearing a fetus.

F17. The method of any one of embodiments F1 to F16, comprising mapping nucleotide sequence reads from a test sample to portions of a GC partitioned reference genome, thereby generating mapped nucleotide sequence reads.

F18. The method of embodiment F17, comprising normalizing counts of the mapped nucleotide sequence reads, thereby generating normalized counts.

F19. The method of embodiment F18, wherein the normalizing comprises LOESS normalization of guanine and cytosine (GC) bias (GC-LOESS normalization).

F20. The method of embodiment F17 or F18, wherein the normalizing comprises adjusting a sequence read count according to a median count.

F20.1 The method of embodiment F20, wherein the sequence read count is adjusted according to a median portion count.

F21. The method of any one of embodiments F17 to F20.1, wherein the normalizing comprises a principal component normalization.

F22. The method of any one of embodiments F18 to F21, wherein the normalizing comprises GC-LOESS normalization followed by normalization according to a median portion count followed by a principal component normalization.

F23. The method of any one of embodiments F18 to F22, comprising determining the presence or absence of a genetic variation for the test sample according to the normalized counts.

F23.1 The method of any one of embodiments F18 to F23, comprising determining a chromosome structure according to the normalized counts.

F23.2 The method of any one of embodiments F18 to F23.1, wherein the normalized counts are representative of chromosome dosage for the test sample.

F23.3 The method of embodiment F23.2, wherein determining a presence or absence of a genetic variation is according to the chromosome dosage.

F23.4 The method of any one of embodiments F23 to F23.3, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

F24. The method of embodiment F17, wherein the method does not comprise normalizing counts of the mapped nucleotide sequence reads.

F25. The method of embodiment F24, comprising determining the presence or absence of a genetic variation for the test sample according to raw counts of the mapped nucleotide sequence reads.

F26. The method of embodiment F24 or F25, comprising determining a chromosome structure according to raw counts of the mapped nucleotide sequence reads.

F27. The method of embodiment F25 or F26, wherein the raw counts are representative of chromosome dosage for the test sample.

F28. The method of embodiment F27, wherein determining a presence or absence of a genetic variation is according to the chromosome dosage.

F29. The method of any one of embodiments F25 to F28, wherein determining the presence or absence of a genetic variation for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for partitioning genomic regions of a reference genome comprising:
   a) obtaining nucleotide sequence reads from a plurality of samples comprising a mixture of maternal and fetal circulating cell-free nucleic acid;
   b) mapping the nucleotide sequence reads to the reference genome to obtain a training set of nucleotide sequence reads from the plurality of samples, wherein the training set of nucleotide sequences comprises from thousands to millions of sequence reads;
   c) determining sequencing coverage variability across the reference genome by quantification of the sequence reads of the training set of nucleotide sequence reads;
   d) selecting an initial portion length for portions of the genomic regions based on features of the training set of nucleotide sequence reads;
   e) partitioning at least two genomic regions into a number of portions according to the initial portion length in (d), wherein the at least two genomic regions comprise a first genomic region and a second genomic region;
   f) comparing the sequencing coverage variability determined in (c) for the first genomic region to the sequencing coverage variability determined in (c) for the second genomic region, wherein the comparing comprises calculating a proportionality factor comprising a ratio between the sequencing coverage variability of the first region and the sequencing coverage variability of the second region;
   g) recalculating the number of portions for the first genomic region and the second genomic region according to the proportionality factor;
   h) determining an optimized portion length for the first genomic region and the second genomic region based on the recalculated number of portions; and
   i) re-partitioning the first genomic region and the second genomic region into a plurality of portions according to the optimized portion length determined in (h).

2. The method of claim 1, wherein the plurality of samples are from pregnant females bearing a fetus.

3. The method of claim 1, wherein the feature of the training set of nucleotide sequence reads used to select the initial portion length in (d) is:
   i) sequencing depth for the training set;
   ii) an average fetal fraction for the training set; or
   iii) sequencing depth for the training set and an average fetal fraction for the training set.

4. The method of claim 1, wherein the initial portion length is between about 1 kb to about 1000 kb.

5. The method of claim 1, wherein a total number of portions for the reference genome is determined according to the initial portion length in (d), and the number of portions for the first genomic region and the second genomic region are recalculated according to the proportionality factor and the total number of portions for the reference.

6. The method of claim 1, wherein the first genomic region and the second genomic region are substantially similar in size.

7. The method claim 1, wherein the proportionality factor (P) is calculated according to the following equation:

$$P = (var_1/var_2)^{1/3} \quad \text{equation A}$$

wherein $var_1$ is the sequencing coverage variability of the first genomic region and $var_2$ is the sequencing coverage variability of the second genomic region.

8. The method of claim 7, wherein the sequencing coverage variability of the first genomic region is determined from a nucleotide sequence read count, or a derivative thereof, for the first genomic region, and wherein sequencing coverage variability of the second genomic region is determined from a nucleotide sequence read count, or a derivative thereof, for the second genomic region.

9. The method of claim 8, wherein the nucleotide sequence read count is a normalized nucleotide sequence read count.

10. The method of claim 7, wherein the sequencing coverage variability of the first genomic region is determine from an average nucleotide sequence read count, or a derivative thereof, for the first genomic region, and wherein sequencing coverage variability of the second genomic region is determined from an average nucleotide sequence read count, or a derivative thereof, for the second genomic region.

11. The method of claim 10, wherein the average nucleotide sequencing read counts for each genomic region are determined using a training set.

12. The method of claim 10, wherein the average nucleotide sequence read count is an average normalized nucleotide sequence read count.

13. The method of claim 1, wherein the plurality of portions in (i) comprises portions of constant size.

14. The method of claim 1, wherein the plurality of portions in (i) comprises portions of varying size.

15. The method of claim 1, wherein the plurality of portions in (i) comprises portion lengths of between about 1 kb to about 1000 kb.

16. The method of claim 1, further comprising (j) mapping nucleotide sequence reads from a test sample to the re-partitioned plurality of portions of the reference genome, thereby generating mapped nucleotide sequence reads, and normalizing counts of the mapped nucleotide sequence reads, thereby generating normalized counts.

17. The method of claim 1, further comprising (k) determining the presence or absence of a genetic variation for the test sample according to the normalized counts.

18. The method of claim 1, further comprising (j) mapping nucleotide sequence reads from a test sample to the re-partitioned plurality of portions of the reference genome, thereby generating mapped nucleotide sequence reads, and determining the presence or absence of a genetic variation for the test sample according to raw counts of the mapped nucleotide sequence reads.

19. A system for partitioning genomic regions of a reference genome, the system comprising:
   one or more data processors; and
   a non-transitory computer readable storage medium containing instructions which, when executed on the one or more data processors, cause the one or more data processors to perform actions including:
      obtaining nucleotide sequence reads from a plurality of samples comprising a mixture of maternal and fetal circulating cell-free nucleic acid;
      mapping the nucleotide sequence reads to the reference genome to obtain a training set of nucleotide sequence reads from the plurality of samples, wherein the training set of nucleotide sequences comprises from thousands to millions of sequence reads;
      determining sequencing coverage variability across the reference genome by quantification of the sequence reads of the training set of nucleotide sequence reads;

selecting an initial portion length for portions of the genomic regions based on features of the training set of nucleotide sequence reads;

partitioning at least two genomic regions into a number of portions according to the initial portion length, wherein the at least two genomic regions comprise a first genomic region and a second genomic region;

comparing the sequencing coverage variability for the first genomic region to the sequencing coverage variability determined for the second genomic region, wherein the comparing comprises calculating a proportionality factor comprising a ratio between the sequencing coverage variability of the first region and the sequencing coverage variability of the second region;

recalculating the number of portions for the first genomic region and the second genomic region according to the proportionality factor;

determining an optimized portion length for the first genomic region and the second genomic region based on the recalculated number of portions; and re-partitioning the first genomic region and the second genomic region into a plurality of portions according to the optimized portion length.

20. A computer-program product tangibly embodied in a non-transitory machine-readable storage medium, including instructions configured to cause one or more data processors to perform actions including:

obtaining nucleotide sequence reads from a plurality of samples comprising a mixture of maternal and fetal circulating cell-free nucleic acid;

mapping the nucleotide sequence reads to the reference genome to obtain a training set of nucleotide sequence reads from the plurality of samples, wherein the training set of nucleotide sequences comprises from thousands to millions of sequence reads;

determining sequencing coverage variability across the reference genome by quantification of the sequence reads of the training set of nucleotide sequence reads;

selecting an initial portion length for portions of the genomic regions based on features of the training set of nucleotide sequence reads;

partitioning at least two genomic regions into a number of portions according to the initial portion length, wherein the at least two genomic regions comprise a first genomic region and a second genomic region;

comparing the sequencing coverage variability for the first genomic region to the sequencing coverage variability determined for the second genomic region, wherein the comparing comprises calculating a proportionality factor comprising a ratio between the sequencing coverage variability of the first region and the sequencing coverage variability of the second region;

recalculating the number of portions for the first genomic region and the second genomic region according to the proportionality factor;

determining an optimized portion length for the first genomic region and the second genomic region based on the recalculated number of portions; and re-partitioning the first genomic region and the second genomic region into a plurality of portions according to the optimized portion length.

* * * * *